US012661393B2

(12) United States Patent
Singh et al.

(10) Patent No.: US 12,661,393 B2
(45) Date of Patent: Jun. 23, 2026

(54) BCG BASED VACCINE COMPOSITIONS AND METHODS OF USE THEREOF

(71) Applicant: The Johns Hopkins University, Baltimore, MD (US)

(72) Inventors: Alok Singh, Baltimore, MD (US); Peter Um, Baltimore, MD (US); Keira Cohen, Baltimore, MD (US); William Bishai, Baltimore, MD (US); Rulin Wang, Baltimore, MD (US); Srinivasan Yegnasubramanian, Baltimore, MD (US); Trinity J. Bivalacqua, Philadelphia, PA (US)

(73) Assignee: The Johns Hopkins University, Baltimore, MD (US)

( * ) Notice: Subject to any disclaimer, the term of this patent is extended or adjusted under 35 U.S.C. 154(b) by 407 days.

(21) Appl. No.: 18/029,599

(22) PCT Filed: Oct. 1, 2021

(86) PCT No.: PCT/US2021/053234
§ 371 (c)(1),
(2) Date: Mar. 30, 2023

(87) PCT Pub. No.: WO2022/072877
PCT Pub. Date: Apr. 7, 2022

(65) Prior Publication Data
US 2024/0009292 A1      Jan. 11, 2024

Related U.S. Application Data

(60) Provisional application No. 63/086,559, filed on Oct. 1, 2020.

(51) Int. Cl.
*A61K 39/04*         (2006.01)
*A61K 35/74*         (2015.01)
(Continued)

(52) U.S. Cl.
CPC .............. *A61K 39/04* (2013.01); *A61K 35/74* (2013.01); *A61P 31/14* (2018.01); *A61K 2039/5254* (2013.01); *A61K 2039/58* (2013.01)

(58) Field of Classification Search
CPC ................... A61K 39/04; A61K 35/74; A61K 2039/5254; A61K 2039/58;
(Continued)

(56) References Cited

U.S. PATENT DOCUMENTS 5,399,363 A      3/1995  Liversidge et al.
5,466,468 A      11/1995  Schneider et al.
(Continued)

FOREIGN PATENT DOCUMENTS

CN      106479946 A      3/2017
CN      107217026 A      9/2017
(Continued)

OTHER PUBLICATIONS

CN Office Action in Chinese Application No. 2019800405920, dated Dec. 6, 2023, 15 pages (with English translation).
(Continued)

*Primary Examiner* — Robert B Mondesi
(74) *Attorney, Agent, or Firm* — DLA Piper LLP (US)

(57) ABSTRACT

The present disclosure relates to a BCG based therapeutic agent using a BCG strain that overexpresses the STING agonist, c-di-AMP. This BCG strain, called BCG-disA-OE, enhances the elevated trained immunity of macrophages and promotes early anti-viral Type I interferon responses in a subject, providing protection against viral infections such as primary respiratory infections and SARS-CoV-2 infection.

14 Claims, 23 Drawing Sheets

Specification includes a Sequence Listing.

(51) Int. Cl.
    *A61P 31/14*        (2006.01)
    *A61K 39/00*        (2006.01)
(58) Field of Classification Search
    CPC ...... A61K 2039/55561; A61K 2039/57; A61K
            39/39; A61P 31/14; A61P 31/06; A61P
            35/00; A61P 37/04; C12R 2001/32; C07K
                                    14/35; C12N 15/74
    USPC ........................................................ 424/93.4
    See application file for complete search history.

(56)                  References Cited

U.S. PATENT DOCUMENTS

| | | | |
|---|---|---|---|
| 5,543,158 A | 8/1996 | Gref et al. | |
| 5,580,579 A | 12/1996 | Ruddy et al. | |
| 5,629,001 A | 5/1997 | Michael et al. | |
| 5,641,515 A | 6/1997 | Ramtoola | |
| 5,725,871 A | 3/1998 | Illum | |
| 5,756,353 A | 5/1998 | Debs | |
| 5,780,045 A | 7/1998 | McQuinn et al. | |
| 5,792,451 A | 8/1998 | Sarubbi et al. | |
| 5,804,212 A | 9/1998 | Illum | |
| 6,613,308 B2 | 9/2003 | Bartus et al. | |
| 9,926,346 B2 | 3/2018 | Fulkerson et al. | |
| 10,596,160 B2 | 3/2020 | Cohen et al. | |
| 10,842,828 B2 | 11/2020 | Bishai et al. | |
| 10,962,539 B2 | 3/2021 | Prokunina et al. | |
| 10,973,470 B2 | 4/2021 | Newberry et al. | |
| 2010/0183547 A1 | 7/2010 | Horwitz et al. | |
| 2015/0071873 A1 | 3/2015 | Biot et al. | |
| 2017/0254808 A1 | 9/2017 | Prokunina et al. | |
| 2018/0028577 A1 | 2/2018 | Bishai et al. | |
| 2019/0008841 A1 | 1/2019 | Cohen et al. | |
| 2019/0030091 A1 * | 1/2019 | Bishai | A61P 35/00 |
| 2019/0336544 A1 | 11/2019 | Falb et al. | |
| 2020/0253562 A1 | 8/2020 | Newberry et al. | |

FOREIGN PATENT DOCUMENTS

| | | | |
|---|---|---|---|
| MX | 2015015918 A | 5/2017 | |
| WO | WO 2008/140598 A2 | 11/2008 | |
| WO | WO 2016130616 A1 | 8/2016 | |
| WO | WO-2017011444 A1 | 1/2017 | |
| WO | WO 2017049127 A1 | 3/2017 | |
| WO | WO-2018112360 A1 | 6/2018 | |
| WO | WO-2019203965 A1 * | 10/2019 | ............. A61K 39/39 |
| WO | WO-2020002905 A1 | 1/2020 | |
| WO | WO-2021163602 A1 * | 8/2021 | ............. A61K 35/74 |

OTHER PUBLICATIONS

Fang et al., " Physiological Function of Second Messenger Cyclic Diguanylate Signaling in *Mycobacterium tuberculosis*", China Doctoral Dissertation Full-text Database, Jul. 2015, E059-41, 115 pages (with English abstract).
EP Search Report in European Application No. 21754580.5, dated Apr. 10, 2024, 7 pages.
JP Office Action in Japanese Application No. 2020-557965, dated Aug. 2, 2024, 7 pages (with English translation).
Zaczek et al., "Genetic evaluation of relationship between mutations in rpoB and resistance of *Mycobacterium tuberculosis* to rifampin", BMC Microbiology, Jan. 2009, 9:10, 8 pages.
Canadian Examination Report for Canadian Patent Application No. 3,097,569 issued Jan. 21, 2025, 5 pages.
Extended European Search Report for European Patent Application No. 21876626.9 issued Feb. 11, 2025, 8 pages.
Rotcheewaphan, S., "Characterization of *Mycobacterium leprae* diguanylate cyclases", Ph.D. Dissertation, Colorado State University, Fort Collins, Colorado, Summer 2016, 237pp., downloaded from the internet on Jan. 19, 2025 (Jan. 19, 2025): https://api.mountainscholar.org/server/api/core/bitstreams/7272eddf-631f-420a-b828-ccadd5be4dc6/content.

Sambandamurthy et al., "A pantothenate auxotroph of *Mycobacterium tuberculosis* is highly attenuated and protects mice against tuberculosis," Nature Medicine, vol. 8, No. 10, Oct. 2022, 1171-1174.
CN Office Action in Chinese Application No. 201980040592 dated May 13, 2023, 17 pages (with English translation).
Rayn, "New therapies in nonmuscle invasive bladder cancer treatment", Indian J Urol, Mar. 2018, 34(1): 11-19.
Sambandamurthy, "*Mycobacterium tuberculosis* ΔRD1 ΔpanCD: A safe and limited replicating mutant strain that protects immunocompetent and immunocompromised mice against experimental tuberculosis", Sep. 2006, Vaccine, 24:6309-6320.
Ablasser A., et al., "Cell Intrinsic Immunity Spreads to Bystander Cells via The Intercellular Transfer To cGAMP," Nature, Nov. 28, 2013, vol. 503, No. 7477, pp. 530-534.
Agarwal N., et al., "Cyclic AMP Intoxication Of Macrophages by a *Mycobacterium tuberculosis* Adenylate Cyclase," Nature, Jul. 2, 2009, vol. 460, pp. 98-102.
Ahmed D., et al., "Role of Cellular Metabolism in Regulating Type I Interferon Responses: Implications for Tumor Immunology and Treatment," Cancer Letters, Nov. 28, 2017, vol. 409, pp. 20-29.
Askeland E.J., et al., "Bladder Cancer Immunotherapy: BCG and Beyond," Advances in Urology, May 2012, vol. 2012, Article ID. 181987, 14 Pages.
Bai Y., et al., "*Mycobacterium tuberculosis* Rv3586 (DacA) is a Diadenylate Cyclase that Converts ATP or ADP into c-di-AMP," PLoS One, PMID: 22529992, Apr. 17, 2012, vol. 7, No. 4, Article e35206, 10 Pages.
Bai Y., et al., "Two Dhh Subfamily 1 Proteins In *Streptococcus pneumoniae* Possess Cyclic Di-amp Phosphodiesterase Activity And Affect Bacterial Growth And Virulence," Journal of Bacteriology, Nov. 2013, vol. 195, No. 22, pp. 5123-5132.
Barker J.R., et al., "Sting-Dependent Recognition Of Cyclic Di-AMP Mediates Type I Interferon Responses During Chlamydia Trachomatis Infection," MBio, May-Jun. 2013, vol. 4, No. 3, Article e00018-00013, 11 Pages.
Bharati B.K., et al., "A Full-length Bifunctional Protein Involved In C-di-gmp Turnover Is Required For Long-term Survival Under Nutrient Starvation In *Mycobacterium smegmatis*," Microbiology, Jun. 2012, vol. 158(Pt 6), pp. 1415-1427.
Bowie A.G., et al., "Innate Sensing of Bacterial Cyclic Dinucleotides: More Than Just STING," Nature Immunology, Dec. 2012, vol. 13, No. 12, pp. 1137-1139.
Burdette D.L., et al., "STING is a Direct Innate Immune Sensor of Cyclic Di-GMP," Nature, Oct. 27, 2011, vol. 478, pp. 515-518.
Cai X., et al., "The cGAS-cGAMP-STING Pathway of Cytosolic DNA Sensing and Signaling," Molecular Cell, Apr. 24, 2014, vol. 54, pp. 289-296.
Cho K.H., et al., "*Streptococcus pyogenes* c-di-AMP Phosphodiesterase, GdpP, Influences SpeB Processing and Virulence," PLoS One, Jul. 2013, vol. 8, Issue. 7, e69425, 12 Pages, DOI:10.1371/journal.pone.0069425.
Collins A.C., et al., "Cyclic GMP-AMP Synthase Is an Innate Immune DNA Sensor for *Mycobacterium tuberculosis*," Cell Host & Microbe, Jun. 10, 2015, vol. 17, pp. 820-828.
Corrigan R.M., et al., "c-di-AMP Is a New Second Messenger in *Staphylococcus aureus* with a Role in Controlling Cell Size and Envelope Stress," PLos Pathogens, Sep. 2011, vol. 7, Issue. 9, 16 pages.
Corrigan R.M., et al., "Cyclic di-AMP: Another Second Messenger Enters the Fray," Nature Reviews Microbiology, Aug. 2013, vol. 11, 29 pages.
Dey B., et al., "A Bacterial Cyclic Dinucleotide Activates The Cytosolic Surveillance Pathway And Mediates Innate Resistance To Tuberculosis," Nature Medicine, Apr. 2015, vol. 21, No. 4, pp. 401-406, 13 Pages.
Dey B., et al., "Crosstalk between *Mycobacterium tuberculosis* and the Host Cell," Seminars in Immunology, Dec. 2014, vol. 26, No. 6, pp. 486-496.
Dey R.J., et al., "Inhibition of Innate Immune Cytosolic Surveillance by a *Mycobacterium tuberculosis* Phosphodiesterase," Nature Chemical Biology, Feb. 2017, vol. 13, pp. 210-217.

(56)          References Cited

OTHER PUBLICATIONS

Diner E.J., et al., "The Innate Immune Dna Sensor Cgas Produces A Noncanonical Cyclic Dinucleotide That Activates Human STING," Cell Reports, PMID: 23707065, May 30, 2013, vol. 3, pp. 1355-1361.

Du B., et al., "Functional Analysis of c-di-AMP Phosphodiesterase, GdpP, in *Streptococcus suis* Serotype 2," Microbiological Research, Sep.-Oct. 2014, vol. 169(9-10), pp. 749-758.

Evans M.R.W., et al., "Squamous Cell Carcinoma Secondary to Buruli Ulcer," Transactions of the Royal Society of Tropical Medicine and Hygiene, 1999, vol. 93, pp. 63-64.

Extended European Search Report for European Application No. 19787889.5, mailed Jan. 19, 2022, 08 Pages.

Extended European Search Report for European Application No. 19878893.5, mailed Jan. 19, 2022, 09 Pages.

Fitzgerald K.A., et al., "IKKepsilon and TBKI are Essential Components of the IRF3 Signaling Pathway," Nature Immunology, May 2003, vol. 4, No. 5, pp. 491-496.

Francica B.J., et al., "TNFa and Radioresistant Stromal Cells are Essential for Therapeutic Efficacy of Cyclic Dinucleotide STING Agonists in Nonimmunogenic Tumors," Cancer Immunology Research, Apr. 2018, vol. 6, No. 4, pp. 423-433, 25 Pages.

Gao D., et al., "Cyclic GMP-AMP Synthase Is An Innate Immune Sensor Of Hiv And Other Retroviruses," Science, Aug. 23, 2013, vol. 341, 09 pages.

Gupta K., et al., "Identification, Activity and Disulfide Connectivity of C-di-GMP Regulating Proteins in *Mycobacterium tuberculosis*," PLoS One, Nov. 30, 2010, vol. 5, No. 11, e 15072, 19 pages.

Hansen K., et al., "Listeria Monocytogenes Induces Ifni3 Expression Through An I FI 16-, cGAS- And Sting-dependent Pathway," The EMBO Journal, Aug. 1, 2014, vol. 33, No. 15, pp. 1654-1666.

Hornung V., et al., "OAS proteins and cGAS: Unifying Concepts in Sensing and Responding to Cytosolic Nucleic Acids," Nature Reviews Immunology, Aug. 2014, vol. 14, No. 8, pp. 521-528.

Hwang J.S., et al., "Synthesis Of Sulfonylurea Conjugated Copolymer Via PEO Spacer And Its In Vitro Short-term Bioactivity In Insulin Secretion From Islets Of Langerhans," Biomaterials, Jul. 19, 1998, vol. 13, pp. 1189-1195.

Hwang M.J., et al., "Derivation of Class II Force Fields. VI. Carbohydrate Compounds and Anomeric Effects," Biopolymers, May 1998, vol. 45 No. 6, pp. 435-468.

Hwang S-J., et al., "Gastric Retentive Drug-Delivery Systems," Critical Reviews in Therapeutic Drug Carrier System, 1998, vol. 15, No. 3, pp. 243-284.

International Search Report and Written Opinion for International Application No. PCT/US2019/022341, mailed Jul. 4, 2019, 10 Pages.

International Search Report and Written Opinion for International Application No. PCT/US2021/018007, mailed Apr. 29, 2021, 10 Pages.

International Search Report and Written Opinion for International Application No. PCT/US2021/053234, dated Mar. 3, 2022, 12 Pages.

Kalia D., et al., "Nucleotide, c-di-GMP, c-di-AMP, cGMP, CAMP, (p)ppGpp Signaling in Bacteria and Implications in Pathogenesis," Chemical Society Review, Jan. 7, 2013, vol. 42, No. 1, pp. 305-341.

Kates M., et al., "Intravesical BCG Induces CD4+ T-Cell Expansion in an Immune Competent Model of Bladder Cancer," Cancer Immunology Research, Jul. 2017, vol. 5, No. 7, pp. 594-603.

Kim M-J., et al., "Caseation Of Human Tuberculosis Granulomas Correlates With Elevated Host Lipid Metabolism," EMBO Molecular Medicine, May 2010, vol. 2, pp. 258-274.

Konno H., et al., "Cyclic Dinucleotides Trigger ULK1 (ATG1) Phosphorylation of STING to Prevent Sustained Innate Immune Signaling," Cell, Oct. 24, 2013, vol. 155, No. 3, 24 pages.

Kranzusch P.J., et al., "Structure of Human cGAS Reveals a Conserved Family of Second-messenger Enzymes in Innate Immunity," Cell Reports, May 30, 2013, vol. 3, No. 5, pp. 1362-1368.

Kubota K., et al., "Identification of 2'-Phosphodiesterase, Which Plays a Role in the 2-5A Systems Regulated by Interferon," The Journal of Biological Chemistry, Sep. 3, 2004, vol. 279, No. 36, pp. 37832-37841.

Lahaye X., et al., "The Capsids of HIV-1 and HIV-2 Determine Immune Detection of The Viral cDNA By The Innate Sensor Gas In Dendritic Cells," Immunity, Dec. 12, 2013, vol. 39, No. 6, pp. 1132-1142.

Lamichhane G., et al., "A Postgenomic Method For Predicting Essential Genes At Subsaturation Levels Of Mutagenesis: Application To *Mycobacterium tuberculosis*," Proceedings of the National Academy of Sciences of the United States of America, Jun. 10, 2003, vol. 100, No. 12, pp. 7213-7218.

Lau L., et al., "DNA Tumor Virus Oncogenes Antagonize the cGAS-STING DNA-sensing Pathway," Science, Oct. 30, 2015, vol. 350, Issue. 6260, pp. 568-571.

Li L., et al., "Hydrolysis of 2'3'-cGAMP by ENPP1 and Design of Nonhydrolyzable Analogs," Nature Chemical Biology, Dec. 2014, vol. 10(12), pp. 1043-1048.

Li T., et al., "Human Cytomegalovirus Tegument Protein pUL83 Inhibits IFI16-mediated DNA Sensing for Immune Evasion," Cell Host & Microbe, Nov. 13, 2013, vol. 14, No. 5, 18 pages.

Li X-D., et al., "Pivotal Roles of cGAS-cGAMP Signaling in Antiviral Defense and Immune Adjuvant Effects," Science, Sep. 20, 2013, vol. 341(6152), pp. 1390-1394.

Li Y., et al., "Regulating STING in Health and Disease," Journal of Inflammation, Jun. 2017, vol. 14, No. 11, pp. 1-21.

Liang Q., et al., "Crosstalk Between the cGAS DNA Sensor and Beclin-1 Autophagy Protein Shapes Innate Antimicrobial Mmune Responses," Cell Host & Microbe, Feb. 12, 2014, vol. 15, No. 2, pp. 228-238.

Malen H., et al., "Definition of Novel Cell Envelope Associated Proteins in Triton X-114 Extracts of *Mycobacterium tuberculosis* H37Rv," BMC Microbiology, Apr. 29, 2010, vol. 10, No. 132, 11 Pages.

Manikandan K., et al., "Two-step Synthesis And Hydrolysis Of Cyclic Di-AMPIn *Mycobacterium tuberculosis*," PLoS One, Jan. 23, 2014, vol. 9, Issue. 1, e86096, 12 pages.

Manzanillo P.S., et al., "*Mycobacterium tuberculosis* Activates The DNA-Dependent Cytosolic Surveillance Pathway Within Macrophages," Cell Host and Microbe, May 17, 2012, vol. 11, No. 5, pp. 469-480.

Mathiowitz E., et al., "Biologically Erodable Microspheres as Potential Oral Drug Delivery Systems," Nature, Mar. 27, 1997, vol. 386, pp. 410-414.

Morales A., "BCG: A Throwback from the Stone Age of Vaccines Opened the Path for Bladder Cancer Immunotherapy," The Canadian Journal of Urology, Jun. 2017, vol. 24, No. 3, pp. 8788-8793.

Office Action for Japanese Patent Application No. 2020557965, mailed Feb. 7, 2023, 12 Pages.

Orzalli M.H., et al., "Nuclear IFI16 Induction of IRF-3 Signaling During Herpesviral Infection And Degradation Of IFI16 by The Viral ICPO Protein," Proceedings of the National Academy of Sciences of USA, Oct. 30, 2012, vol. 109, No. 44, pp. E3008-E3017.

Parvatiyar K., et al., "The Helicase DDX41 Recognizes The Bacterial Secondary Messengers Cyclic Di-GMP And Cyclic Di-AMP To Activate A Type I Interferon Immune Response," Nature Immunology, Dec. 2012, vol. 13, pp. 1155-1161.

Postic G., et al., "Characterization of NmA Homologs From *Mycobacterium tuberculosis* And *Mycoplasma pneumoniae*," RNA, Jan. 2012, vol. 18, No. 1, pp. 155-165.

Powles T., et al., "MPDL3280A (Anti-PD-LI) Treatment Leads to Clinical Activity in Metastatic Bladder Cancer," Nature, Nov. 27, 2014, vol. 515, No. 7528, pp. 558-562, 12 Pages, XP055207741, DOI:10.1038/nature13904.

Rachman H., et al., "Unique Transcriptome Signature Of *Mycobacterium tuberculosis* In Pulmonary Tuberculosis," Infection and Immunity, Feb. 2006, vol. 74, No. 2, pp. 1233-1242.

Rao F., et al., "YybT Is A Signaling Protein That Contains A Cyclic Dinucleotide Phosphodiesterase Domain And A GGDEF Domain With ATPase Activity," Journal of Biological Chemistry, Jan. 1, 2010, vol. 285, No. 1, pp. 473-482.

(56) References Cited

OTHER PUBLICATIONS

Rederlman-Sidi G., et al., "The Mechanism Of Action Of BCG Therapy For Bladder Cancer-a Current Perspective," Nature Reviews Urology, Mar. 2014, vol. 11, No. 3, pp. 153-162.

Romling U., "Great times for Small Molecules: c-di-AMP, a Second Messenger Candidate in Bacteria and Archaea," Science Signaling, Aug. 19, 2008, vol. 01, No. 33, 5 Pages.

Rorbach J., et al., "PDE12 Removes Mitocondrial RNA poly(a) Tails and Controls Translation in Human Mitochondria," Nucleic Acids Research, Jun. 11, 2011, vol. 39, No. 17, pp. 7750-7763.

Schirmer T., et al., "Structural And Mechanistic Determinants Of C-di-Gmp Signalling," Nature Reviews Microbiology, Oct. 2009, vol. 7, No. 10, pp. 724-735.

Siddiqui M.R., et al., "Current Clinical Trials In Non-muscle Invasive Bladder Cancer," Urologic Oncology, Aug. 2017, vol. 35, No. 8, pp. 516-527, DOI: 10.1016/j.urolonc.2017.06.043, XP085150983.

Silverman, et al., Viral Phosphodiesterases That Antagonize Double-stranded to RNase L by Degrading 2-5A, Journal Of Interferon & Cytokine Research, Jun. 2014, vol. 34, No. 6, pp. 455-463.

Srivastav R., et al., "Unique Subunit Packing in Mycobacterial nanoRNase Leads to Alternate Substrate Recognitions in DHH Phosphodiesterases," Nucleic Acids Research, Jul. 2014, vol. 42, No. 12, pp. 7894-7910.

Sun L., et al., "Cyclic GMP-AMP Synthase Is A Cytosolic DNA Sensor That Activates The Type I Interferon Pathway," Science, Feb. 15, 2013, vol. 339, No. 6121, pp. 786-791.

Takenaga M., et al., "Microparticle Resins as a Potential Nasal Drug Delivery System for Insulin," Journal of Controlled Release, 1998, vol. 52, pp. 81-87.

Wang J., et al., "Conservative Change to the Phosphate Moiety of Cyclic Diguanylic Monophosphate Remarkably Affects its Polymorphism and Ability To Bind DGC, PDE, and PilZ Proteins," Journal of the American Chemical Society, May 2011, vol. 133, No. 24, pp. 9320-9330.

Wassermann R., et al., "*Mycobacterium tuberculosis* Differentially Activates cGAS- and Inflammasome-Dependent Intracellular Immune Responses through ESX-1," Cell Host & Microbe, Jun. 10, 2015, vol. 17, pp. 799-810.

Watson R.O., et al., "The Cytosolic Sensor cGAS Detects Mycobacterium tuberculosis DNA to Induce Type I Interferons and Activate Autophagy," Cell Host and Microbe, Jun. 10, 2015, vol. 17, pp. 811-819.

Witte C.E., et al., "Cyclic Di-AMP is Critical for Listeria Monocytogenes Growth, Cell Wall homeostasis, and Establishment of Infection," Molecular Biology, May 29, 2013, vol. 4, No. 3, e00282-13, DOI: 10.1128/mBio.00282-13.

Woodward J.J., et al., "c-di-AMP Secreted by Intracellular Listeria Monocytogenes Activates a Host Type I Interferon Response," Science, Jun. 25, 2010, vol. 328, No. 5986, pp. 1703-1705.

Wu et al., "Cyclic GMP-AMP is an Endogenous Second Messenger in Innate Immune Signaling by Cytosolic DNA," Science, Feb. 15, 2013, vol. 339, No. 6121, pp. 826-830.

Wu J.J., et al., "Inhibition of cGAS DNA Sensing by a Herpesvirus Virion Protein," Cell Host Microbe, Sep. 9, 2015, vol. 18, No. 3, pp. 333-344.

Yang J., et al., "Deletion of the Cyclic Di-AMP Phosphodiesterase Gene (cnpB) in *Mycobacterium tuberculosis* Leads to Reduced Virulence in a Mouse Model of Infection," Molecular Microbiology, 2014, vol. 93, No. 1, pp. 65-79.

Zhang Y., et al., "The DNA sensor, Cyclic GMP-AMP Synthase, is Essential for Induction of IFN Beta During Chlamydia trachomatis infection," The Journal of Immunology, Sep. 1, 2014, vol. 193 No. 5, pp. 2394-2404.

Zhao G.N., et al., "Interferon Regulatory Factors: at the Crossroads of Immunity, Metabolism, and Disease," Biochimica et Biophysica Acta, Feb. 2015, vol. 1852, No. 2, pp. 365-378.

Zhu D., et al., "Structural Biochemistry of a Vibrio Cholerae Dinucleotide Cyclase Reveals Cyclase Activity Regulation by Folates," Molecular Cell, Elsevier, Amsterdam, NL, Sep. 18, 2014, vol. 55, No. 6, pp. 931-937, DOI: 10.1016/J.MOLCEL.2014.08.001, ISSN: 1097-2765, XP029062183.

Zitvogel L., et al., "Type I Interferons in Anticancer Immunity," Nature Reviews Immunology, Jul. 2015, vol. 15, pp. 405-414.

Kamat, et al., "BCG Against SARS-CoV-2: Second Youth of an Old Age Vaccine?" Frontiers in Pharmacology, vol. 11, Article 1050, Jul. 9, 2020, 6 pages.

Notice of Reasons for Refusal for JP2023-520398 mailed Aug. 19, 2025, 6 pages.

Tullius, et al., "A Replication-Limited Recombinant *Mycobacterium bovis* BCG Vaccine against Tuberculosis Designed for Human Immunodeficiency Virus-Positive Persons Is Safer and More Efficacious than BCG," Infection and Immunity, vol. 76, No. 11, Nov. 1, 2008, pp. 5200-5214.

Non-Final Office Action for U.S. Appl. No. 16/638,943 mailed Jun. 13, 2025, 18 pages.

* cited by examiner

A
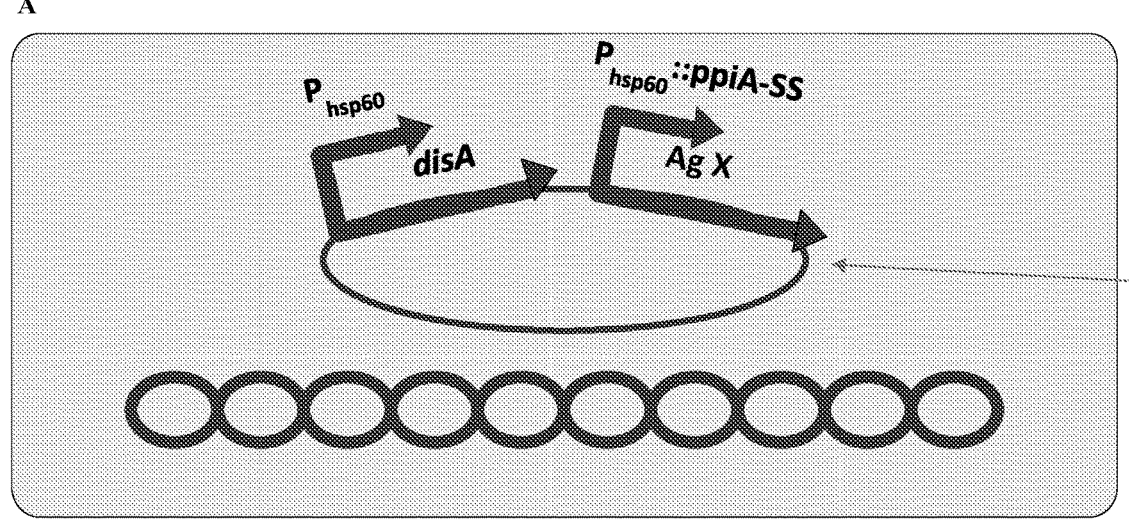
B
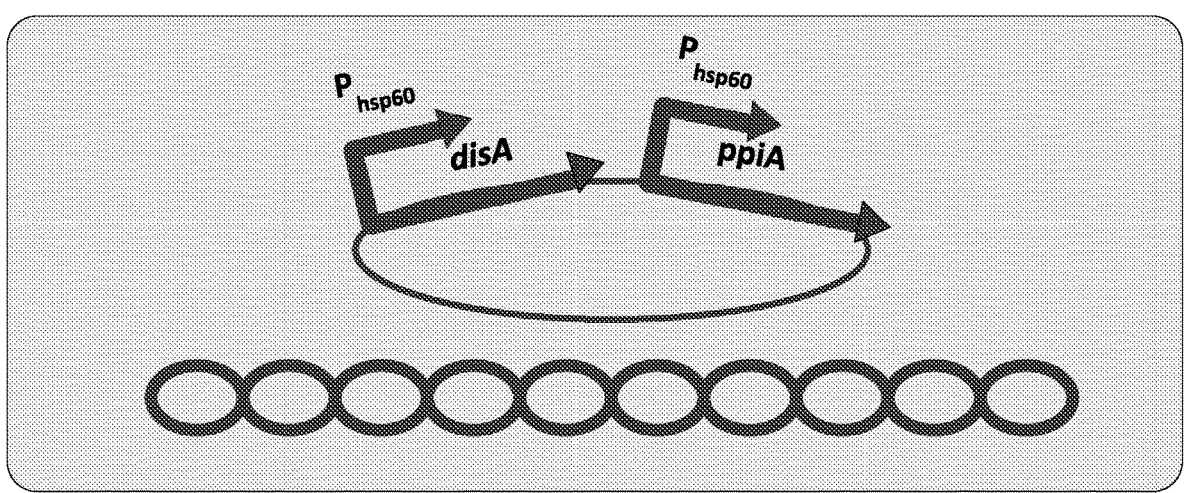
FIGURES 2A-B

C

A
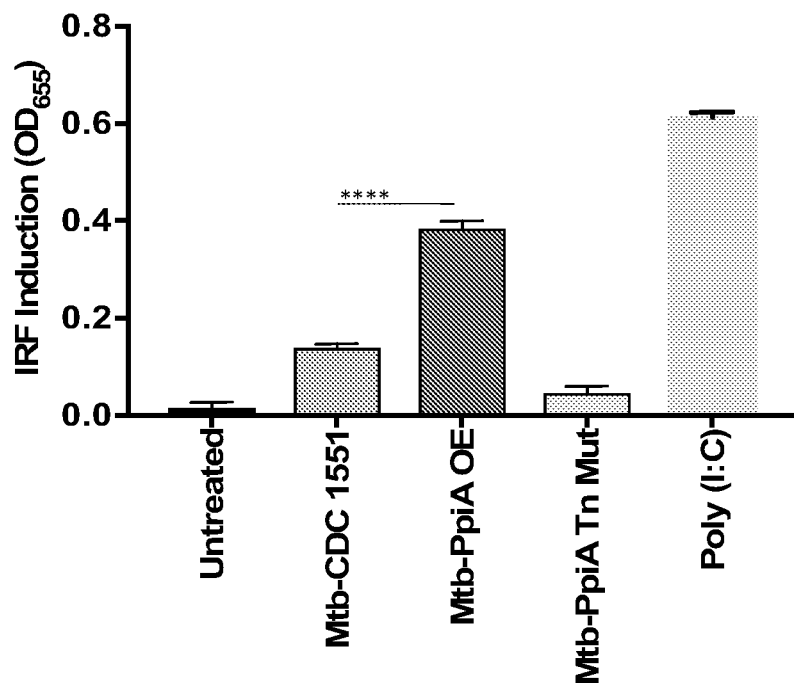
B
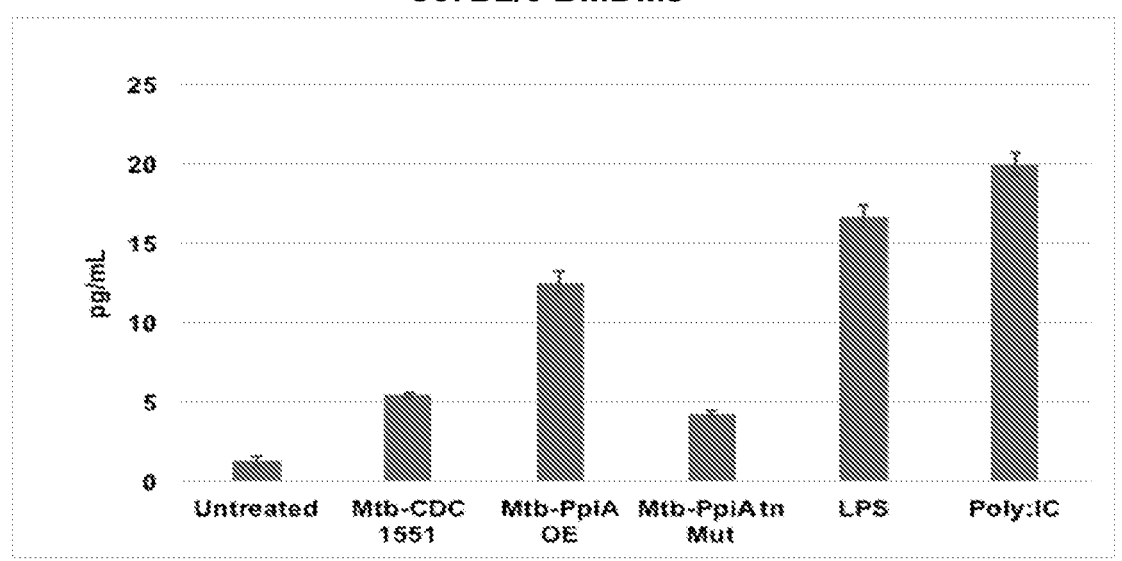
FIGURES 3A-B

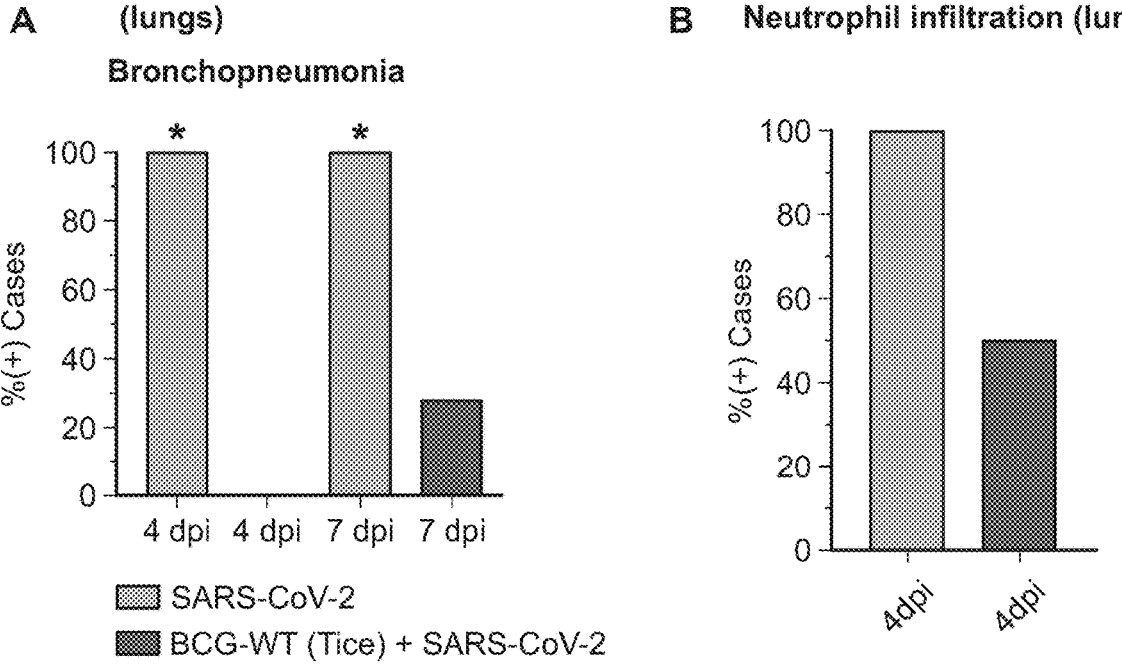
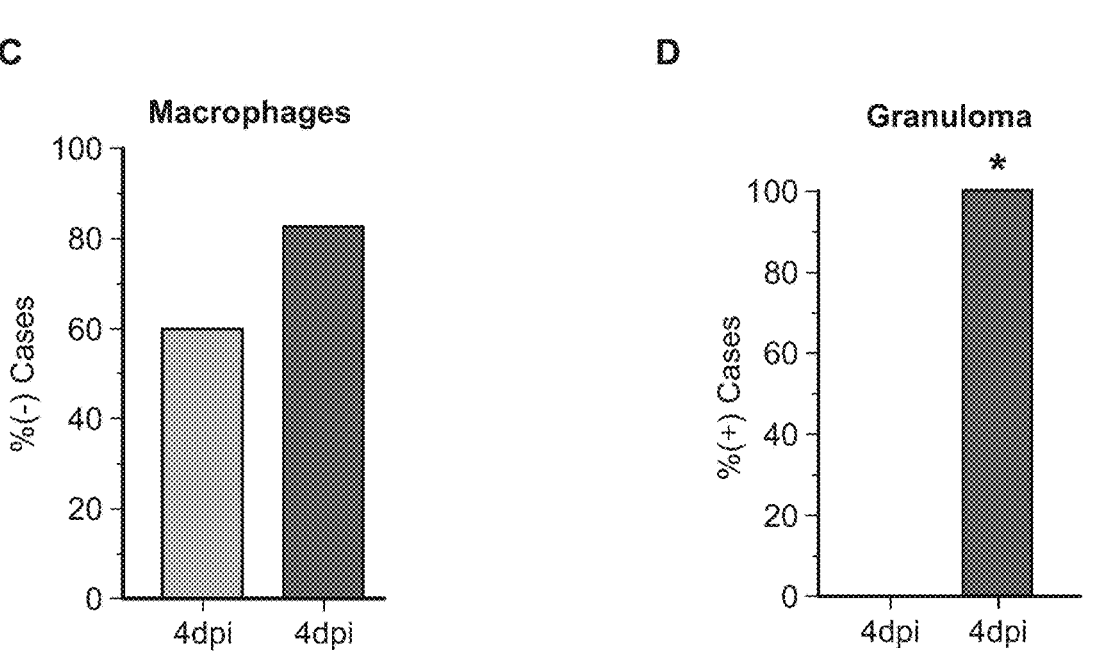
FIGURES 4A-D a. CD3+ T cells (lungs)
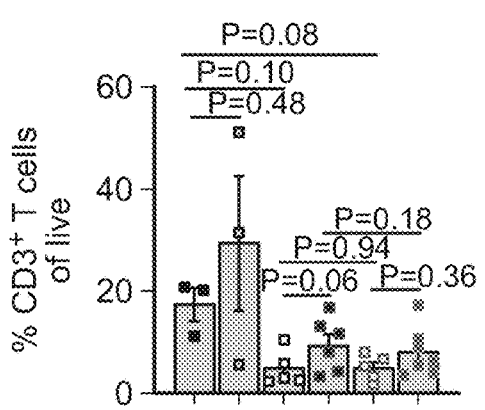
* Age matched controls
* BCG-STING (Tice)
* SARS-CoV-2 (Day 04)
* BCG-STING (Tice) + SARS-CoV-2 (D4)
* SARS-CoV-2 (D7)
* BCG-STING (Tice) + SARS-CoV-2 (D7)
All P values from Student's t-test
b. CD4+ T cells (lungs)
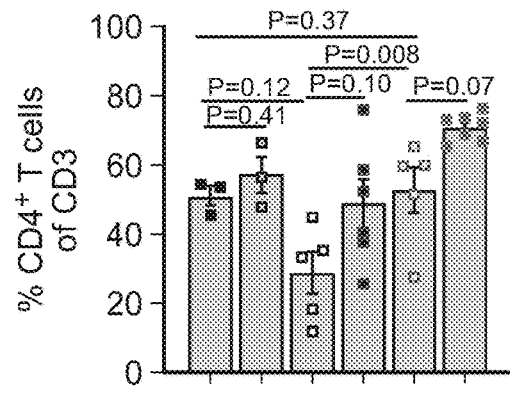
c.    Macrophages (lungs)
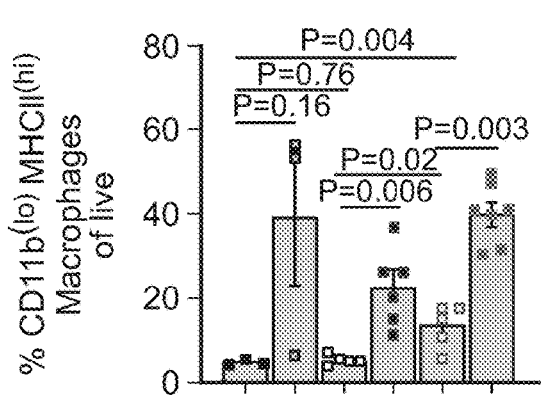
d. Granulocytes (lungs)
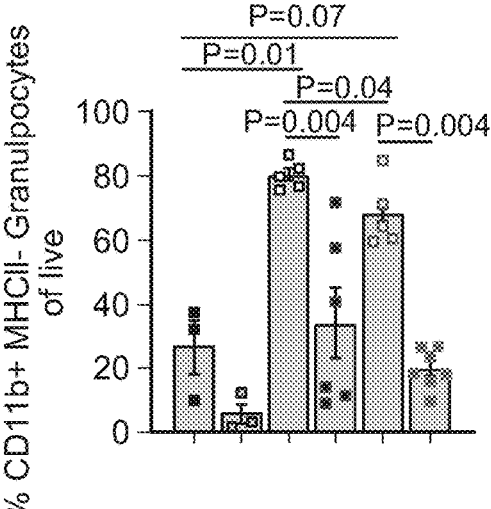
FIGURES 5A-D

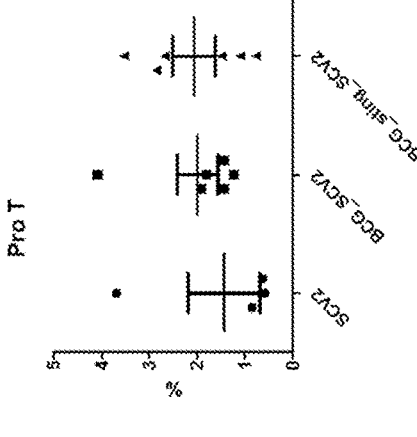
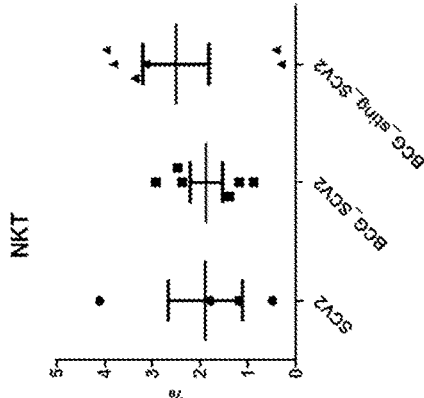
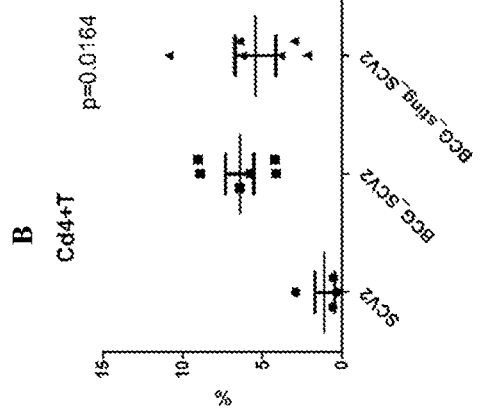
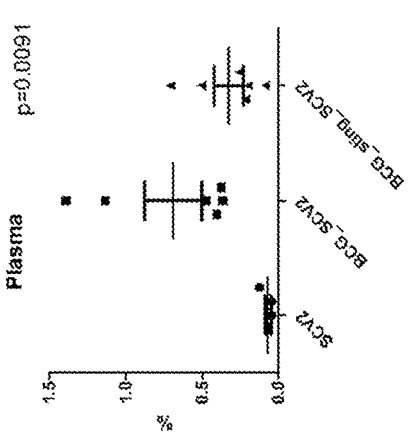
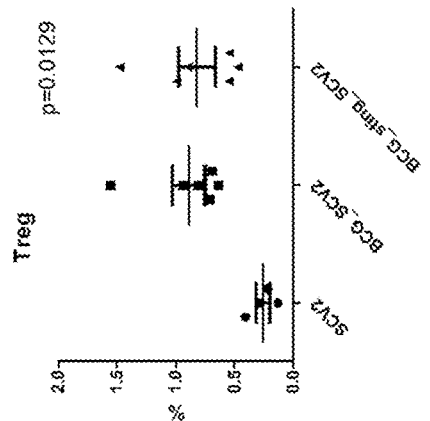
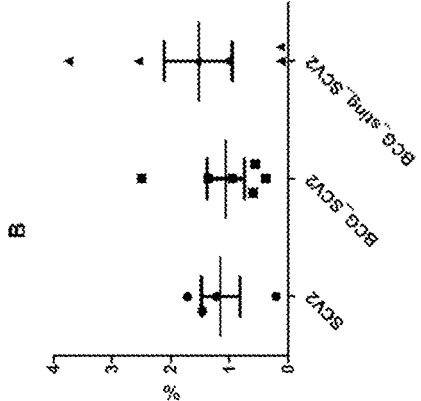
FIGURE 7B

C

Plasma cell immunoglobulin production
Gene signature score
(d4 + d 7 combined)

Immunoglobulin production

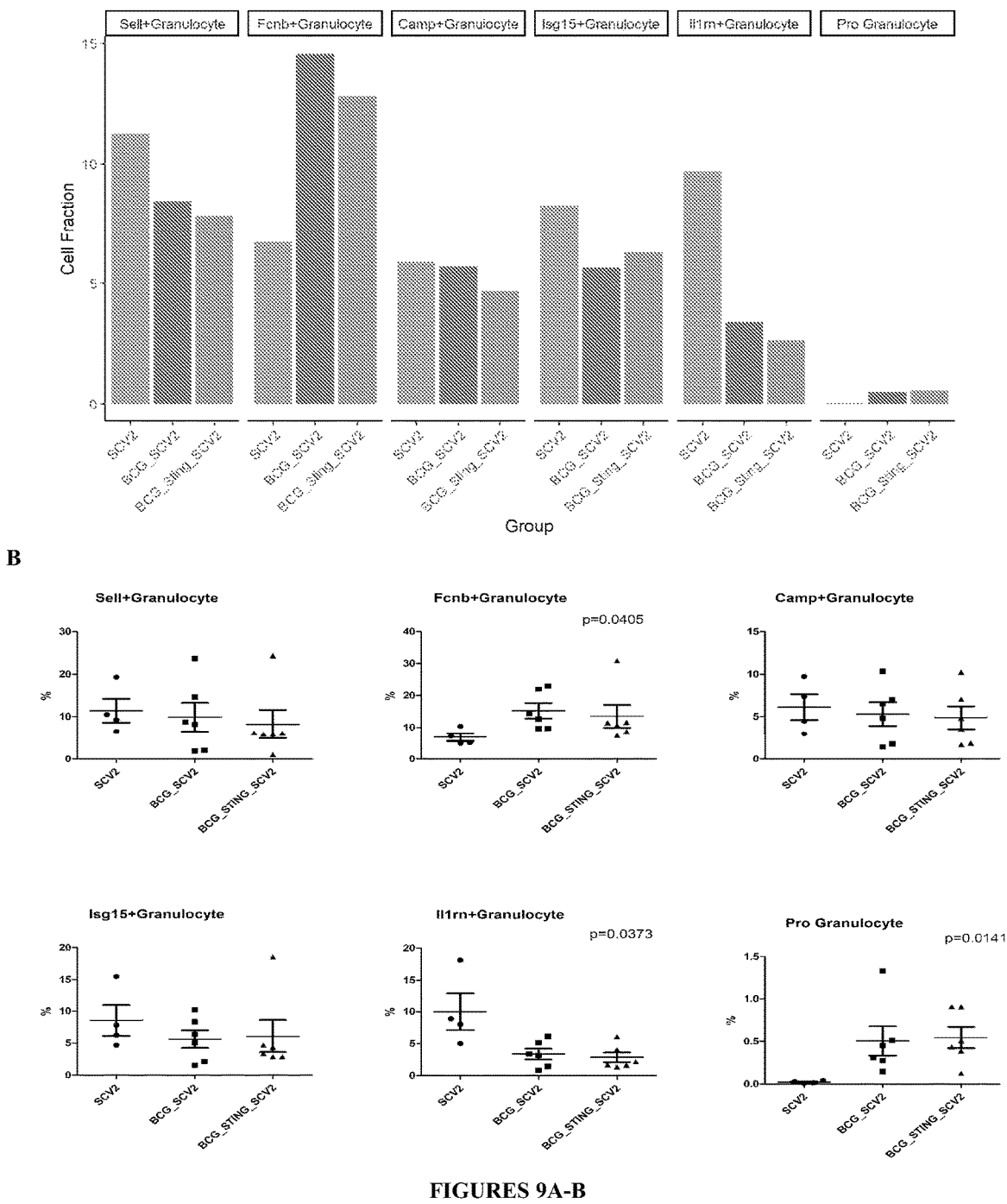
FIGURES 9A-B

A

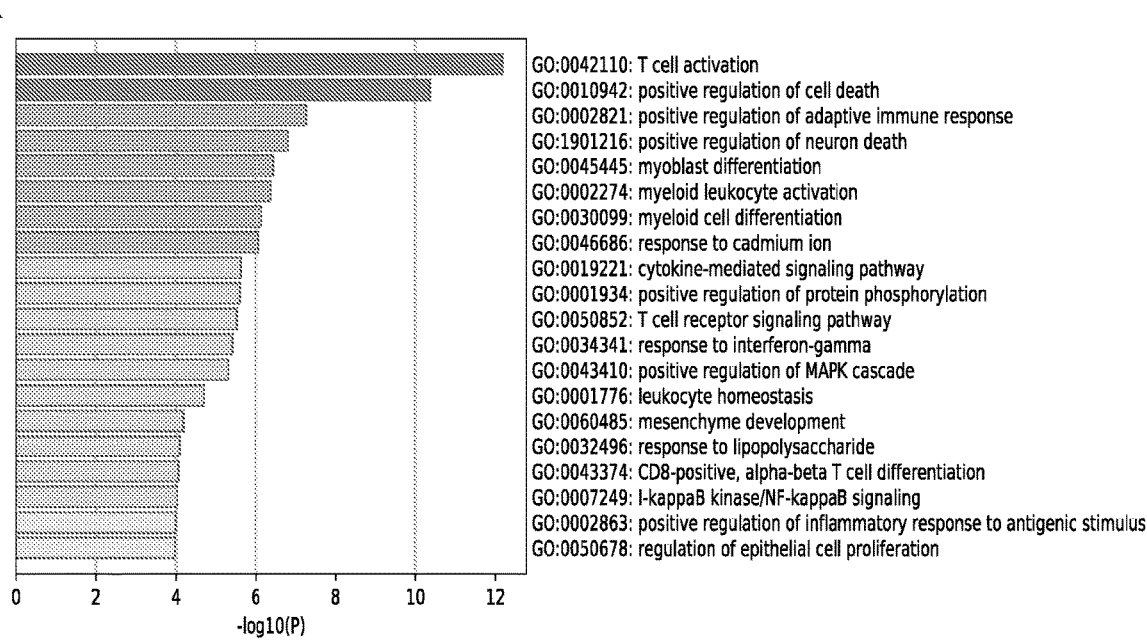

GO:0042110: T cell activation
GO:0010942: positive regulation of cell death
GO:0002821: positive regulation of adaptive immune response
GO:1901216: positive regulation of neuron death
GO:0045445: myoblast differentiation
GO:0002274: myeloid leukocyte activation
GO:0030099: myeloid cell differentiation
GO:0046686: response to cadmium ion
GO:0019221: cytokine-mediated signaling pathway
GO:0001934: positive regulation of protein phosphorylation
GO:0050852: T cell receptor signaling pathway
GO:0034341: response to interferon-gamma
GO:0043410: positive regulation of MAPK cascade
GO:0001776: leukocyte homeostasis
GO:0060485: mesenchyme development
GO:0032496: response to lipopolysaccharide
GO:0043374: CD8-positive, alpha-beta T cell differentiation
GO:0007249: I-kappaB kinase/NF-kappaB signaling
GO:0002863: positive regulation of inflammatory response to antigenic stimulus
GO:0050678: regulation of epithelial cell proliferation

B

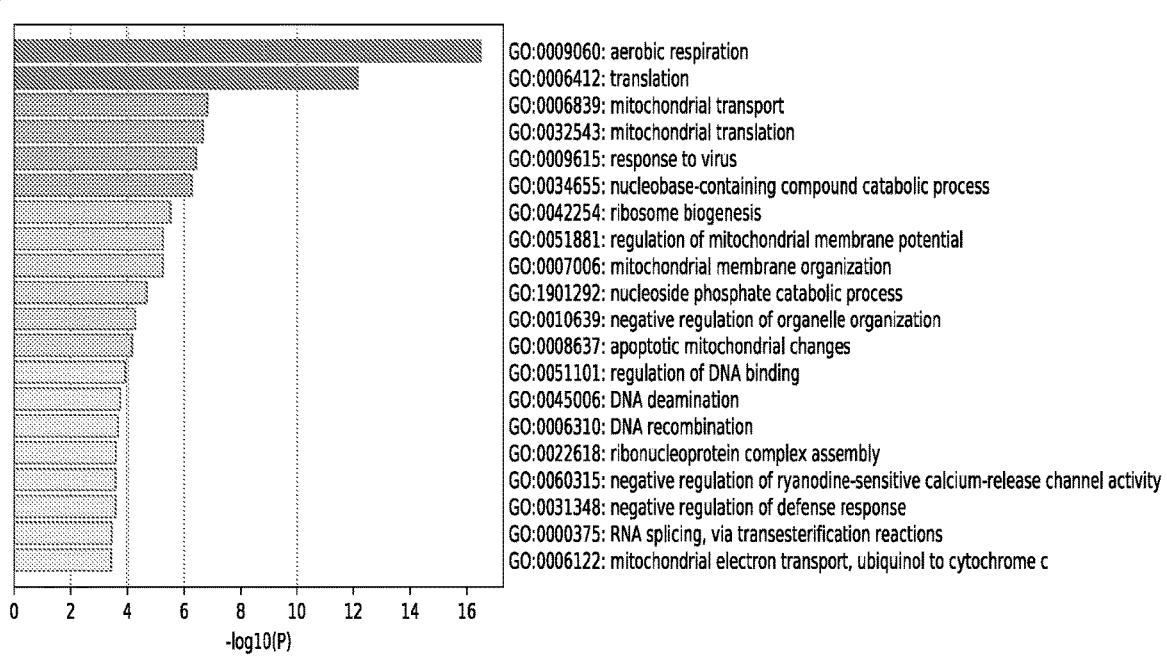

GO:0009060: aerobic respiration
GO:0006412: translation
GO:0006839: mitochondrial transport
GO:0032543: mitochondrial translation
GO:0009615: response to virus
GO:0034655: nucleobase-containing compound catabolic process
GO:0042254: ribosome biogenesis
GO:0051881: regulation of mitochondrial membrane potential
GO:0007006: mitochondrial membrane organization
GO:1901292: nucleoside phosphate catabolic process
GO:0010639: negative regulation of organelle organization
GO:0008637: apoptotic mitochondrial changes
GO:0051101: regulation of DNA binding
GO:0045006: DNA deamination
GO:0006310: DNA recombination
GO:0022618: ribonucleoprotein complex assembly
GO:0060315: negative regulation of ryanodine-sensitive calcium-release channel activity
GO:0031348: negative regulation of defense response
GO:0000375: RNA splicing, via transesterification reactions
GO:0006122: mitochondrial electron transport, ubiquinol to cytochrome c

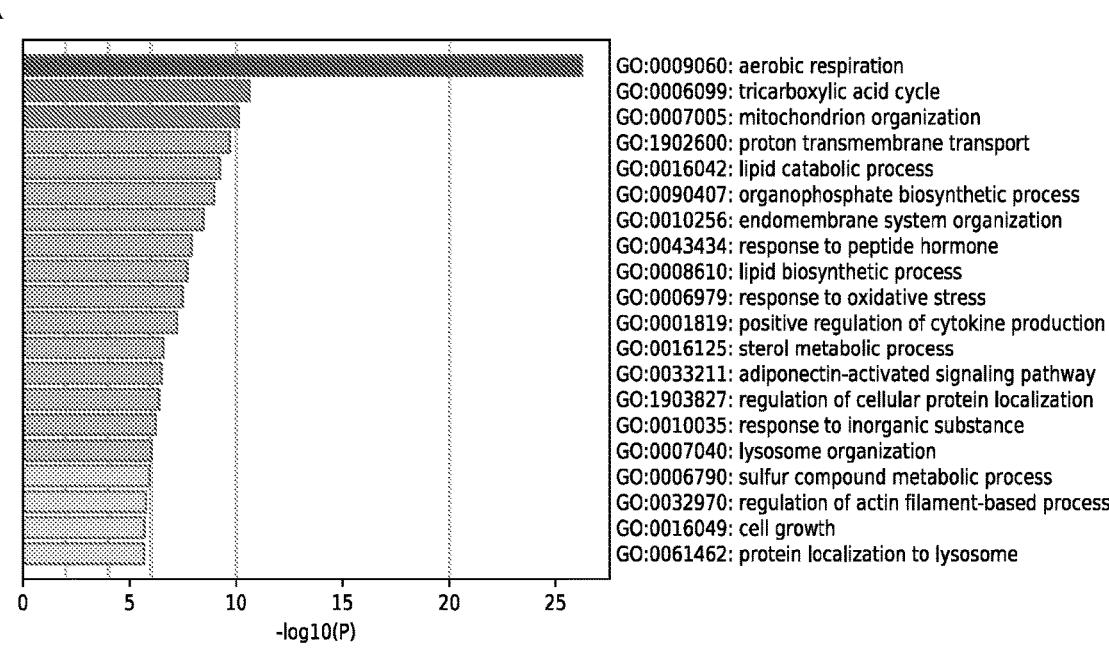

GO:0009060: aerobic respiration
GO:0006099: tricarboxylic acid cycle
GO:0007005: mitochondrion organization
GO:1902600: proton transmembrane transport
GO:0016042: lipid catabolic process
GO:0090407: organophosphate biosynthetic process
GO:0010256: endomembrane system organization
GO:0043434: response to peptide hormone
GO:0008610: lipid biosynthetic process
GO:0006979: response to oxidative stress
GO:0001819: positive regulation of cytokine production
GO:0016125: sterol metabolic process
GO:0033211: adiponectin-activated signaling pathway
GO:1903827: regulation of cellular protein localization
GO:0010035: response to inorganic substance
GO:0007040: lysosome organization
GO:0006790: sulfur compound metabolic process
GO:0032970: regulation of actin filament-based process
GO:0016049: cell growth
GO:0061462: protein localization to lysosome -log10(P)

B

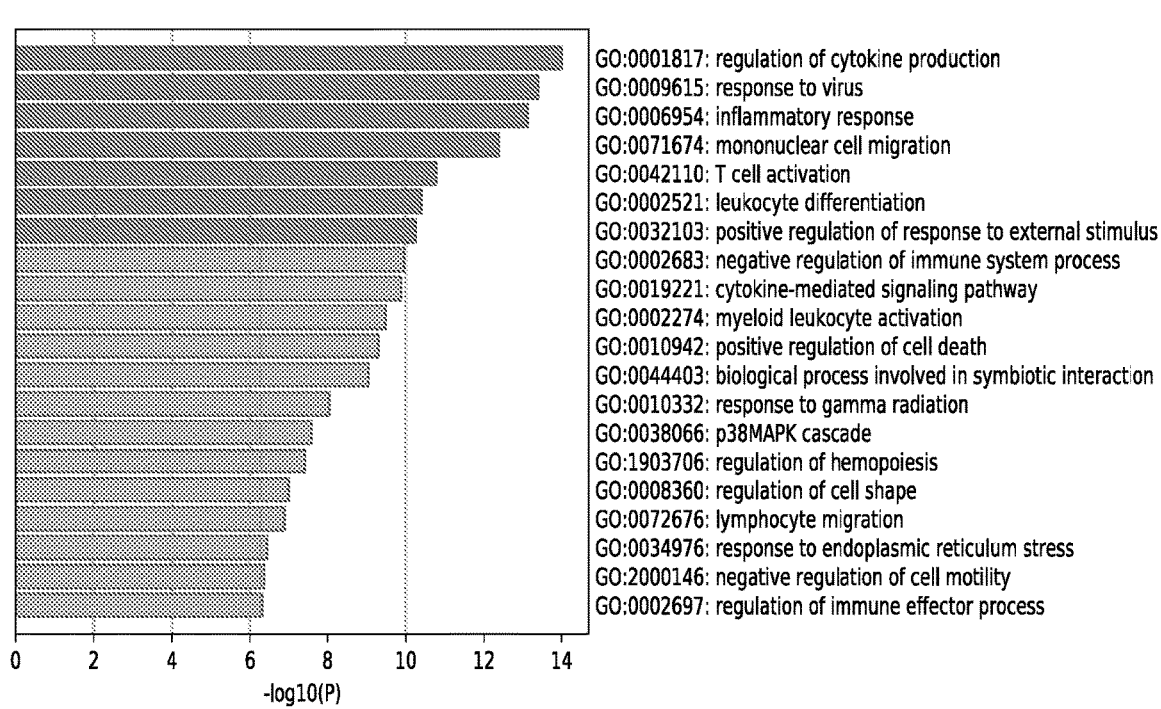

GO:0001817: regulation of cytokine production
GO:0009615: response to virus
GO:0006954: inflammatory response
GO:0071674: mononuclear cell migration
GO:0042110: T cell activation
GO:0002521: leukocyte differentiation
GO:0032103: positive regulation of response to external stimulus
GO:0002683: negative regulation of immune system process
GO:0019221: cytokine-mediated signaling pathway
GO:0002274: myeloid leukocyte activation
GO:0010942: positive regulation of cell death
GO:0044403: biological process involved in symbiotic interaction
GO:0010332: response to gamma radiation
GO:0038066: p38MAPK cascade
GO:1903706: regulation of hemopoiesis
GO:0008360: regulation of cell shape
GO:0072676: lymphocyte migration
GO:0034976: response to endoplasmic reticulum stress
GO:2000146: negative regulation of cell motility
GO:0002697: regulation of immune effector process -log10(P)

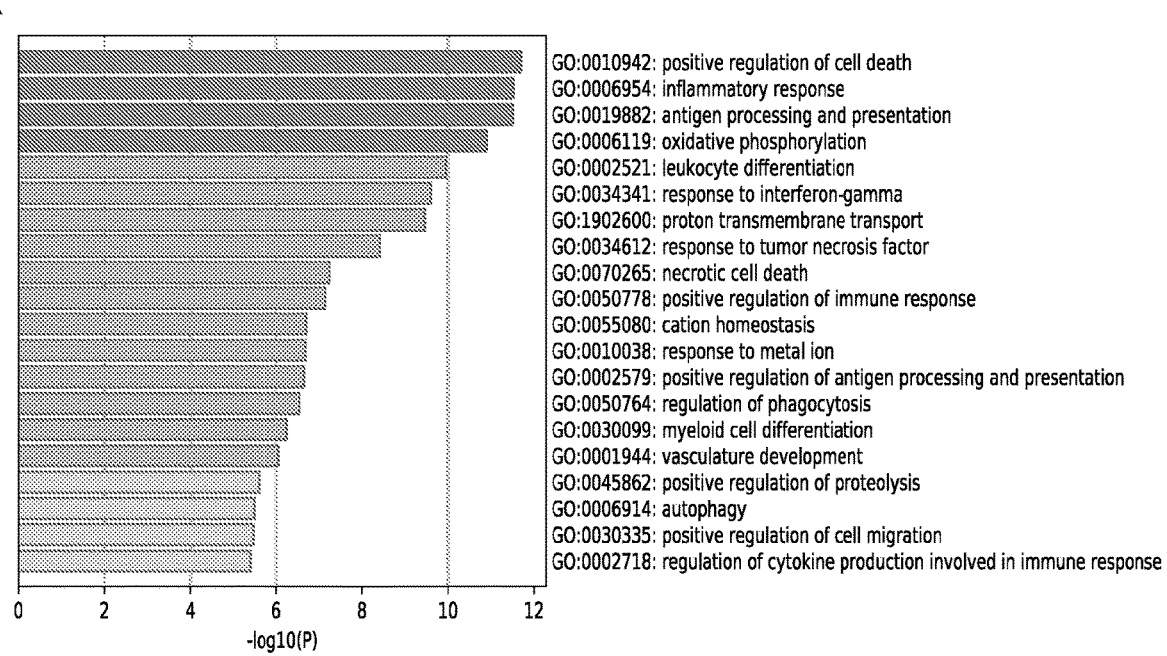

GO:0010942: positive regulation of cell death
GO:0006954: inflammatory response
GO:0019882: antigen processing and presentation
GO:0006119: oxidative phosphorylation
GO:0002521: leukocyte differentiation
GO:0034341: response to interferon-gamma
GO:1902600: proton transmembrane transport
GO:0034612: response to tumor necrosis factor
GO:0070265: necrotic cell death
GO:0050778: positive regulation of immune response
GO:0055080: cation homeostasis
GO:0010038: response to metal ion
GO:0002579: positive regulation of antigen processing and presentation
GO:0050764: regulation of phagocytosis
GO:0030099: myeloid cell differentiation
GO:0001944: vasculature development
GO:0045862: positive regulation of proteolysis
GO:0006914: autophagy
GO:0030335: positive regulation of cell migration
GO:0002718: regulation of cytokine production involved in immune response -log10(P)

B

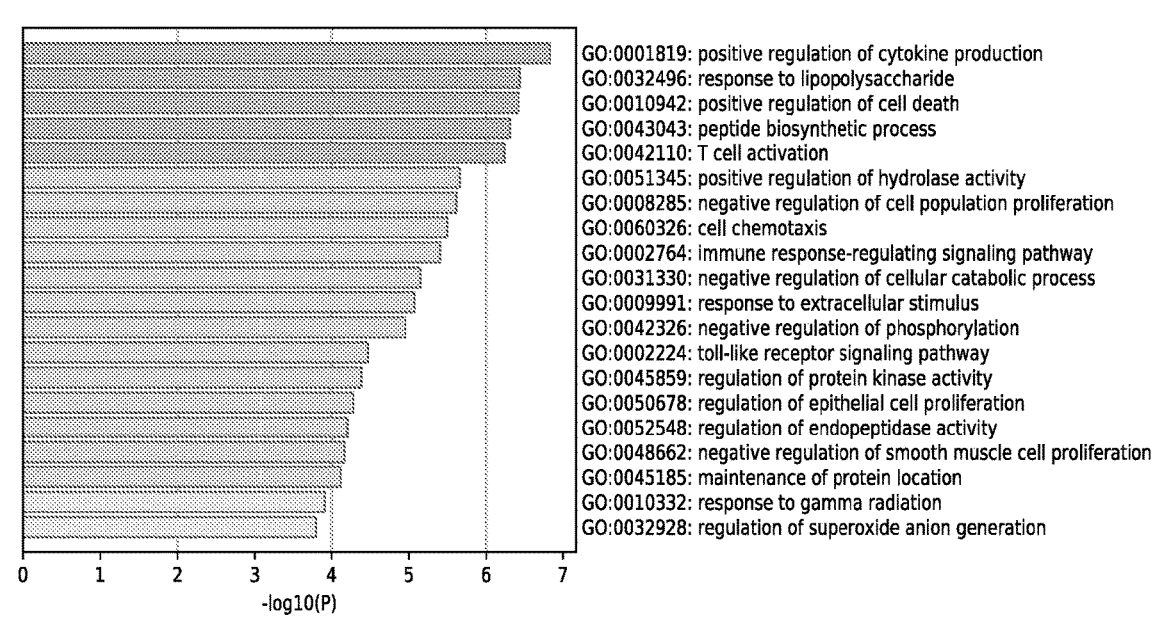

GO:0001819: positive regulation of cytokine production
GO:0032496: response to lipopolysaccharide
GO:0010942: positive regulation of cell death
GO:0043043: peptide biosynthetic process
GO:0042110: T cell activation
GO:0051345: positive regulation of hydrolase activity
GO:0008285: negative regulation of cell population proliferation
GO:0060326: cell chemotaxis
GO:0002764: immune response-regulating signaling pathway
GO:0031330: negative regulation of cellular catabolic process
GO:0009991: response to extracellular stimulus
GO:0042326: negative regulation of phosphorylation
GO:0002224: toll-like receptor signaling pathway
GO:0045859: regulation of protein kinase activity
GO:0050678: regulation of epithelial cell proliferation
GO:0052548: regulation of endopeptidase activity
GO:0048662: negative regulation of smooth muscle cell proliferation
GO:0045185: maintenance of protein location
GO:0010332: response to gamma radiation
GO:0032928: regulation of superoxide anion generation -log10(P)

FIGURES 12A-B

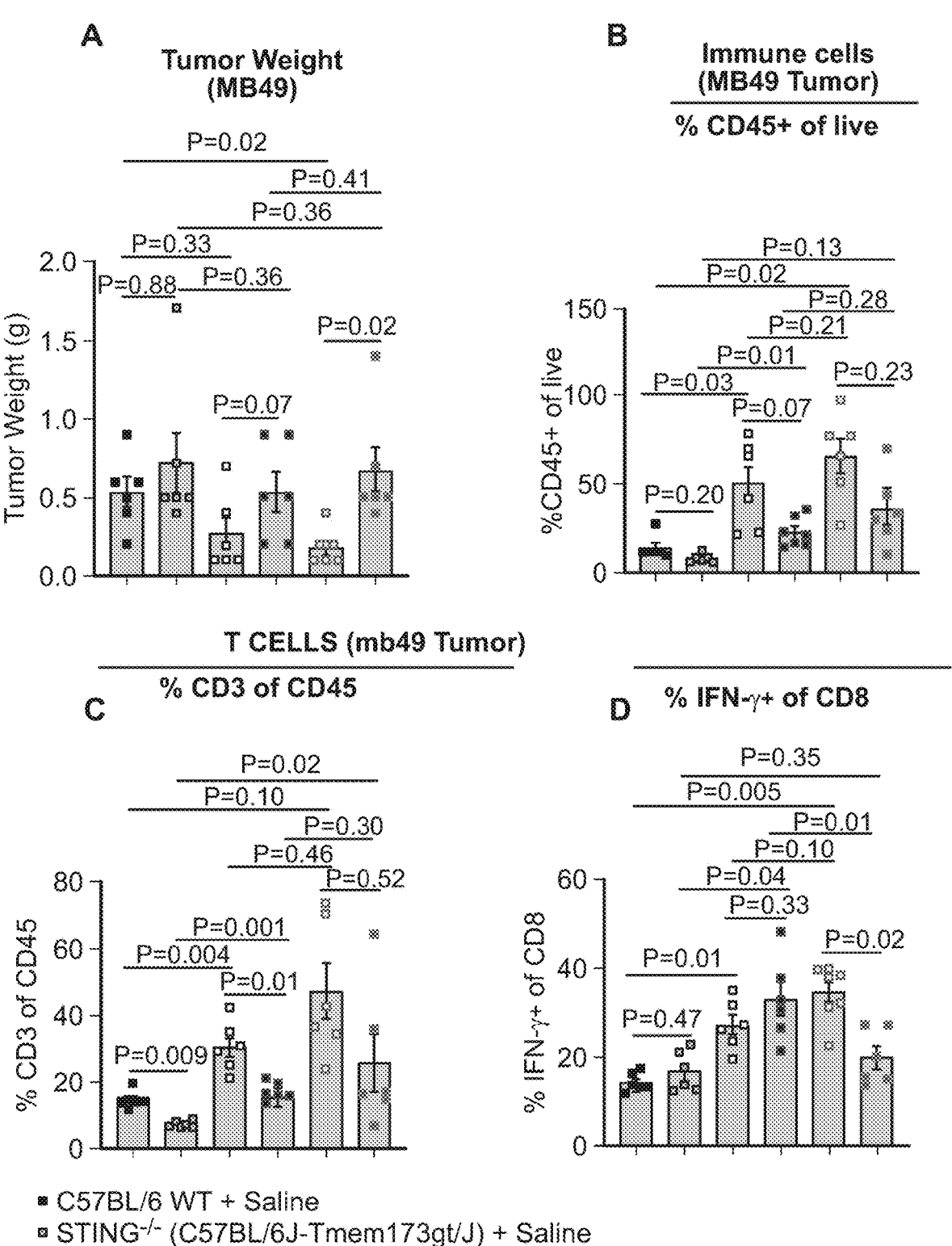
● C57BL/6 WT + Saline
◻ STING⁻/⁻ (C57BL/6J-Tmem173gt/J) + Saline
▫ C57BL/6 WT + BCG-WT (Tice)
✻ STING⁻/⁻ (C57BL/6J-Tmem173gt/J) + BCG-WT (Tice)
◻ C57BL6 + BCG-disA-OE (Tice)
✻ STING⁻/⁻ (C57BL/6J-Tmem173gt/J) + BCG-disA-OE (Tice)
FIGURES 13A-D T cells (MB49 Tumor)
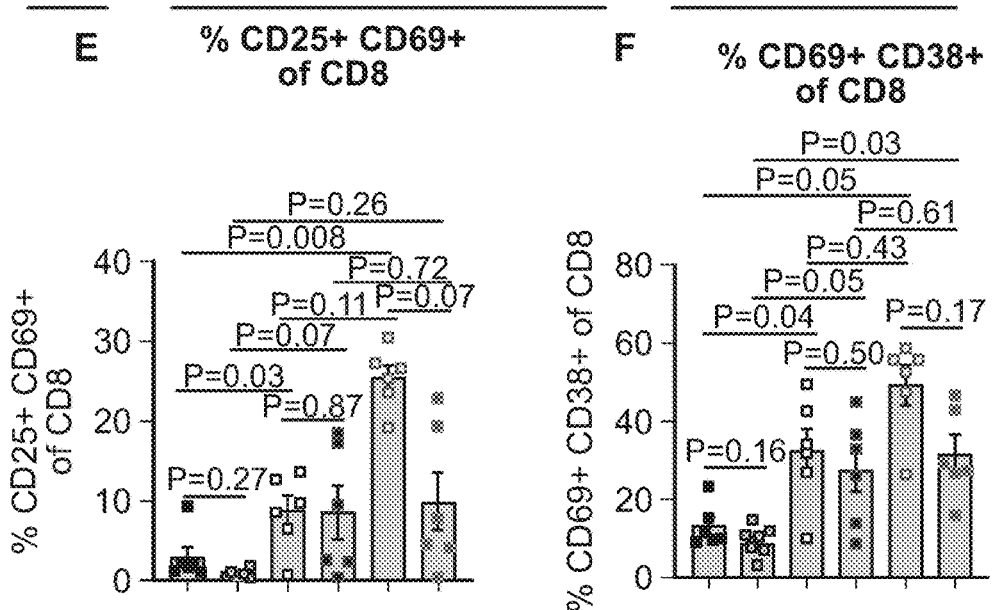
Macrophages (MB49 Tumor)
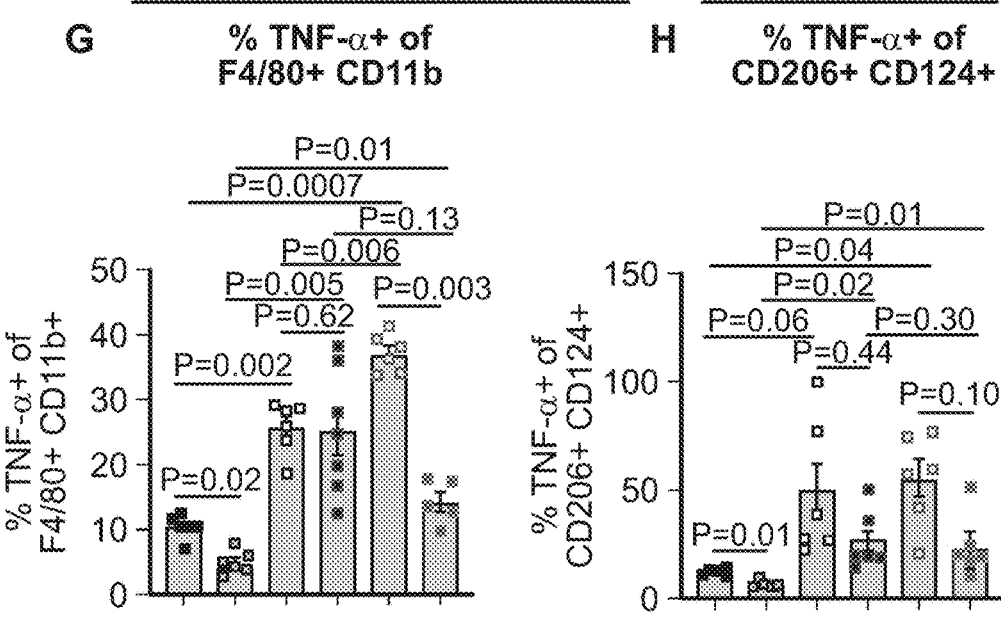
■ C57BL/6 WT + Saline
◻ STING⁻ᐟ⁻ (C57BL/6J-Tmem173gt/J) + Saline
◻ C57BL/6 WT + BCG-WT (Tice)
▨ STING⁻ᐟ⁻ (C57BL/6J-Tmem173gt/J) + BCG-WT (Tice)
▨ C57BL6 + BCG-*disA*-OE (Tice)
▨ STING⁻ᐟ⁻ (C57BL/6J-Tmem173gt/J) + BCG-*disA*-OE (Tice)
FIGURES 13E-H

(a)
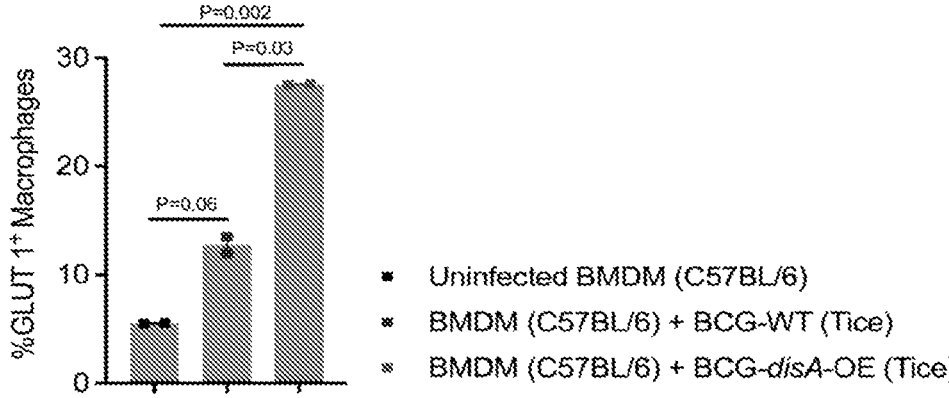
(b)
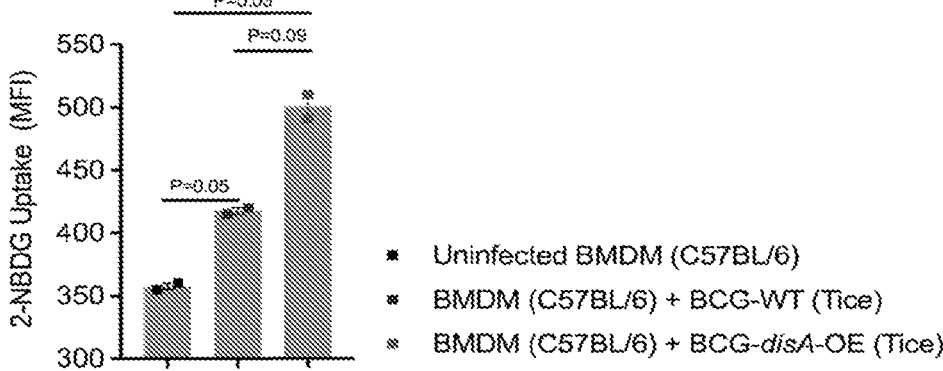
FIGURES 15A-B

A
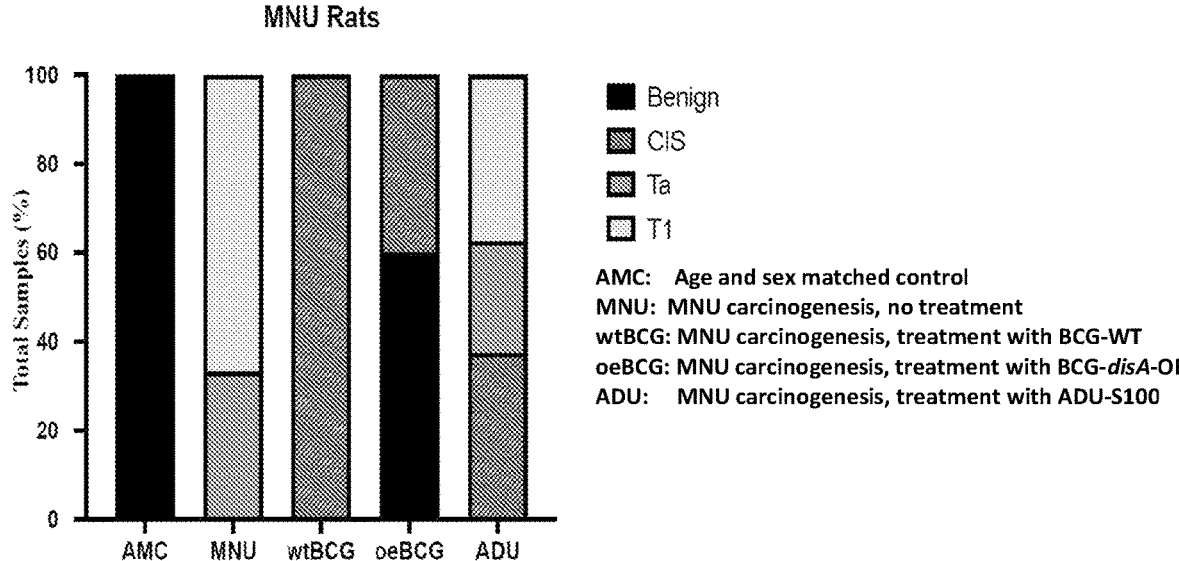
ADU-S100:
Aduro's small
molecule
STING agonist
STING Activator (Agonist)
Clinical-stage, Water Soluble
B
MNU Rats
AMC:   Age and sex matched control
MNU:  MNU carcinogenesis, no treatment
wtBCG: MNU carcinogenesis, treatment with BCG-WT
oeBCG: MNU carcinogenesis, treatment with BCG-*disA*-OE
ADU:   MNU carcinogenesis, treatment with ADU-S100
FIGURES 16A-B

A
Bronchopneumonia
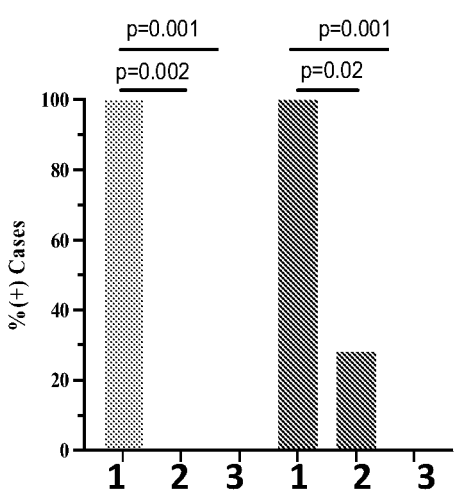
B
Neutrophil Infiltration
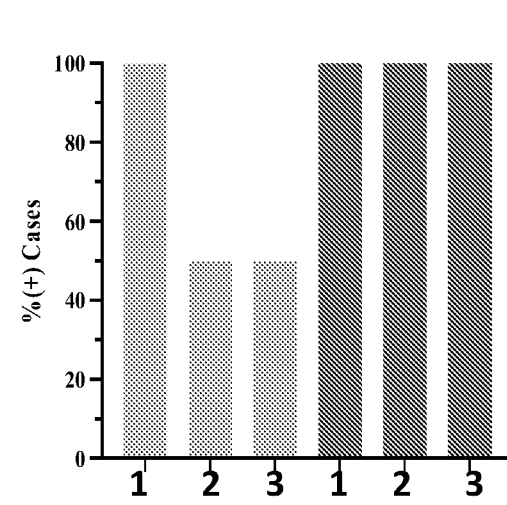
C
Macrophage Infiltration
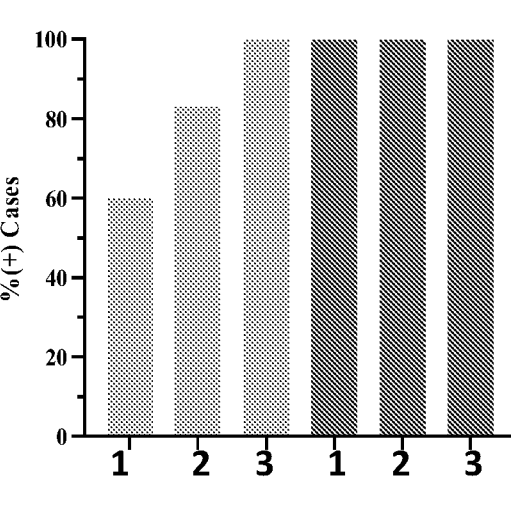
D
Interstitial Inflammation
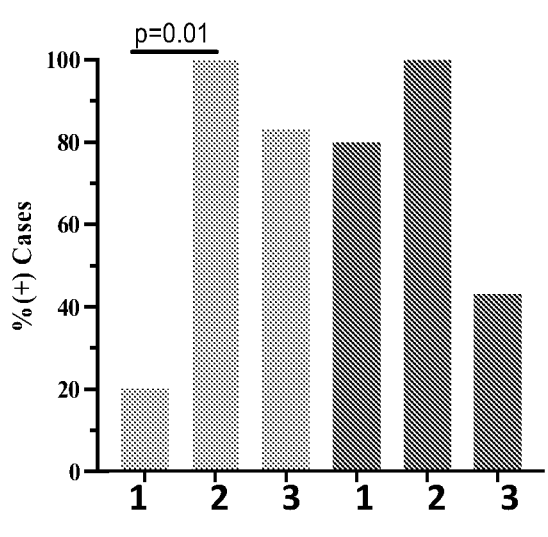
▒ 4dpi
▨ 7dpi
1. SCV2 only
2. BCG-WT & SCV2
3. BCG-STING & SCV2
FIGURES 18A-D

E
F
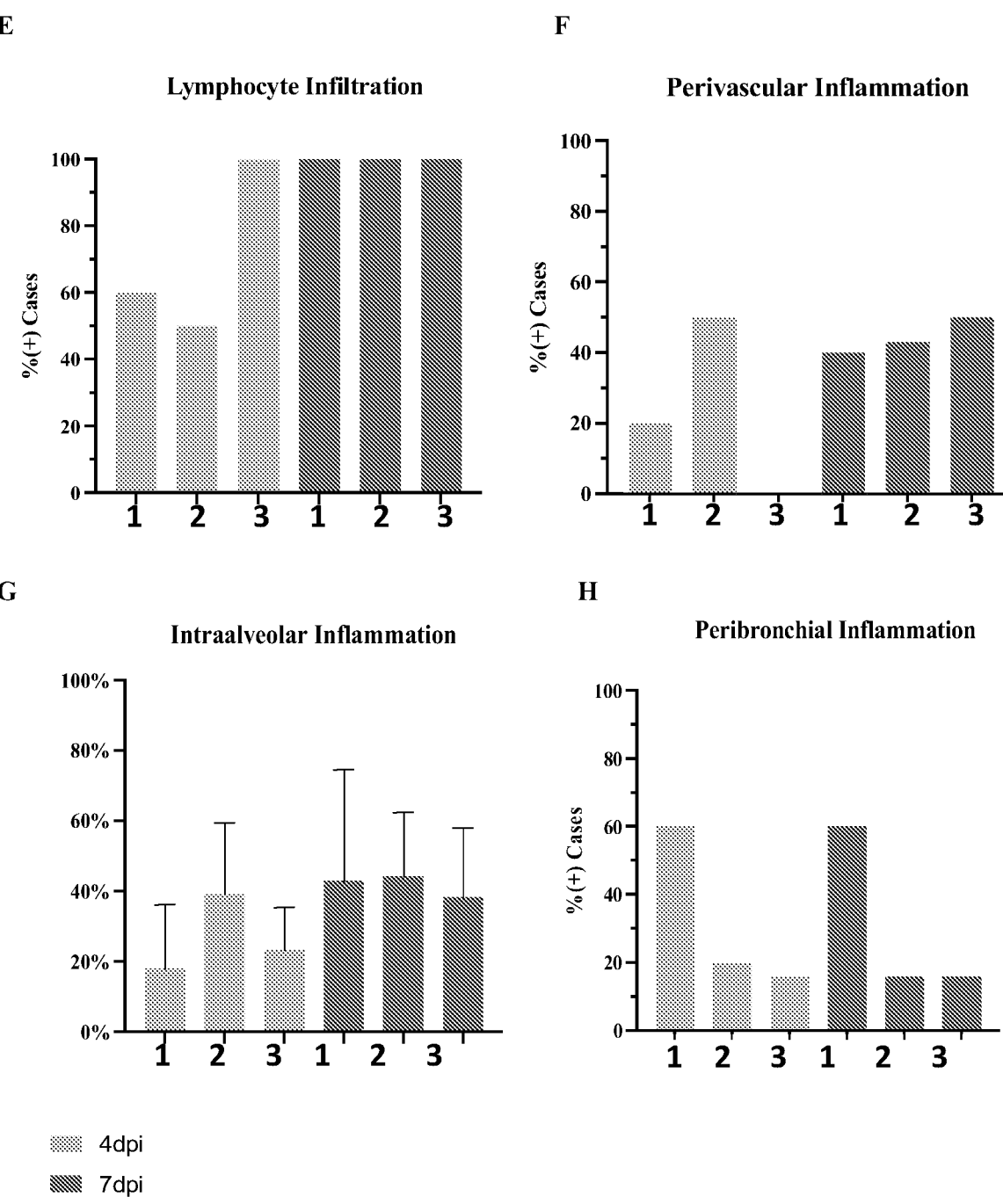
G
H
1. SCV2 only
2. BCG-WT & SCV2
3. BCG-STING & SCV2
FIGURES 18E-H

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttacaaacat tggccgcaaa                                        20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcgcgacatt ccgaagaa                                          18

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
acaatttgcc cccagcgctt cag                                    23

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agatttggac ctgcgagcg                                         19

<210> SEQ ID NO 5
<211> LENGTH: 20
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 5
gagcggctgt ctccacaagt                                                  20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ttctgacctg aaggctctgc gcg                                              23

<210> SEQ ID NO 7
<211> LENGTH: 4
<212> TYPE: PRT
<213> ORGANISM: Severe acute respiratory syndrome coronavirus 2

<400> SEQUENCE: 7

Arg Arg Ala Arg
1
```

BCG BASED VACCINE COMPOSITIONS AND METHODS OF USE THEREOF

CROSS-REFERENCE TO RELATED APPLICATIONS

This application is a 35 USC § 371 National Stage application of International Application No. PCT/US2021/053234 filed Oct. 1, 2021, which claims the benefit under 35 USC § 119 (e) to U.S. Application Ser. No. 63/086,559 filed Oct. 1, 2020, now expired. The disclosure of each of the prior applications is considered part of and is incorporated by reference in the disclosure of this application.

GOVERNMENT SUPPORT STATEMENT

This invention was made with government support under grants R01A155346, AI155346 and AI037856 awarded by the National Institutes of Health. The government has certain rights in the invention.

INCORPORATION BY REFERENCE OF SEQUENCE LISTING

The material in the accompanying sequence listing is hereby incorporated by reference into this application. The accompanying sequence listing text file, named JHU4220-1_ST25.txt, was created on Mar. 30, 2023 and is 2 kB in size. The file can be accessed using Microsoft Word on a computer that uses Windows OS.

BACKGROUND OF THE INVENTION

Field of the Invention

The invention relates generally to vaccines and more specifically to a BCG-based vaccine for the prevention of viral infections.

Background Information

The on-going Covid-19 pandemic caused by SARS-CoV-2 has affected nearly 32 million individuals worldwide, leading to over a million deaths, with a devastating impact on global health and economy. Uncontrolled production of pro-inflammatory mediators in vulnerable individuals in response to the virus is believed to contribute to acute respiratory distress syndrome and cytokine storm syndrome leading to fatal disease. Although a few antiviral agents, immune modulating treatments, and vaccines are currently in trials, therapeutics and/or vaccines that are already approved, if effective and rapidly deployed, offer the potential to save thousands of lives and prevent even higher levels of morbidity and economic hardship. The pandemic has renewed interest in Bacillus Calmette—Guérin (BCG), an attenuated strain of *Mycobacterium bovis,* one of the most widely used vaccines in the prevention of tuberculous meningitis and disseminated tuberculosis, and as an adjuvant immunotherapy for patients with non-muscle-invasive bladder cancer (NMIBC). BCG vaccination has been shown to confer resistance to heterologous infections, including yellow fever, HPV, RSV, Influenza A, and HSV in humans. This protective effect is attributed to epigenetic reprogramming of innate immune cells called trained immunity leading to long-term changes in their ability to actively respond to novel stimuli. Based on these observations clinical trials of BCG for COVID-19 prevention have been initiated. While these ongoing clinical trials are exciting, their impact may be limited by the timing and disease incidence at the respective trial sites, as well as by the difficulty of enrolling sufficient patient numbers. Concerns have also been raised regarding the possibility that an excessive inflammatory response induced by BCG in some patients with COVID-19 might aggravate disease. Pre-clinical studies using animal studies with BCG are therefore critically needed to ensure safety and efficacy of BCG in SARS-CoV-2 infection.

Recent studies also highlight the fact that during COVID-19 disease there is a blunted and delayed anti-viral Type I interferon (IFN) response induced by the virus, contributing to the immunopathogenesis of the disease. Early administration of Type I IFN is therefore considered protective.

SUMMARY OF THE INVENTION

The present invention relates to a BCG based vaccine using a BCG strain that overexpresses the STING agonist, c-di-AMP designated BCG-disA-OE or BCG-STING. The invention further relates to the use of BCG-disA-OE for the prevention, amelioration or treatment of viral infections, such as primary respiratory infections and SARS-CoV-2.

In one embodiment, the present invention provides a recombinant bacille Calmette-Guerin (BCG) bacterial strain having a disA gene, wherein the bacterial strain is optionally resistant to kanamycin. In one aspect, the bacterial strain over expresses a stimulator of interferon genes (STING) agonist. In certain aspects, the STING agonist is c-di-AMP. In some aspects, the disA gene is a *M. tuberculosis* disA gene. In an additional aspect, the disA gene is fused to a mycobacterial promoter. In a further aspect, the mycobacterial promoter is $P_{HSP60}$. In one aspect, the nucleic acid sequence of the bacterial strain does not have kanamycin resistance markers. In an additional aspect the strain further comprises a selectable marker. In certain aspects, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.

In one embodiment the present invention provides, a pharmaceutical composition having a recombinant bacille Calmette-Guerin (BCG) bacterial strain having a disA gene and a pharmaceutically acceptable carrier, wherein the bacterial strain is optionally resistant to kanamycin. In one aspect, the bacterial strain over expresses c-di-AMP. In an additional aspect, the disA gene is fused to a mycobacterial promoter. In a further aspect, the pharmaceutically acceptable carrier is phosphate buffer; citrate buffer; ascorbic acid; methionine; octadecyldimethylbenzyl ammonium chloride; hexamethonium chloride; benzalkonium chloride; benzethonium chloride; phenol alcohol; butyl alcohol; benzyl alcohol; methyl paraben; propyl paraben; catechol; resorcinol; cyclohexanol; 3-pentanol; m-cresol; low molecular weight (less than about 10 residues) polypeptides; serum albumin; gelatin; immunoglobulins; polyvinylpyrrolidone glycine; glutamine; asparagine; histidine; arginine; lysine; monosaccharides; disaccharides; glucose; mannose; dextrins; EDTA; sucrose; mannitol; trehalose; sorbitol; sodium; saline; metal surfactants; non-ionic surfactants; polyethylene glycol (PEG); magnesium stearate; water; alcohol; saline solution; glycol; mineral oil or dimethyl sulfoxide (DMSO). In one aspect, the nucleic acid sequence of the bacterial strain does not have kanamycin resistance markers. In certain aspects, when present, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.

In an additional embodiment, the present invention provides a method of preventing, ameliorating or treating primary a viral infection in a subject by administering a recombinant bacille Calmette-Guerin (BCG) bacterial strain having a disA gene, thereby treating the infection. In one aspect, the viral infection is a primary respiratory infection. In certain aspects, the viral infection is a non-tuberculosis mycobacteria infection or a SARS-CoV-2 infection. In an additional aspect, the subject has a condition selected from the group consisting of obesity, diabetes, cystic fibrosis (CF), non-cystic-fibrosis bronchiectasis, and HIV/AIDS. In a further aspect, the bacterial strain over expresses a stimulator of interferon genes (STING) agonist. In a specific aspect, the STING agonist is c-di-AMP. In one aspect, the disA gene is fused to a mycobacterial promoter. In an additional aspect, the nucleic acid sequence of the bacterial strain does not have kanamycin resistance markers. In a further aspect, the bacterial strain is optionally resistant to kanamycin. In an additional aspect the strain further comprises a selectable marker. In certain aspects, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.

In one embodiment, the present invention provides a method of preventing, ameliorating or treating a bacterial infection in a subject by administering a recombinant bacille Calmette-Guerin (BCG) bacterial strain having a disA gene, thereby treating the infection. In one aspect, the bacterial infection is a primary respiratory infection. In certain aspects, the infection is a non-tuberculosis mycobacteria infection. In an additional aspect, the subject has cystic fibrosis (CF). In a further aspect, the bacterial strain over expresses a stimulator of interferon genes (STING) agonist. In certain aspects, the STING agonist is c-di-AMP. In one aspect, the disA gene is fused to a mycobacterial promoter. In an additional aspect, the nucleic acid sequence of the bacterial strain does not have kanamycin resistance markers. In a further aspect, the bacterial strain is optionally resistant to kanamycin. In an additional aspect the strain further comprises a selectable marker. In certain aspects, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.

In a further embodiment, the present invention provides a method of regulating glucose levels in a subject by administering a recombinant bacille Calmette-Guerin (BCG) bacterial strain having a disA gene, thereby regulating glucose levels. In one aspect, the glucose levels are increased after administration of the BCG bacterial strain. In an additional aspect, the glucose levels are decreased after administration of the BCG bacterial strain. In a further aspect, the bacterial strain over expresses a stimulator of interferon genes (STING) agonist. In certain aspects, the STING agonist is c-di-AMP. In an additional aspect, the nucleic acid sequence of the bacterial strain does not have kanamycin resistance markers. In a further aspect, the bacterial strain is optionally resistant to kanamycin. In an additional aspect the strain further comprises a selectable marker. In certain aspects, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.In one embodiment, the present invention provides a method of inducing an immunological response in a subject suffering from a viral infection by administering a recombinant bacille Calmette-Guerin (BCG) bacterial strain having a disA gene, thereby inducing an immunological response. In one aspect, the administration of the BCG bacterial strain causes an increase in lung alveolar macrophages, the prevention of SCV2-mediated T cell lymphopenia, the prevention of granulocyte lung infiltration, an increase immunoglobulin-producing plasma cells in the lung, and/or an increase in Treg cells in the lung. In an additional aspect, the bacterial strain over expresses a stimulator of interferon genes (STING) agonist. In certain aspects, the STING agonist is c-di-AMP. In an additional aspect, the nucleic acid sequence of the bacterial strain does not have kanamycin resistance markers. In a further aspect, the bacterial strain is optionally resistant to kanamycin. In an additional aspect the strain further comprises a selectable marker In certain aspects, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.

In one embodiment, the present invention provides a nucleic acid construct with a promoter sequence; an M. tuberculosis disA sequence; a signal peptide; and a receptor binding domain of the spike protein of SARS-CoV-2 or antigenic fragments thereof, in operable order. In one aspect, the promoter sequence is an Hsp60 promoter.

In an additional embodiment, the present invention provides the use of the nucleic acid construct for administration to a subject having or at risk of having a SARS-CoV-2 infection. In one aspect, the subject is additionally administered of type I interferon.

In a further embodiment, the present invention provides a pharmaceutical composition containing the nucleic acid construct.

In one embodiment, the present invention, provides a method of inducing an immune response to SARS-CoV-2 in a subject having or at risk of having a SARS-CoV-2 infection, including administering the pharmaceutical composition containing the nucleic acid construct. In one aspect, administration is by intravenous injection. In an additional aspect, the subject is a human.

In an additional embodiment, the present invention provides a method for preventing, ameliorating or treating primary a viral infection by administering to a subject in need thereof a pharmaceutical composition with a nucleic acid construct, wherein the nucleic acid construct has a promoter sequence; an M. tuberculosis disA sequence; and a signal peptide, in operable order. In one aspect, the viral infection is a primary respiratory infection. In certain aspects, the subject is elderly, a healthy adult or an infant or child that is not at risk for tuberculosis. In an additional aspect, the subject has a condition selected from the group consisting of obesity, diabetes, cystic fibrosis (CF), non-cystic-fibrosis bronchiectasis, and HIV/AIDS. In one aspect, the subject is immunosuppressed due to chronic use of an immunosuppressive therapy, malignancy, radiation therapy, bone marrow transplant, or chemotherapy. In certain aspects, the immunosuppressive therapy is a steroid or an anti-TNF agent. In a further aspect. the subject is subject to an environment at high risk for exposure to the viral infection. In various aspects, the environment is a health care or health care related facility, a prison or a nursing home. In one aspect, the nucleic acid construct further comprises a viral protein or antigenic fragment thereof In a further embodiment, the present invention provides a method for managing blood glucose in a subject having diabetes by administering a nucleic acid construct to the subject, wherein the nucleic acid construct has a promoter sequence; an M. tuberculosis disA sequence; and a signal peptide, in operable order.

In one embodiment, the present invention provides a nucleic acid construct having a promoter sequence; an M. tuberculosis disA sequence; a ppiA signal sequence; a spike protein of SARS-CoV-2 or the receptor binding domain of the spike protein of SARS-CoV-2; and a signal peptide, in operable order.

In an additional embodiment, the present invention provides a nucleic acid construct having a promoter sequence; an M. tuberculosis disA sequence; a ppiA sequence; and a signal peptide, in operable order. In one aspect, the nucleic acid construct may also have a ppiA signal sequence.

In one aspect, the nucleic acid construct includes a viral protein or antigenic fragment thereof.

In an additional aspect, the viral protein or antigenic fragment thereof is a spike protein of SARS-CoV-2 or the receptor binding domain of the spike protein of SARS-CoV-2.

In one embodiment, the present invention provides a pharmaceutical composition with any of the nucleic acid constructs disclosed herein.

In a further embodiment, the present invention provides a method of inducing an immune response to a viral infection in a subject by administering to the subject the pharmaceutical composition with a nucleic construct of the invention. In one aspect, the subject has or is at risk of having a SARS-CoV-2 infection. In an additional aspect. there is an increase in levels of Type I IFN following administration of the pharmaceutical composition.

In one embodiment the present invention provides, a method for preventing a non-tuberculous mycobacterium (NTM) infection comprising administering to a subject in need thereof pharmaceutical composition comprising a nucleic acid construct, wherein the nucleic acid construct has a promoter sequence; an M. tuberculosis disA sequence; and a signal peptide, in operable order. In one aspect, the subject has cystic fibrosis (CF) or non-cystic fibrosis bronchiectasis (NCFB). In another aspect, the nucleic acid construct further comprises a bacterial protein or antigenic fragment thereof.

BRIEF DESCRIPTION OF THE DRAWINGS

FIGS. 2A-C are schematic drawing of vaccines with BCG and disA. FIG. 2A: a promoter, disA sequence, a ppiA signal sequence and a viral protein or fragment. FIG. 2B: bivalent vaccine with a promoter, disA sequence and ppiA sequence. FIG. 2C: trivalent vaccine with a promoter, disA sequence, ppiA sequence, ppiA signal sequence and a viral protein or fragment thereof.

FIGS. 3A-B show Mtb ppiA augments Type I IFNs. FIG. 3A: Raw blue ISG cells. FIG. 3B: C57BL/6 BMDMS.

FIGS. 4A-D show prevalence results of lung pathology. FIG. 4A: bronchopneumonia prevalence. FIG. 4B: Neutrophil infiltration prevalence. FIG. 4C: macrophage prevalence. FIG. 4D: granuloma prevalence.

FIGS. 5A-D show BCG vaccination blunts SCV2-mediated lung T cell lymphopenia, enhances macrophage lung recruitment, and reduces lung infiltration by granulocytes. FIG. 5A: CD3+ T cells. FIG. 5B: CD4+ cells. FIG. 5C: Macrophages. FIG. 5D: Granulocytes.

FIGS. 7A-C show cell fraction and differentially regulated genes (DEGs). FIG. 7A: relative cell fraction across 6 subsets of lymphoid cells by scRNAseq. FIG. 7B: CD4+, NKT, ProT, B, Treg, and Plasma cell fractions in each treatment group by animal. FIG. 7C: plasma cell immunoglobulin production.

FIG. 20A: relative cell fraction across 10 subsets of myeloid cells by scRNAseq. FIG. 20B: IM, Clq+AM, lsg15+IM, AM, Macro+AM, Apoe+AM, Gngt2+ IM, S100a8+IM, Pro AM, and DC cell fractions in each treatment group by animal.

FIGS. 9A-B show cell fraction and differentially regulated genes (DEGs). FIG. 24A: relative cell fraction across 6 subsets of granulocytes by scRNAseq. FIG. 24B: Self+ Granulocuye, Fcnb+Granulocyte, Camp_Granulocyte, lsg15+Granulocyte, Il1rn_Granulocyte, Pro Granulocyte cell fractions in each treatment group by animal.

FIGS. 10A-B show differentially expressed genes in CD4+ T cells. FIG. 10A: T helper gene ontology for DEGs more expressed in BCG-STING-SCV2 lungs than SCV2. FIG. 10B: T helper gene ontology for DEGs more expressed in SCV2 lungs than BCG-STING-SCV2.

FIGS. 11A-B show differentially expressed genes in alveolar macrophage. FIG. 11A: alveolar macrophage gene ontology for DEGs more expressed in BCG-STING-SCV2 lungs than SCV2. FIG. 11B: Alveolar macrophage gene ontology for DEGs more expressed in SCV2 lungs than BCG-STING-SCV2.

FIGS. 12A-B show differentially expressed genes in Il1rn+ granulocyte. FIG. 12A: Il1rn+ granulocyte gene ontology for DEGs more expressed in BCG-STING-SCV2 lungs than SCV2. FIG. 12B: Il1rn+ granulocyte gene ontology for DEGs more expressed in SCV2 lungs than BCG-STING-SCV2.

FIGS. 13A-H show improved antitumor efficacy of BCG-disA-OE is STING-dependent. FIG. 13A: tumor weight at the time of necropsy. FIG. 13B: total CD45+ immune cells in tumors. FIG. 13C: total tumor infiltrating CD3+ lymphocytes. FIG. 13D: IFN-Y+ tumor infiltrating CD8+ cells. FIG. 13E-F: activated CD8+ T cells. FIG. 13G: tumor infiltrating inflammatory macrophages. FIG. 13H: differential abundance of TNF+ immunosuppressive macrophages in MB49 tumors after necropsy. 2-tailed Student's t-test.

FIGS. 15A-B show BCG induced differential glucose uptake in bone-marrow-derived macrophages (BMDMs). FIG. 15A-B: Bar diagram showing differential glucose uptake measured by induced expression of GLUT1 and intracellular fluorescent 2-NBDG in BMDMs following infection of MCG strains.

FIGS. 16A-B show BCG-STING versus small molecule STING agonist (ADU-S100). FIG. 16A: STING agonist ADU-S100. FIG. 16B: tumor staging data.

FIGS. 17A-B show cystic fibrosis data. FIG. 17A: Annual rates of NTM infection in CF patients during the study period were reported in aggregate (all countries) and by universal BCG vaccination policy (BCG suspended vs. active universal BCG vaccination). FIG. 17B: Annual NTM infection rates in CF patients for countries that provided universal BCG vaccination during the study period grouped by BCG vaccination strategy (single vs. multiple dose) in comparison to countries that have suspended BCG vaccination.

FIGS. 18A-H show prevalence results of lung pathology in BCG-STING and BCG-WT vaccinated animals compared with unvaccinated animals. FIG. 18A: bronchopneumonia prevalence. FIG. 18B: Neutrophil infiltration prevalence. FIG. 18C: macrophage infiltration prevalence. FIG. 18D: interstitial infiltration prevalence. FIG. 18E: lymphocyte infiltration prevalence. FIG. 18F: perivascular inflammation prevalence. FIG. 18G: intra-alveolar inflammation prevalence. FIG. 18H: peribronchial inflammation prevalence.

DETAILED DESCRIPTION OF THE INVENTION

Figure 1:
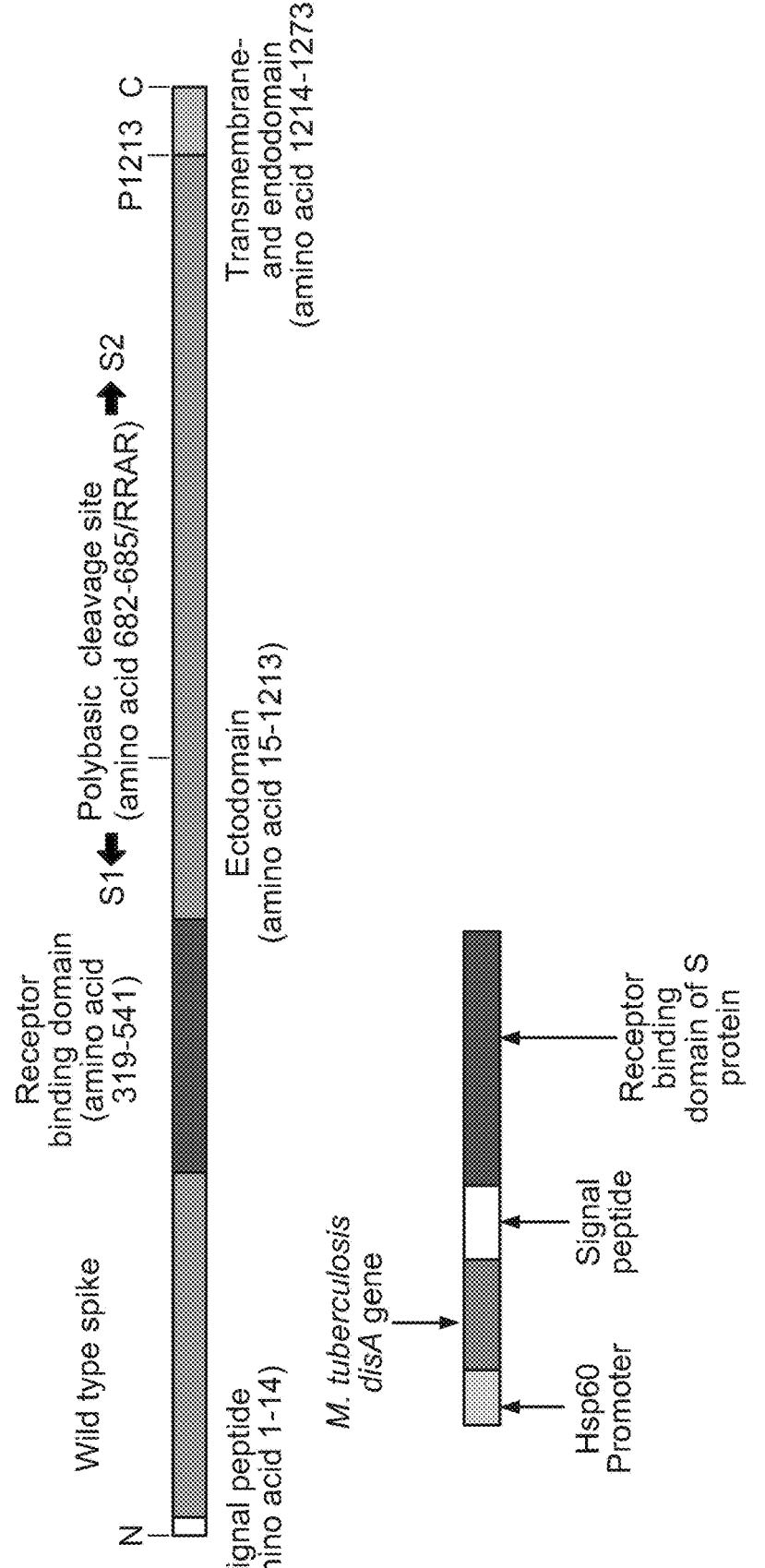
FIG. 1 is an illustration of recombinant BCG overexpressing STING agonist and SARS-CoV-2 protein fragment.

The present invention relates to a BCG based therapeutic agent using a BCG strain that overexpresses the STING agonist, c-di-AMP designated BCG-disA-OE or BCG-STING. The invention further relates to the use of BCG-disA-OE for the prevention, amelioration or treatment of viral infections, such as primary respiratory infections and SARS-CoV-2.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. The phrases "nucleic acid" or "nucleic acid sequence" includes oligonucleotide, nucleotide, polynucleotide, or to a fragment of any of these, to DNA or RNA (e.g., mRNA, rRNA, tRNA, iRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., e.g., double stranded iRNAs, e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. "Oligonucleotide" includes either a single stranded polydeoxynucleotide or two complementary polydeoxynucleotide strands that may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

The term "gene" means the segment of DNA involved in producing a polypeptide chain; it includes regions preceding and following the coding region (leader and trailer) as well as, where applicable, intervening sequences (introns) between individual coding segments (exons). "Operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term "promoter" includes all sequences capable of driving transcription of a coding sequence in a cell, e.g., a plant cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

The term "treatment" is used interchangeably herein with the term "therapeutic method" and refers to both 1) therapeutic treatments or measures that cure, slow down, lessen symptoms of, and/or halt progression of a diagnosed pathologic conditions or disorder, and 2) and prophylactic/ preventative measures. Those in need of treatment may include individuals already having a particular medical disorder as well as those who may ultimately acquire the disorder (i.e., those needing preventive measures).

The terms "therapeutically effective amount", "effective dose," "therapeutically effective dose", "effective amount," or the like refer to that amount of the subject compound that will elicit the biological or medical response of a tissue, system, animal or human that is being sought by the researcher, veterinarian, medical doctor or other clinician. Generally, the response is either amelioration of symptoms in a patient or a desired biological outcome. The effective amount can be determined as described herein.

The terms "administration of" and or "administering" should be understood to mean providing a pharmaceutical composition in a therapeutically effective amount to the subject in need of treatment. Administration routes can be enteral, topical or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticulare, subcapsular, subarachnoid, intraspinal and intrasternal, oral, sublingual buccal, rectal, vaginal, nasal ocular administrations, as well infusion, inhalation, and nebulization. The phrases "parenteral administration" and "administered parenterally" as used herein means modes of administration other than enteral and topical administration. The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

According to the invention, the term "vaccine" relates to a pharmaceutical preparation (pharmaceutical composition) or product that upon administration induces an immune response, in particular a cellular immune response, which recognizes and attacks a pathogen or a diseased cell such as a cancer cell. A vaccine may be used for the prevention or treatment of a disease.

Dysregulated host innate immune responses contribute to the pathology of Covid-19. In the early phase of infection, a potent host defense leads to suppression of viral replication, which subsequently leads to low levels of inflammation, less severe symptoms, and a good prognosis. If host defense mechanisms are defective, then they can lead to massive viral replication, systemic hyperinflammation, high severity of disease, and ultimately, death. Trained immunity of macrophages can help to boost early immune responses against the virus (preventive). Blocking excessive inflammation, example by targeting IL-6, a principal component of Covid-19 cytokine storm, could help alleviate symptoms and pathology (therapeutic).

BCG-disA-OE, enhances the elevated trained immunity of macrophages and promotes early anti-viral Type I interferon responses in a subject. A recombinant BCG strain called BCG-disA-OE was generated. The disA gene is an endogenous diadenylate cyclase gene which catalyzes the production of cyclic di-AMP which is a STING agonist. It has been shown that BCG-disA-OE is superior to standard BCG in reducing the severity of TB in guinea pigs. It has been shown that BCG-disA-OE is superior to standard BCG in the therapy of bladder cancer in mice and in rats. Finally, it has also been shown that BCG-disA-OE is safer than standard BCG in two different mouse models.

Delayed production of type I IFN promotes the enhanced release of monocyte chemoattractants by alveolar epithelial cells (and likely also by macrophages and stromal cells), leading to sustained recruitment of blood monocytes into the lungs. Monocytes differentiate into pro-inflammatory macrophages. Activated natural killer (NK) cells and T cells further promote the recruitment and activation of monocyte-derived macrophages. Virus sensing by intracellular RNA sensors such as TLR7 promote Type I IFN, which induce the expression of SARS-CoV-2 entry receptors, enabling the virus to gain access to the cytoplasm of macrophages and to activate the NLRP3 inflammasome, leading to the secretion of mature IL-1β and/or IL-18. Activated monocyte-derived macrophages contribute to the COVID-19 cytokine storm by releasing massive amounts of pro-inflammatory cytokines.

Trained immunity is a type of innate immunity in which a first antigenic stimulus potentiates immune responses to a second heterologous stimulus. The mechanism of trained immunity is believed to be epigenetic and metabolomic changes induced by the first stimulus that raise the immunologic set point to new heterologous stimuli. In recent data, it has been shown that BCG-disA-OE elicits more potent trained immunity (measured by epigenetic and metabolomic changes) in immune cells.

Standard BCG has been shown to be protective against viral infections including influenza, RSV, yellow fever and others by a trained immunity mechanism. Because it elicits stronger trained immunity than standard BCG, the present invention provides that BCG-disA-OE is protective against viral infections including COVID-19. Secondly, BCG-disA-OE vaccination may reduce the severity of viral infections including COVID-19.

It is shown herein that BCG-disA-OE elicits much higher Type I IFN responses in vitro and in vivo than does BCG-WT. Specifically, it is presently shown that BCG and M.tb express low levels of c-di-AMP which triggers a potent Type I IFN response and increased levels of autophagy and that compared with BCG-wild type (WT), BCG-disA-OE shows: superior protection from TB disease in the guinea pig model; superior intravesical efficacy against NMIBC in two animal models; increased safety in two mouse models; more potent pro-inflammatory cytokine responses in macrophage and bladder cancer cells/cell lines; greater myeloid cell polarization with an M1 shift, enhanced phagocytosis, and increased autophagy; a higher degree of proinflammatory epigenetic marks in human MDM; and a greater metabolomic shift towards glycolysis in human MDM.

BCG overexpressing a STING agonist (BCG-disA-OE or BCG-STING) serves a dual purpose: it enhances the elevated trained immunity of macrophages already known to be conferred by BCG-WT and also promotes critical early anti-viral Type I IFN responses.

Covid-19, the current global pandemic caused by the novel coronavirus SARS-CoV-2, has precipitated a severe health and economic crisis worldwide, dramatically affecting the lives of billions of people across multiple continents. As of this writing, 11 million individuals have been infected globally with over 500,000 deaths. The disease is expected to remain a global pandemic for many months, and some experts predict a worsening during the fall and winter in the northern hemisphere. An effective vaccine is widely distress and even death. Co-morbidities, age, non-genetic and genetic risk factors seem to contribute to disease progress. The Bacille Calmette-Guérin (BCG) vaccine, with documented protective effect against meningitis and disseminated TB in children, is shown to protect against heterologous infections, due to the induction of long-term innate immune responses known as trained immunity, which is mediated by an epigenetic, transcriptional and functional reprogramming of innate immune cells. BCG is one of the best vaccine adjuvants (i.e., priming agents) known. It has been used in many prime-boost studies as the priming agent with another TB vaccine. Hence it is proposed that induction of trained immunity by BCG may reduce susceptibility to SARS-CoV-2 or mitigate disease severity. Several clinical trials to assess the effect of BCG vaccination on COVID-19 are currently underway. The BCG vaccine may not only offer an interim solution before a specific COVID-19 vaccine is fully implemented, but, if BCG-induced trained immunity indeed is proven as an effective tool against emerging pathogens, BCG could also serve as a potentially safe bridge vaccine to be used at the early stage of a future coronavirus-related pandemic. However, concerns have been raised regarding the possibility that an excessive inflammatory response induced by BCG in some patients with COVID-19 might aggravate disease. Pre-clinical studies using animal studies as well as randomized human clinical trials are therefore critically needed to ensure that up-regulation of trained immunity by BCG does not exacerbate disease in patients with severe Covid-19. In addition, in the animal models, the efficacy of a novel STING agonist-expressing recombinant BCG are needed and may provide protective effects by helping to overcome initial delayed anti-viral Type I interferon responses observed in Covid-19.

BCG was developed in 1921 as a live attenuated vaccine for tuberculosis (TB) by French microbiologists Albert Calmette and Camille Guérin who serially passaged a virulent strain of M. bovis 239 times over 13 years. Currently, intradermal BCG is given to newborns in virtually all nations of the world except the US & Canada and certain countries in W. Europe. It is believed to be the single most widely utilized vaccine in history with ~152 million doses given annually and an aggregate of at least 5 B doses given. During the mid-20th century BCG was used successfully as an intra-tumoral immunotherapy for a variety of solid tumors including melanoma, breast and colon cancers. However, its use fell out of favor as cytotoxic chemotherapy became more popular. Since 1976, ever since it was found that intravesical BCG was an effective immunotherapy for non-muscle invasive bladder cancer (NMIBC), BCG is in use for the treatment of NMIBC, and is the only bacterial agent approved by the FDA for cancer.

BCG protects against unrelated infections including viral infections. Numerous studies reveal that BCG confers heterologous protective efficacy against numerous viral infections both in humans and animal models. It has been shown that humans who were BCG vaccinated were better able to control YFV viremia following challenge with an attenuated YFV strain than sham-vaccinated individuals. RCTs also show that BCG can protect against respiratory infections. In Guinea-Bissau, a high-mortality setting, BCG reduced all-cause neonatal mortality by 38%, due in major part to fewer deaths from pneumonia and sepsis, and In South Africa, BCG reduced respiratory tract infections by 73% in adolescents.

The finding that BCG vaccination provides heterologous protective effects on unrelated viral and bacterial infections has led to increased interest in the recently discovered phenomenon of trained immunity (TI). TI represents a paradigm shift in understanding of innate immune defense. Induction of TI leads to activation of specific receptor signaling pathways and subsequent epigenetic, metabolic, and transcriptional changes in innate immune cells. TI manifests in multiple ways, such as the enhanced production of pro-inflammatory cytokines, resulting in non-specific and enhanced immune responses to subsequent challenge.

Importantly, preliminary animal model studies strongly suggest that BCG overexpressing a STING agonist induces enhanced TI in macrophage.

Countries currently using BCG vaccination have lower SARS-CoV-2 incidence and death rates than those that do not. In recent study by Miller et al. and Shet et al., COVID-19 rates were compared across countries based on whether a universal BCG vaccination policy is currently in place. Upper-to-middle and high-income countries that do not utilize BCG (e.g., Italy, United States) has significantly higher incidence rates of SARS-CoV-2 infections (p=0.0064) and deaths (p=0.00086) than those that do use BCG (e.g., Japan, Brazil, Denmark). These findings strengthen the argument that BCG may demonstrate preventive efficacy against SARS-CoV-2.

Safety profile of BCG vaccination determined in a retrospective study in two relatively small groups of volunteers either vaccinated with BCG or not in the last 5 years, has shown that BCG vaccination was not associated with any increase in the incidence of disease or severity of COVID-19 symptoms. An interim analysis of the ACTIVATE study on 198 elderly hospitalized for various conditions randomized to receive BCG or placebo at discharge, shows that BCG significantly decreased the time to first infection, with no difference in the frequency of adverse effect between the groups. These data show that BCG vaccination is safe and can protect the elderly against infections. However, larger studies are needed to assess protection against COVID-19.

Promoting early Type I IFN signaling as a therapeutic in Covid-19 Type I IFN signaling induces potent anti-viral immune responses. Recent studies have shown that in contrast to other respiratory viruses, Type I IFN responses following SARS-CoV-2 infection are significantly reduced due to virus interference with host signaling, and pretreatment with Type I IFN can reduce SARS-CoV-2 replication. In critically ill patients a profoundly impaired Type I IFN response and consequent downregulation of IFN-stimulated genes has been observed, associated with a high blood virus load and an exacerbated inflammatory response characterized by increased TNFa, IL-6 and chemokines. Since STING activation is a potent inducer of Type I IFN responses, it stands to reason that BCG overexpressing a STING agonist is likely to offer superior anti-SARS-CoV-2 protection to that elicited by traditional BCG.

STING agonists elicit potent Type I IFN responses. Recent studies have identified a critical role for STING, an intracellular sensor, in mediating innate immune responses to cellular stress or pathogen infections. STING is a cytosolic receptor for both pathogen-associated molecular pattern (PAMP) molecules such as cyclic dinucleotides c-di-AMP or c-di-GMP produced by bacteria, and for endogenous mammalian danger signaling DAMP molecules such as 2',3' cyclic GMP-AMP (cGAMP). cGAMP is synthesized by cGAS (cyclic GMP-AMP synthase) in response to microbial or self-derived cytosolic double-stranded DNA. Activation of STING induces numerous interferon-stimulated genes including type I interferons (IFNa/6), and is associated with co-activation of the NF-KB and STAT6 transcription factors that follows or parallels the induction of interferon regulatory factors (IRF) transcription factors. Thus, endogenous and exogenous cyclic dinucleotides (CDNs) are strong TLR-independent mediators of innate host defenses. Based on the key role of STING signaling, pharmacological stimulation of the pathway using small molecule STING agonists is currently being tested for enhancement of anti-viral therapy and anti-tumor immunity.

At least 15 companies are currently working to generate small molecule STING agonists, and two such agents are in phase 2 trials.

Figure 2C:
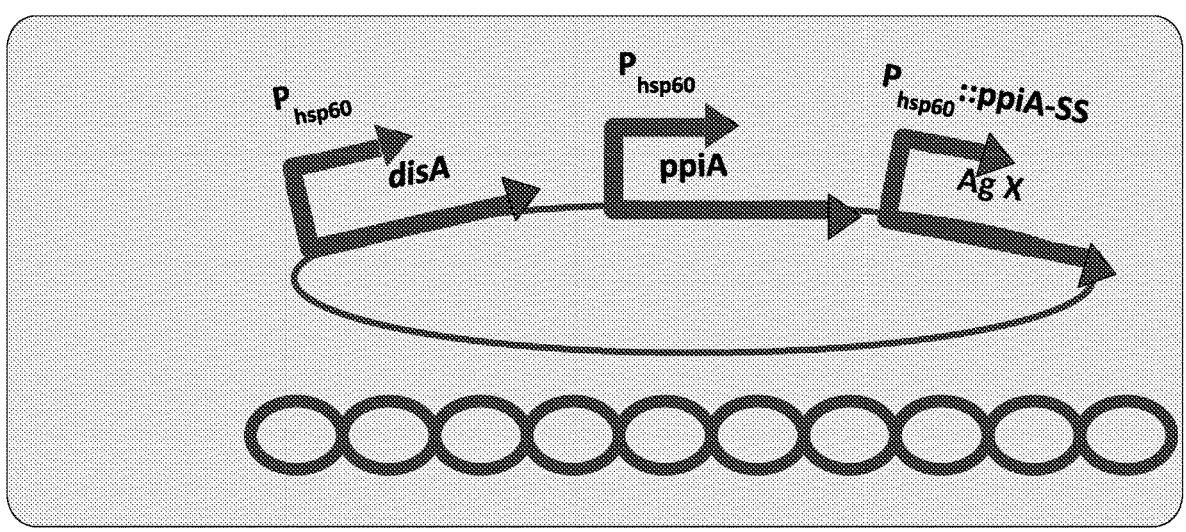

Development of a recombinant BCG overexpressing a STING agonist. It has been shown that M.tb and BCG synthesize and secrete cyclic-di-AMP, a STING agonist closely related to the natural human STING ligand, cGAMP. It was shown that bacterial-derived c-di-AMP activates the IRF3 pathway and induces Type I IFN responses through STING-dependent signaling. In this microbial pathogenesis study a genetically engineered BCG strain called BCG-disA-OE was used in which the endogenous microbial diadenylate cyclase gene, disA, was fused to a strong mycobacterial promoter, Phsp60, causing the overexpression of disA by 200-fold at the mRNA level and excess production c-di-AMP by 15-fold (FIG. 2). Preliminary results provide evidence of superior efficacy and induction of trained immunity induced by BCG-disA-OE.

In one embodiment, the present invention provides a recombinant bacille Calmette-Guerin (BCG) bacterial strain having a disA gene, wherein the bacterial strain is optionally resistant to kanamycin. In one aspect, the bacterial strain over expresses a stimulator of interferon genes (STING) agonist. In certain aspects, the STING agonist is c-di-AMP. In some aspects, the disA gene is a *M. tuberculosis* disA gene. In an additional aspect, the disA gene is fused to a mycobacterial promoter. In a further aspect, the mycobacterial promoter is $P_{HSP60}$. In an additional aspect, the nucleic acid sequence of the bacterial strain does not have kanamycin resistance markers. In an additional aspect the strain further comprises a selectable marker. In certain aspects, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.

Bacillus Calmette—Guérin (BCG) vaccine is a vaccine primarily used against tuberculosis (TB). BCG is prepared from a strain of the attenuated live bovine tuberculosis bacillus. BCG has been shown to reprogram both myeloid cells and NK cells through processes collectively termed "trained immunity". BCG is rapidly phagocytosed by macrophages and has been shown to elicit both epigenetic and metabolomic modifications that elevate their immune set-point upon re-challenge with a heterologous antigens including viruses. Upon re-challenge with heterologous antigens, BCG-trained macrophages show elevated cytokine release and demonstrate reprogramming towards Ml-like phenotypes. These initial events are associated with heterologous B and T-lymphocyte activation and elevated antibody titers as well as expansion of unconventional T cells such as innate lymphoid cells (ILCs) and mucosa-associated invariant T (MATT) cells. BCG exposure also leads to expanded "trained" populations of hematopoietic stem cells (HSCs) and multipotent progenitors (MPPs) in the bone marrow that confer enhanced protection against subsequent pathogen challenges.

Randomized control studies of BCG vaccination in humans have demonstrated improved control of live attenuated yellow fever virus , live-attenuated influenza A (H1N1), and human papilloma virus, and animal studies have similarly demonstrated a BCG benefit against at least eight viruses including two positive-sense, single-stranded RNA viruses.

*M. tuberculosis* (Mtb) and BCG synthesize and secrete cyclic-di-AMP, a STING agonist closely related to the natural human STING ligand, cGAMP. It was shown that bacterial-derived c-di-AMP activates the IRF3 pathway and induces Type I IFN responses through STING-dependent signaling. The disA gene from *M. tuberculosis* genome encodes a di-adenylate cyclase enzyme. The genetically engineered BCG strain designated BCG-disA-OE or BCG-STING in which disA, was fused to a strong mycobacterial promoter, $P_{hsp60}$, causing the overexpression of disA by 200-fold at the mRNA level and excess production c-di-AMP by 15-fold.

In an additional embodiment, the present invention provides a pharmaceutical composition comprising a recombinant bacille Calmette-Guerin (BCG) bacterial strain having a disA gene and a pharmaceutically acceptable carrier, wherein the bacterial strain is optionally resistant to kanamycin. In one aspect, the bacterial strain over expresses c-di-AMP. In an additional aspect, the disA gene is fused to a mycobacterial promoter. In certain aspects, the pharmaceutically acceptable carrier is phosphate buffer; citrate buffer; ascorbic acid; methionine; octadecyldimethylbenzyl ammonium chloride; hexamethonium chloride; benzalkonium chloride; benzethonium chloride; phenol alcohol; butyl alcohol; benzyl alcohol; methyl paraben; propyl paraben; catechol; resorcinol; cyclohexanol; 3-pentanol; m-cresol; low molecular weight (less than about 10 residues) polypeptides; serum albumin; gelatin; immunoglobulins; polyvinylpyrrolidone glycine; glutamine; asparagine; histidine; arginine; lysine; monosaccharides; disaccharides; glucose; mannose; dextrins; EDTA; sucrose; mannitol; trehalose; sorbitol; sodium; saline; metal surfactants; non-ionic surfactants; polyethylene glycol (PEG); magnesium stearate; water; alcohol; saline solution; glycol; mineral oil or dimethyl sulfoxide (DMSO). In an additional aspect, the nucleic acid sequence of the bacterial strain does not have kanamycin resistance markers. In an additional aspect the strain further comprises a selectable marker. In certain aspects, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.

As used herein, "pharmaceutical composition" refers to a formulation comprising an active ingredient, and optionally a pharmaceutically acceptable carrier, diluent or excipient. The term "active ingredient" can interchangeably refer to an "effective ingredient", and is meant to refer to any agent that is capable of inducing a sought-after effect upon administration. Examples of active ingredient include, but are not limited to, chemical compound, drug, therapeutic agent, small molecule, etc.

By "pharmaceutically acceptable" it is meant the carrier, diluent or excipient must be compatible with the other ingredients of the formulation and not deleterious to the recipient thereof, nor to the activity of the active ingredient of the formulation. Pharmaceutically acceptable carriers, excipients or stabilizers are well known in the art, for example Remington's Pharmaceutical Sciences, 16th edition, Osol, A. Ed. (1980). Pharmaceutically acceptable carriers, excipients, or stabilizers are nontoxic to recipients at the dosages and concentrations employed, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides;

proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN™, PLURONICS™ or polyethylene glycol (PEG). Examples of carrier include, but are not limited to, liposome, nanoparticles, ointment, micelles, microsphere, microparticle, cream, emulsion, and gel. Examples of excipient include, but are not limited to, anti-adherents such as magnesium stearate, binders such as saccharides and their derivatives (sucrose, lactose, starches, cellulose, sugar alcohols and the like) protein like gelatin and synthetic polymers, lubricants such as talc and silica, and preservatives such as antioxidants, vitamin A, vitamin E, vitamin C, retinyl palmitate, selenium, cysteine, methionine, citric acid, sodium sulfate and parabens. Examples of diluent include, but are not limited to, water, alcohol, saline solution, glycol, mineral oil and dimethyl sulfoxide (DMSO).

In a further embodiment, the present invention provides a method of preventing, ameliorating or treating primary a viral infection in a subject comprising administering a recombinant bacille Calmette-Guerin (BCG) bacterial strain having a disA gene, thereby treating the infection. In one aspect, the viral infection is a primary respiratory infection. In certain aspects, the infection is a non-tuberculosis mycobacteria infection or a SARS-CoV-2 infection. In an additional aspect, the subject has obesity, diabetes, cystic fibrosis (CF), non-cystic-fibrosis bronchiectasis, or HIV/AIDS. In one aspect, the bacterial strain over expresses a stimulator of interferon genes (STING) agonist. In certain aspects, the STING agonist is c-di-AMP. In an additional aspect, the disA gene is a $M.$ $tuberculosis$ disA gene. In a further aspect, the disA gene is fused to a mycobacterial promoter. In a specific aspect, the mycobacterial promoter is $P_{HSP60}$. In an additional aspect, the nucleic acid sequence of the bacterial strain does not have kanamycin resistance markers. In an additional aspect, the nucleic acid sequence of the bacterial strain does not have kanamycin resistance markers. In a further aspect, the bacterial strain is optionally resistant to kanamycin. In an additional aspect the strain further comprises a selectable marker. In certain aspects, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.

In a further embodiment, the present invention provides a method of regulating glucose levels in a subject by administering a recombinant bacille Calmette-Guerin (BCG) bacterial strain having a disA gene, thereby regulating glucose levels. In one aspect, the glucose levels are increased after administration of the BCG bacterial strain. In an additional aspect, the glucose levels are decreased after administration of the BCG bacterial strain. In a further aspect, the bacterial strain over expresses a stimulator of interferon genes (STING) agonist. In certain aspects, the STING agonist is c-di-AMP. In an additional aspect, the nucleic acid sequence of the bacterial strain does not have kanamycin resistance markers. In a further aspect, the bacterial strain is optionally resistant to kanamycin. In an additional aspect the strain further comprises a selectable marker. In certain aspects, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.

In one embodiment, the present invention provides a method of inducing an immunological response in a subject suffering from a viral infection by administering a recombinant bacille Calmette-Guerin (BCG) bacterial strain having a disA gene, thereby inducing an immunological response. In one aspect, the administration of the BCG bacterial strain causes an increase in lung alveolar macrophages, the prevention of SCV2-mediated T cell lymphopenia, the prevention of granulocyte lung infiltration, an increase immunoglobulin-producing plasma cells in the lung, and/or an increase in Treg cells in the lung. In an additional aspect, the bacterial strain over expresses a stimulator of interferon genes (STING) agonist. In certain aspects, the STING agonist is c-di-AMP. In an additional aspect, the nucleic acid sequence of the bacterial strain does not have kanamycin resistance markers. In a further aspect, the bacterial strain is optionally resistant to kanamycin. In an additional aspect the strain further comprises a selectable marker. In certain aspects, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.

In certain embodiments, the present invention provides methods for preventing non-tuberculous mycobacterium infections in patients having cystic fibrosis or non-cystic fibrosis bronchiectasis. Recently, a prospective clinical trial in which 5 healthy people in St. Louis, MO were given intramuscular BCG observed post-vaccination increases in protective immunity against NTM. Additional compelling human evidence for BCG-mediated protection against NTM comes from European nations with strong surveillance programs where BCG vaccination was suspended or terminated. In France, the mean incidence of culture-confirmed NTM cervical lymphadenitis sharply increased from 0.57 to 3.7 per 100,000 children per year after mandatory BCG vaccination was discontinued. Similarly, in a large retrospective population-based study in Finland, when BCG policy changed from universal to selective vaccination strategy in 2006, childhood NTM infections increased drastically, with an incident rate ratio of 19.03 (95% CI, 8.8-41.07; P<0.001). These studies support the hypothesis that BCG offers cross-protection against NTM disease in humans.

An independent assessment of country-specific BCG vaccination policies was conducted per the WHO and NTM infection rates in 2019 as reported in the European CF Society Patient Registry (ECFSPR). As shown in Table 1, low rates of NTM infection are often observed in European countries that universally vaccinate for BCG, whereas higher rates are seen in countries that have ceased their standard BCG vaccination strategies, especially countries in which vaccination was suspended in the 1980s or 1990s. Listed countries have >75% of the national CF population in the ECFSPR and low missing data on NTM infection. Similar low NTM rates are seen in CF patients in Brazil. These findings support the hypothesis that BCG vaccination may protect against NTM infection in people with CF

TABLE 1

| Country | BCG vaccination schedule | CF NTM rate |
|---|---|---|
| Still BCG vaccinate: | | |
| Serbia | birth | 0% |
| Albania | birth | 0% |
| Russia | 3 days, 7 years | 0.55% |
| Macedonia | birth | 0.87% |
| Hungary | birth | 2.58 |
| Portugal | specific-risk groups | 4.89% |
| Ireland | birth & select high risk | 7.68% |
| No longer BCG vaccinate: | | |
| Slovak Republic | Suspended 2012 | 0.38% |
| Italy | Suspended 2001 | 0.86% |
| Belgium | Suspended 2013 | 1.48% |
| France | Suspended 2007 | 2.64% |
| Netherlands | Suspended 2005 | 2.65% |
| Spain | Suspended 1981 | 3.10% |
| Denmark | Suspended 1986 | 3.23% |
| Switzerland | Suspended 1987 | 4.16% |
| Sweden | Suspended 1985 | 4.37% |
| Slovenia | Suspended 2005 | 4.59% |
| Austria | Suspended 1990 | 4.62% |
| UK | Suspended 2005 | 5.99% |
| Israel | Suspended 1982 | 7.68% |
| Luxembourg | Suspended (unk date) | 8.33% |

For at least 35 years, it has been known that BCG vaccination can protect against NTM infection in mice. More recent studies not only confirm the bacterial containment of CFU counts but also have characterized beneficial host immune responses including cytokine and cell-mediated immunity.

In one embodiment, the present invention provides a method of preventing, ameliorating or treating a bacterial infection in a subject by administering a recombinant bacille Calmette-Guerin (BCG) bacterial strain having a disA gene, thereby treating the infection. In one aspect, the bacterial infection is a primary respiratory infection. In certain aspects, the infection is a non-tuberculosis mycobacteria infection. In an additional aspect, the subject has cystic fibrosis (CF). In a further aspect, the bacterial strain over expresses a stimulator of interferon genes (STING) agonist. In certain aspects, the STING agonist is c-di-AMP. In one aspect, the disA gene is fused to a mycobacterial promoter. In an additional aspect, the nucleic acid sequence of the bacterial strain does not have kanamycin resistance markers. In a further aspect, the bacterial strain is optionally resistant to kanamycin. In an additional aspect the strain further comprises a selectable marker. In certain aspects, the selectable marker is a Kanamycin resistance gene, a panC gene and/or panD gene. In a further aspect, the strain further comprises a plasmid. In one aspect, the strain is modified to remove the Kanamycin resistance gene and/or the panC and panD genes.

The following examples are provided to further illustrate the embodiments of the present invention but are not intended to limit the scope of the invention. While they are typical of those that might be used, other procedures, methodologies, or techniques known to those skilled in the art may alternatively be used.

EXAMPLES

Example 1

Generation of BCG-STING

BCG-STING (also called BCG-disA-OE) is a recombinant derivative of BCG Pasteur, which overexpresses the endogenous mycobacterial diadenylate cyclase gene disA (*M. tuberculosis* CDC1551 gene MT3692; an identical gene in *M. tuberculosis* H37Rv is annotated as gene Rv3586). The disA genes of *M. tuberculosis* and BCG are 100% identical at the nucleotide level. disA catalyzes the conversion of 2 adenosine triphosphate molecules to c-di-AMP.

The overexpression construct was generated by fusing the disA gene to the strong mycobacterial promoter hsp60 within the episomal mycobacterial overexpression vector pSD5-hsp60 which harbors a kanamycin resistance cassette for selectability. The MT3692 (disA) gene of *M. tuberculosis* was PCR-amplified from *M. tuberculosis* CDC 1551 genomic DNA using gene-specific cloning primers. The amplicons were cloned into the mycobacterial shuttle expression vector pSD5-hsp60 at the NdeI and MluI restriction sites. The construct (pSD5-hsp60-MT3692) generation was confirmed using restriction analyses and sequencing. Constructs were used to transform the wild-type BCG Pasteur strain by electroporation, and recombinant clones were selected against Kanamycin (25 μg/mL) to yield strain BCG-STING(Pasteur) also called BCG-disA-OE(Pasteur). Plasmid The same plasmid (pSD5-hsp60-MT3692) was also electroporated into wild type BCG Tice yielding BCG-STING(Tice) also called BCG-disA-OE(Tice). BCG-STING(Pasteur) and BCG-STING(Tice) have been tested in parallel numerous in vitro phenotypic assays and in vivo mouse models, and they perform comparably. They each show distinct phenotypes in in vitro phenotypic assays and in vivo mouse models compared to their corresponding wild type BCG strains.

A second-generation BCG-STING has also been created in which the kanamycin-resistance conferring gene, kanR, carried by BCG-STING has been removed. This second-generation recombinant BCG has the same antibiotic resistance profile of wild-type BCG and is called BCG-STING-NoKan. A method to generate BCG-STING-noKan was described in WO2021/163602. One BCG-STING-noKan strain called BCG-STING-noKan-#1 was successfully generated.

To generate BCG-STING-noKan-#1, a BCG-Pasteur-Aeras-ΔpanCD, a BCG strain carrying an unmarked deletion of the panC (encoding the protein pantoate-beta-alanine ligase) and panD (encoding the protein aspartate 1-decarboxylase) and hence is a pantothenate (Vitamin B5) auxotroph was obtained. The native panCD gene pair from BCG genomic DNA was PCR amplified, and similarly all of pSD5-hsp60-MT3692 except for the KanR cassette was PCR amplified. Gibson assembly was then used to generate a plasmid called p106c in which the BCG panCD pair replaces the KanR cassette. In p106c the 5'-untranslated region (5'-UTR) of panCD is absent and panCD coding sequences are fused to the KanR promoter which drives panCD transcription; 81 bp of the 3'-UTR of panCD are retained. Plasmid p106c was electroporated into BCG-Pasteur-Aeras-ΔpanCD, and a single colony was selected on Middlebrook 7H11 agar lacking supplementary pantothenate as BCG-STING-noKan-#1. The BCG-STING-noKan-#1 strain derived in this manner has the following properties. (i) It is fully susceptible to kanamycin, and KanR DNA cannot be PCR amplified from it. (ii) By qRT-PCR using equivalent numbers of bacteria to prepare RNA, it shows disA gene relative gene expression levels of 226, while that for BCG-STING (first generation, Kan-resistant) was 270 (p=0.3, not statistically significantly different), and that for BCG-WT was 1.0. (iii) IRF3 RAW-Lucia or IRF3 RAW-Blue reporter macrophages (Invivogen) when exposed to it give RLU or $A_{655}$ values that are elevated and statistically significantly higher than those with BCG-WT, and not statistically significantly different from those of BCG-STING (first generation, Kan-resistant). (iv) Produces c-di-AMP levels (detected by liquid chromatography-mass spectrometry, LCMS) of 50 ng (whole cell fraction from the pellet of a 3 ml culture grown to an $OD_{60}$ of 1.02 or ~3 ×$10^8$ bacteria) (the corresponding BCG-WT level for an $OD_{600}$ 1.32 culture is 1.0 ng) and of 2.3 ng/ml in the supernatant of the same culture (the corresponding BCG-WT level for an ($OD_{600}$ 1.32 culture is 0.8 ng/ml).

To generate a BCG-STING-noKan-#2, a BCG-Pasteur-ΔpanCD will be generated. A mycobacteriophage phAE187 containing ΔpanCD reg-HygR-res has been obtained, and was used to replace the panCD gene with a HygR cassette in the BCG-Pasteur strain. Following phage infection of BCG-Pasteur, hygromycin-resistant colonies were selected on complete Middlebrook 7H11 plates supplemented with 15 mg/ml of hygromycin. The resulting strain was confirmed to (i) be unable to grow on solid media not supplemented with 24 μg/ml of panthothenate (i.e., it is an pantothenate auxotroph), (ii) be lack any measurable DNA PCR amplification using primers specific for panCD, and (iii) to contain a HygR cassette using primers specific for that gene. The HygR-in-place-of-panCD will next be infected with mycobacteriophage phAE280 containing the gamma-delta resolvase gene and bacteria will be plated on Middlebrook 7H11 plates supplemented with 24 μg/ml of panthothenate. After infection 200-500 colonies will be selected and by replica plating, and colonies will be selected that are hygromycin-susceptible. Candidates will be screened by hygromycin gene-specific primers to confirm that they lack the HygR gene. They will also be confirmed to by pantothenate auxotrophs. Upon successful derivation of this unmarked BCG-Pasteur ΔpanCD unmarked deletion strain, plasmid p106c will be elctroporated into it and a select single colonies on Middlebrook 7H11 agar lacking supplementary pantothenate. Such transformants will be candidate clones of BCG-STING-noKan-#2. The candidates will be validated by demonstrating susceptibility to kanamycin, and that KanR DNA cannot be PCR amplified. Subsequently, they will be further validated by qRT-PCR disA gene expression, IRF3 RAW-Lucia or IRF3 RAW-Blue reporter macrophages, c-di-AMP levels by LCMS as described above.

Example 2

Protective Efficacy of BCG-WT and BCG-disA-OE Against SARS-CoV-2 Infection In Nonhuman Primates It will be determined whether vaccination with BCG-disA-OE will show enhanced protective efficacy compared to BCG-WT against SARS-CoV-2 infection in NHP by evaluating immune responses and lung pathology.

It is believed that vaccination with BCG will protect against and/or alleviate SARS-CoV-2 disease in A non-human primate (NHP) model, and that and BCG overexpressing a STING agonist (BCG-disA-OE) will show enhanced protective efficacy compared to BCG-WT.

NHP models that recapitulate human disease are essential for understanding of the pathogenic processes involved in viral and bacterial infections, and for the development of vaccines and antimicrobials. It was found that BCG-disA-OE shows improved efficacy relative to BCG-WT against TB in mice and in the guinea pig models. In mice, it has been shown that the effects were in part mediated by trained immunity of macrophages. Trained immunity provides protection against viral infections, but it is also likely to contribute to excessive immune response against SARS-CoV-2. In order to determine the outcome of SARS-CoV-2 infection in BCG vaccinated NHPs, it is important to further test the efficacy of BCG and BCG-disA-OE in NHPs. Epithelial cells and pneumocytes in macaques express ACE2 receptor and NHPs are susceptible for SARS-CoV-2 infection. Cynomolgus and rhesus macaques challenged with SARS-CoV-2 showed gross lung lesions and pneumonia with mild and moderate clinical signs, and viral shedding pattern similar to that observed in humans. The efficacy of BCG and BCG-disA-OE will be tested in preventing SARS-CoV-2 infection in rhesus monkeys by vaccination with (i) sham, (ii) BCG-WT, or (iii) BCG-disA-OE followed by challenge with the virus.

Eighteen adult rhesus monkeys (three to twelve-year old, pathogen and retrovirus-free, and mycobacteria-naïve) will be assigned to three groups of six each. Each group will be vaccinated intradermally with PBS (unvaccinated controls), or with a target dose 106 CFU BCG-WT, or BCG-disA-OE.

During phase I (vaccination phase), a baseline bronchoalveolar lavage (BAL), CXR, PET CT Scan, and tuberculin skin test (TST) will be done at t=0 (prior to vaccination) and the same studies will be repeated at week 6 and week 12 post vaccination. Blood samples will be acquired 2 weeks before vaccination and every week following vaccination and infection, for blood count, immunological profiles, cytokine assays and blood chemistries. Blood draws and bone marrow biopsies will be performed at baseline and at weeks 6 and 12 to assess trained immunity-associated changes in peripheral blood mononuclear cells and in bone marrow myeloid precursors as have been documented in mice.

During phase II (SARS-Cov-2 challenge phase), twelve weeks post vaccination, animals will be moved to BSL 3 and challenged with SARS-CoV-2 by the intratracheal route which has been demonstrated to be an effective inoculation route. Respiratory swabs, blood draws, and CXRs will be performed immediately prior to inoculation and every 2 days post SARS-CoV-2 challenge for 2 week to measure viral shedding, antibody and other immune responses, and evaluation of pneumonitis, inflammation and lymphadenopathy. PET-CT scans will be performed just prior to SARS-CoV-2 challenge and then on days 3, 6, 9, 12, 16, 19, 23, and 28 post-challenge for evaluation of pneumonitis. BAL and bone marrow aspirates will be obtained weekly for evaluation of immune responses (cytokines, analysis of M1 and M2 macrophages and CD4+ and CD8+ T-lymphocytes).

During phase III (necropsy 4 weeks post-SARS-CoV-2 infection) animals will be euthanized and blood, BAL, lung, trachea, pharyngeal tissue, bone marrow, spleen, liver, small intestine and colon samples will be harvested. Viral abundance will be measured using SARS-CoV-2 RT-PCR and/or infectivity assay. Tissue sections will be analyzed and scored by histology for inflammation, hemorrhage, edema and necrosis. Cytokine levels, especially IL-6, and frequencies of M1 and M2 macrophages and CD4+ and CD8+ T-lymphocytes will be measured in blood and BAL. Coagulation factors will also be measured in blood, since inflammation-induced coagulation appears to be a clinical manifestation of disease. Using a wide-array of clinical, microbiological, pathology and immunological experiments described above, it will be determined whether vaccination with BCG or BCG-disA-OE can protect rhesus macaques from severe SARS-CoV2 induced disease.

A study showed that BCG, when injected intravenously, prevented TB disease following challenge with Mycobacterium tuberculosis in NHP. Since IV BCG remains experimental and is not FDA approved, testing a human-bioequivalent dose of BCG-disA-OE administered intradermally is important in evaluating the protective efficacy of BCG and BCG-disA-OE. In case it appears that protection engendered by BCG-disA-OE via the intradermal route is insufficient, it will be determined whether intravenous vaccination with BCG-disA-OE can result in statistically significant protection.

Example 3

Protective Efficacy of BCG-disA-OE inhACE2 and Golden Syrian Hamsters

Determine the protective efficacy of vaccination with BCG and BCG-disA-OE against SARS-CoV-2 infection in hACE2 transgenic mice and golden Syrian hamsters. It will be determined whether the vaccination with BCG-disA-OE will show enhanced protective efficacy compared to BCG-WT against SARS-COV2 infection in hACE2 transgenic mouse and golden Syrian hamster models of disease by evaluating immune responses and lung pathology.

Infection in mice: SARS-CoV infects and replicates in mice, but the animals do not develop disease equivalent in severity to that observed in human disease. To replicate human disease in mice, transgenic mice (Tg mice) were developed in which expression of human angiotensin-converting enzyme 2 (hACE2), the primary host cell receptor for SARS-CoV and SARS-CoV-2, was targeted to epithelial cells, since mouse ACE2 (mACE2) does not support virus binding as efficiently as hACE2 does. A study showed that SARS-CoV-2 is pathogenic in hACE2 Tg mice, but not in wild type mice. A mouse model would be useful for testing the efficacy of BCG-WT and BCG-disA-OE as vaccines against SARS-CoV-2 for multiple reasons: it is possible to test multiple routes of administration and carrying out studies in large numbers of animals; and reagents for the study of the immune response are widely available. Infection in Syrian hamsters (Mesocricetus auratus): Progression of infection by bacteria, viruses and parasites, including high consequence pathogens, parallels that observed in humans. Hamsters are therefore valuable in the pre-clinical development of vaccines and therapeutic drugs. Previous studies of SARS-CoV infection in golden Syrian hamsters have shown viral replication with peak viral titers in the lungs by 2 dpi, followed by rapid viral clearance by 7 dpi, and differences in virulence between SARS-CoV strains. Recently, it has been shown that SARS-CoV-2 infection in golden Syrian hamsters resemble features found in humans with mild infections.

Infection in mice: The K18-hACE2 transgenic mouse is susceptible to SARS-CoV and SARS-CoV-2 (26, 27). Depending on the inoculum, the mice survive 5-14 days before succumbing to coronavirus infection.

Time-to-death (TTD) study: 3 groups of 15 hACE2 transgenic mice each will receive either PBS, BCG, or BCG-disA-OE intradermally. After 6 weeks, the mice will be challenged with $2 \times 10^4$ PFU of SARS-CoV-2, a dose shown to be optimal in this and related mouse models. Time to death will be monitored daily. This experiment will be repeated twice: once using IV BCG vaccination and once using intratracheal BCG vaccination. In a recent study, IV BCG was shown to be dramatically superior to intratracheal administration, and the overall ranking of efficacy was IV>intratracheal>intradermal.

Organ burden study: immune responses and protective effects of BCG or BCG-disA-OE vaccination will be examined in mitigating SARS-Cov2 replication and lung pathology. 126 hACE2 transgenic mice will be vaccinated intradermally with 0.1 ml of PBS (sham vaccination), 105 CFU of either BCG-WT or BCG-disA-OE (42 mice in each of the 3 groups) and held for six weeks before challenge with SARS-CoV-2 intranasally with $2 \times 10^4$ PFU on day 0. 7 mice from each group will be sacrificed on days $-1$, 1, 3, 6, 9, and 12 post SARS-CoV-2 challenge. Lungs, spleens, and peripheral blood harvested from the groups at sacrifice will be evaluated for (i) organ weights, (ii) viral load by RT-PCR, (iii) viral infectivity on Vero-E6 cells, (iv) gross pathology, histopathology and IHC, and (v) cytokine expression with special emphasis on IL-6. Lung and spleen cell homogenates will be studied by FACS to monitor shifts in M1-, M2-macrophage populations and CD4, CD8 cells expressing pro-and anti-inflammatory markers (e.g., IFNg, FoxP3). Epigenetic and metabolic reprogramming changes (trained immunity) will be assessed. Non-lethal PET-CT imaging will be performed every 3 days on representative mice from the 3 groups to monitor disease progression and lung pathology at the Johns Hopkins Center for Infection & Inflammation Imaging Research (Ci3R). As with the TTD study, this experiment will be repeated twice: once using IV BCG vaccination and once using intratracheal BCG vaccination.

Infection in Syrian hamsters: The Syrian hamster model of SARS-CoV-2 infection is now established. Serial CT imaging of representative golden Syrian hamsters infected by SARS-CoV-2 revealed progressive pneumonitis detectable as early as day 2 post infection. Hematoxylin and eosin (H&E) staining of representative golden Syrian hamster lungs infected by SARS-CoV-2 revealed pneumocyte hyperplasia and neutrophilic inflammation when examined at day 7 post infection. Peak viral load in the lungs in infected hamsters is observed on 2 dpi with a decrease on 5 dpi. No infectious virus was detected on 7 dpi despite of the continued detection of high copies of viral RNA. Seventy-five Syrian hamsters will be vaccinated intradermally with 0.1 ml of PBS (sham vaccination), 105 CFU of either BCG-WT or BCG-disA-OE (25 hamsters in each of the 3 groups). They will be held for six weeks before challenge with SARS-CoV-2 intranasally with $5 \times 10^4$ PFU on day 0. Blood monocytes will be isolated for analysis of trained immunity markers before infection. Disease progression will be monitored in infected hamsters with measurement of body weight, temperature, and chest radiographs taken daily. 5 hamsters from each group will be sacrificed on $-1$, 1, 3, 5, and 7 days post SARS-CoV-2 challenge. Lungs, spleens, and peripheral blood harvested from the groups at sacrifice. Blood chemistry and hematology and coagulation parameters (activated partial thromboplastin time, prothrombin time, thrombin time, fibrinogen concentration, and Protein S and Protein C activity). Immune responses will be evaluated by measurement of cytokines, including IL-1β, IL-6, IFNγ, TNFα, Foxp3 and TGFβ by qRT-PCR. Viral loads will be detected Histopathological examination will be carried out in lungs and spleen to evaluate inflammatory cells and consolidation, and SARS-CoV-2 N protein.

Assessment of viral replication at from BAL and at necropsy. A GFP-tagged recombinant SARS-CoV-2 strain to add an additional modality for quantification of viral replication. Mouse ACE2 receptor does not efficiently bind SARS-CoV-2 and the human disease does not replicate well in normal mouse strains, which limits the use of inbred mice. The pathogenicity of SARS-CoV-2 in hACE2 transgenic mice has been reported to be milder compared to SARS-CoV. hACE2 Tg mice are hemizygous and are bred to wild type mice, since it is not known if homozygous mice are viable and fertile. Use of Ad-hACE2 viral delivery. Recently, it was reported the development of an Ad-hACE2 viral vector which may be used to enhance the susceptibility of non-transgenic mice to SARS-CoV-2.

Example 4

BCG and BCG-disA-OE Effect on Macrophages

Evaluate the role of macrophages in BCG and BCG-disA-OE modulation of SARS-CoV-2-mediated pathology in vitro. It is thought that upregulation of ACE2 receptors on macrophages by Type I IFN signaling might lead to direct interaction with SARS-CoV-2 to promote pro-inflammatory cytokine secretion, and that trained immunity changes induced by BCG-WT and BCG-disA-OE might exacerbate or attenuate the responses. This will be examined hypothesis using human peripheral blood mononuclear cells untreated, BCG-WT or BCG-disA-OE treated, evaluate and macrophage reprogramming, followed by infection with SARS-CoV-2 and analysis of virus titration, cytokine and chemokine responses.

It is becoming increasingly clear that macrophages play a critical role in SARS-CoV-2 mediated pathology. ACE2 expressing pulmonary epithelial cells infected by SARS-CoV-2 express high levels of chemo attractants that recruit inflammatory macrophages which in turn produce copious proinflammatory cytokines and chemokines contributing to the cytokine storm observed in severe SARS-CoV-2 pathology. A delay in anti-viral Type I IFN signaling promotes the recruitment and activation of macrophages in SARS-CoV infection, and early Type I IFN signaling prior to peak virus titers appears to abrogate this cascade of events in mice thereby ameliorating immunopathological disease. However, it is not clear if the same phenomenon occurs in SARS-CoV-2 infection. Trained immunity changes induced by BCG-WT and BCG-disA-OE could either exacerbate or attenuate these responses. For example, early Type I IFN signaling offered by BCG-disA-OE vaccination could ameliorate pathology. On the other hand, Type I IFN signaling could promote expression of ACE2 receptor on macrophages, which could be become secondary interaction partners for SARS-CoV-2 modulating disease outcome. Human lung macrophages have been shown to express ACE2. SARS-CoV-2 may also infect macrophages via other receptors or co-receptors such as DPP-4, which is a receptor for MERS-CoV. COVID-19 patients demonstrate a novel intermediate population of forward scatter (FSC)-high monocytes which were shown to comprise non-classical macrophages with mixed M1 and M2 phenotypes, and patients with high levels of FSC-high monocytes had higher disease severity. These data strongly suggest that SARS-CoV-2 leads to aberrant macrophages reprograms and that this reprogramming may contribute to cytokine storm and disease progression. These effects will be examined in vitro using human MDM.

Human peripheral blood mononuclear cells (PBMCs) will be isolated from whole blood from healthy donors. Monocytes will be isolated by magnetic activated cell sorting (MACS) using CD14-coated MicroBeads (Miltenyi®). They will be incubated with culture medium only (negative control), BCG-WT, or BCG-disA-OE for 3 h. After BCG exposure, cells will be washed and rested by incubation in culture medium for 3 days. Any induced expression of hACE2 receptor with and without BCG-WT or BCG-disA-OE treatment will be evaluated by flow cytometry or RT-PCR. Untreated and treated cells will be infected for 60 min with SARS- CoV-2 at MOI of 0.1 to 1 for viral replication kinetics or at a MOI of 2:1 for the analysis of cytokines and chemokines. Mock-infected cells will serve as controls. After incubation, viral inoculums will be removed, and the cells will be washed and incubated in macrophage serum-free medium. Samples of culture supernatants will be collected and stored at ±70° C. for virus titration or cytokine analysis. Viral titers in supernatant will be determined by TCID50 assay, RT-PCR and infectivity assays. Cell lysates will also be collected at 24 hours post-infection (hpi) or 48 hpi, for mRNA expression of SARS-COV-2 ORF1b and cytokines (IL-6, TNF1, IL-1b, IFN-g, IL-17 and chemokines such as CCL2, CCLA3, CCL5 and CXCL10).

Determination of whether enhanced induction of proinflammatory cytokines following viral infection in cells treated by BCG-disA-OE and BCG-WT is epigenetically mediated will be done by evaluating the promoter regions of the TNF-a and IL-6 genes for durable, antigen-independent epigenetic changes using chromatin immunoprecipitation (ChIP-PCR) assays and examining activating histone methylation mark H3K4me3 associated with the TNF-a and IL-6 promoters. It will also be determined whether chromatin repression mark (H3K9me3) at the same two promoters are reduced. Immunometabolic state of the macrophages infected with BCG-WT and BCG-disA-OE to examine increased intracellular glucose and lactate as compared to unvaccinated infected macrophages will be evaluated by LC-MS. the macrophage activation phenotype will be characterized to understand if WT and BCG-disA-OE strains elicit an increase in the population of classical macrophages (CD11b+ CD14+ CD16−) before and after viral infection. inflammatory macrophages (CD14+ CD16− HLA-DR+, TNF-a or IL-6-secreting, M1 macrophages) alternatively activated (CD163+ and CD206+ M2) macrophages and transitional or intermediate macrophages (CD11b+CD14+ CD16+CD68+, CD80+, CD163+, CD206+ secreting both IL-6, TNF-alpha, and anti-inflammatory IL-10) will be quantified.

In human, non-human primate and mouse tissues, ACE2 and TMPRSS2 co-expressing cells that provide entry to SARS-CoV-2 are lung type II pneumocytes, ileal enterocytes, and nasal goblet secretory cells. Although macrophages are not considered primary entry target cells, they are known to express ACE2 in patients with Covid-19 suggesting receptor upregulation most-likely mediated by Type I IFNs since ACE2 is a human interferon-stimulated gene. Studies in vitro will not replicate cross-talk between pneumocytes and macrophages, and between macrophages and other cells of the immune system including NK cells and T lymphocytes all of which collectively contribute to the pathology of Covid-19. These experiments will establish how the BCG-mediated changes prior to SARS-CoV-2 challenge of macrophages in cytokines, cell populations, epigenetic changes, and metabolomic changes subsequently alter post-challenge. These changes may be that beneficial, detrimental, or neutral.

Example 5

Materials and Methods for Examples 6-12

Bacterial strain and culture conditions: This study used commercially available Mycobacterium bovis (*M bovis*) *Bacillus Calmette*-Guérin (BCG)-Tice (Onco-Tice©, Merck) for immunization experiments. The lyophilized bacterial stock was resuspended in 1 ml of 7H9 Middlebrook liquid medium (Cat. B271310, Fisher Scientific®) supplemented with (OADC) (Cat. B11886, Fisher Scientific®), 0.5% glycerol (Cat. G55116, Sigma®) and 0.05% Tween-80 (Cat. BP338, Fisher Scientific®). The culture was streaked on 7H11 plate supplemented with oleic-albumin-dextrose-catalase (OADC) and a single colonies were picked and propagated in 7H9 Middlebrook liquid medium for preparation of seed-stock. Individual seed-stock vial was randomly selected from frozen stock and was subsequently propagated in 7H9 medium before immunization.

Cells and viruses: All cells were obtained from the American Type Culture Collection. Vero C1008 [Vero 76, clone E6, Vero E6] (ATCC® CRL-1586) cells were used for viral growth and determination of virus stock titers. Vero E6 cells were grown in EMEM with 10% fetal bovine serum (FBS), L-glutamine, and penicillin-streptomycin at 37° C. with 5% CO2. SARS-CoV-2/Wuhan-1/2020 virus (U.S. Center for Disease Control and Prevention) was provided by Dr. Andrew Pekosz. The viral stocks were stored at –80° C. and titers were determined by tissue culture infectious dose 50 (TCID50) assay.

Animals: In vivo experiments involving BCG vaccination and SARS-Co-V2 infection were carried out using male golden Syrian hamsters. Male golden Syrian hamsters (age 5 to 6 weeks) were purchased from Envigo. Animals were housed individually under standard housing conditions (68 to 76° F., 30 to 70% relative humidity, 12-h light/12-h dark cycle) in cages with proper bedding. After 7 days of acclimatization animals were intravenously vaccinated using live $5 \times 10^6$ C.F.U. of BCG-Tice in a total volume of 100 µl saline under ketamine (60 to 80 mg/kg) and xylazine (4 to 5 mg/kg) anesthesia administered intraperitoneally. Control animals received an equivalent volume of saline. Animals were challenged using $5 \times 10^5$ $TCID_{50}$ of SARS-CoV-2/Wuhan-1/2020 virus in 100 µof DMEM (50 µl/naris) through the intranasal route under ketamine (60 to 80 mg/kg) and xylazine (4 to 5 mg/kg) anesthesia administered intraperitoneally. Control animals received an equivalent amount of DMEM. Animals were randomly assigned to be euthanized at day 4 and day 7 in BCG vaccination+SARS-CoV-2 infected groups post SARS-CoV-2 infection. Body weights were measured at the day of infection (baseline) and endpoint, with daily measurement when applicable per group. At the endpoint animals were euthanized by isoflurane overdose, and tissues were harvested. Bronchoalveolar lavage (BAL) was obtained by cannulating the trachea with a 20-guage catheter. The lung was lavaged twice (each aliquot 1ml; calcium free PBS); total returns averaged 1.15 ml/animal. BAL was centrifuged at 600g for 5 min at 4° C.

Flow Cytometry analysis: For cellular immune profiling, cell surface staining was performed on single cells from hamster lung, spleen, blood, or BAL samples at the experimental end point. Lung and spleen tissues were harvested and stored in sterile PBS in individual tubes before single cell preparations. Blood was collected in EDTA containing tubes using cardiac puncture. BAL isolation was performed. RBC lysis of blood samples were performed using ACK lysis buffer for 5 minutes at room temperature to remove all the RBCs among leukocytes. A mouse lung dissociation kit was used for preparation of single cells as per manufacturer's instruction using a gentleMACS™ Octo Dissociator with heaters. Cells were passed through a 70 µm filter and washed twice using ice-cold PBS followed by RBC lysis using ACK lysis buffer at room temperature for 5 minutes. The cell viability was determined using Trypan blue dye staining and determine total live cells per lobe. For surface staining a total of 5 million cells per animal lung were used in this study. For blood samples and BAL total cells were used for antibody staining. Briefly, cells were washed again using ice-cold PBS and stained using Zombie Aqua™ Fixable Viability Kit for 20 min at room temperature. Cells were subsequently washed and resuspended in FACS buffer (1% BSA, 2 mM EDTA in PBS) and incubated for 30 minutes at 4° C. in block buffer consisting of PBS and 2% FBS, 2% normal rat serum and 2% normal mouse serum prior to surface staining. Cells were again washed and stained with conjugated primary antibodies as per manufacturer's protocol. Following antibodies were used for cell surface staining: anti-CD3, anti-CD4, anti-CD11b, and anti-RT1D. Cells were subsequently fixed using IC fixation buffer for 60 minutes at 4° C. Cells were washed three times using FACS buffer and acquired using BD LSRII with FACSDiva Software. Data analyses was carried out using FlowJo® (v10).

Single Cell RNA-seq Sample and Library Preparation: For single-cell RNA seq (scRNA-seq) of lung tissue derived single cells right whole right lung superior lobe was isolated from each animal. For single cell preparation, mouse lung dissociation kit was used with some additional modifications. Following single cell preparation, cell suspensions were applied to a MACS Smart Strainer (70 µm) and washed twice with 10 ml of DMEM. Cells were pelleted by spinning at 300×g for a total of 7 minutes at 4° C. Cells were resuspended in 1 ml DMEM containing DNase (final concentration 100 µg/ml) for 5 minutes at room temperature. Cells were washed by adding 10 ml sterile PBS containing 0.5% BSA and pelleted at 4° C. The RBC lysis was carried out using 1X RBC lysis solution in a total volume of 1 ml for 10 minutes at 4° C. Cells were resuspended in 10 ml chilled DPBS containing 0.5% BSA and pelleted subsequently. Cells were filtered using 35 µm Falcon cell strainer and transferred to a 2mllo-binding tube in a total volume of 1ml DPBS containing 0.04% BSA. Cell were subsequently counted using trypan blue dye exclusion assay to determine cell viability and total cell number.

BCG bacteria used for vaccination: BCG-STING(Tice) also called BCG-disA-ice), which is described in Example 1, was used in this study. The wild type BCG used was BCG-Tice (Onco-Tic©).

Single-cell data integration and clustering: 10X Single Cell RNA-seq Chromium Chip G 5' Library kits (10X Genomics®) were used to capture immune repertoire information and gene expression from the same cell in an emulsion-based protocol at the single-cell level. Cells and barcoded gel beads were partitioned into nanolitre-scale droplets using the Genomics Chromium platform to partition up to 10,000 cells per sample followed by RNA capture and cell-barcoded cDNA synthesis using the manufacturer's standard protocols. Libraries were generated and sequenced on an Illumina NovaSeq instrument using 2×150-bp paired end sequencing.

Single-cell data pre-processing and quality control: Cell Ranger v3.1.0 was used to demultiplex the FASTQ reads, align them to the hamster genome, and extract their cell and unique molecular identifier (UMI) barcodes. The output of this pipeline is a digital gene expression (DGE) matrix for each sample, which records the number of UMIs for each gene that are associated with each cell barcode. The quality of cells was then assessed based on (1) the number of genes detected per cell and (2) the proportion of mitochondrial gene/ribosomal gene counts. Low-quality cells were filtered if the number of detected genes was below 250 or above 3× the median absolute deviation away from the median gene number of all cells. Cells were filtered out if the proportion of mitochondrial gene counts was higher than 10% or the proportion of ribosomal genes was less than 10%. For single-cell VDJ sequencing, only cells with full-length sequences were retained.

Dissociation/stress associated genes mitochondrial genes (annotated with the prefix 'MT-'), high abundance lincRNA genes, genes linked with poorly supported transcriptional models (annotated with the prefix 'RP-') and TCR (TR) genes (TRA/TRB/TRD/TRG, to avoid clonotype bias) were removed from further analysis. In addition, genes that were expressed in less than five cells were excluded.

Single-cell data integration and clustering: Seurat (3.1.5) was used to normalize the raw count data, identify highly variable features, scale features, and integrate samples. PCA was performed based on the 3,000 most variable features identified using the vst method implemented in Seurat. Dimension reduction was done using the RunUMAP function. Cell markers were identified by using a two-sided Wilcoxon rank sum test. Genes with adjusted P<0.05 were retained. Clusters were labelled based on the expression of the top differential gene in each cluster as well as canonical immune cell markers. Global clustering on lymphocytes, monocyte/macrophages, and granulocytes were performed using same procedure. Clusters were visualized using Uniform Manifold Approximation and Proj ection (UMAP).

Hematoxylin and eosin (H & E) staining: Formalin-fixed paraffin embedded hamster lung sections were stained with hematoxylin-eosin (H&E) for analysis. Lung tissue was scored using a panel of specific lung inflammation parameters according to criteria previous published on animal models of acute pneumonia. All examinations were performed by a board-certified pulmonary pathologist.

Immunohistochemistry (IHC), statistics and histopathological scoring: Immunohistochemistry was performed on FFPE lung tissue sections for CD3 using an automated Ventana Discovery (Roche®) autostainer. Heat induced antigen retrieval was achieved using ETDA pH9 solution (CC1, Roche®). Primary antibody for CD3 was incubated for 30 m at 4 C and detection was achieved using UltraView DAB detection kit (Roche®). IHC protein expression was scored by a board-certified pulmonary pathologist blinded to cohort status or treatment group. CD3 membranous staining was evaluated separately in perivascular or peribronchial inflammation, bronchial epithelium, alveolar wall as well as pneumocytes and in areas of pneumonia (when present) or alveolar spaces (in absence of pneumonia). CD3 staining was scored as 1+ (scattered single cells), 2+ (cells in clusters or sheets with at least 2 layers) or 3+(several clusters or sheets). Scores were then quantified using a point system (focal 1+=0.5, 1+=1, focal 2+=1.5, 2+=2, 3+=3) and total points were analyzed between treatment groups. Total CD3 expression was calculated by combining all point scores for all criteria. Statistical analysis was performed between groups at each timepoint (day 4 post infection and day 7 post infection) using Welsh's t-test.

SARS-CoV-2 Viral Quantification: Viral RNA RT-qPCR RNA from hamster lung and trachea homogenates was extracted using Zymo® Quick RNA microPrep kit (Zymo Research®) according to the manufacturer's protocol. On average, 600 ng of total RNA was extracted per sample. A QIAamp® Viral RNA mini kit (Qiagen®) was used to isolate RNA from supernatants according to the manufacturer's protocol. cDNA was synthesized from the viral RNA using qScript® cDNA SuperMix (Quantabio®) following the manufacturer's protocol. The cDNA was quantified by RT-qPCR on a StepOnePlus Real Time PCR system (Applied Biosystems®) with TaqMan Fast Advanced Master Mix (Applied Biosystems®). SARS-CoV-2 RNA was detected using premixed forward (5'-TTACAAACAT-TGGCCGCAAA-3' SEQ ID NO:1) and reverse (5'-GCGCGACATTCCGAAGAA-3' SEQ ID NO:2) primers and probe (5'-FAM-ACAATTTGCCCCCAGCGCTTCAG-BHQ1-3' SEQ ID NO:3) designed by the CDC as part of the 2019-nCoV CDC Research Use Only (RUO) kit (Integrated DNA Technologies®,) to amplify a region of the SARS-CoV-2 nucleocapsid (N) gene. PCR conditions were as follows: 50° C. for 2 min, 95° C. for 2 min, followed by 45 cycles of 95° C. for 3 s and 55° C. for 30 s. Serially diluted (10-fold) plasmid containing the complete SARS-CoV-2 N gene (Integrated DNA Technologies®) was measured to generate a standard curve for quantification of viral RNA copies. The limit of detection for the assay was $1\times10^1$ RNA copies. For cell lysates, viral copies were normalized to the human RNase P (RP) gene using premixed forward (5'-AGATTTGGACCTGCGAGCG-3' SEQ ID NO:4) and reverse (5'-GAGCGGCTGTCTCCACAAGT-3' SEQ ID NO:5) primers and probe (5'-FAM-TTCTGACCT-GAAGGCTCTGCGCG-BHQ-1-3' SEQ ID NO:6) included in the same 2019-nCoV CDC RUO kit.

CT and PET imaging: Live hamsters were imaged inside in-house-developed, sealed biocontainment devices compliant with BSL-3, as previously reported. Seven days postinfection, SARS-CoV-2-infected male (n=12), female (n=12), placebo-treated male (n=13), and E2-treated male (n=13) hamsters underwent chest CT using the nanoScan positron emission tomography (PET)/CT (Mediso USA) small animal imager. CT images were visualized and analyzed using the VivoQuant 2020 lung segmentation tool (Invicro). Briefly, an entire lung volume (LV) was created, and volumes of interests (VOIs) were shaped around the pulmonary lesions using global thresholding for Hounsfield Units (HU) ≥0, and disease severity (CT score) was quantified as the percentage of diseased lung in each animal. The investigators were blinded to the group assignments. For PET imaging $^{18}$F-FDG was synthesized in-house as described previously yielding >90% radiochemical purity. SARS-CoV-2-infected hamsters were given ~10.22 MBq/hamster via the surgically implanted central venous catheter. A 20-min PET acquisition and subsequent CT were performed using the nanoScan PET/CT (Mediso). Given that SARS-CoV-2 is designated as a BSL-3 pathogen, live SARS-CoV-2-infected animals were imaged inside transparent and sealed biocontainment cells developed in-house, compliant with BSL-3 containment and capable of delivering air-anesthetic mixture to sustain live animals during imaging. For lung segmentation and image analysis, a multi-atlas lung segmentation (MALS) algorithm was used to create the whole lung volumes of interest (VOI). A reference library was generated from a selection of study images that included SARS-CoV-2-infected hamsters in various stages of lung disease. A bounding box for the lung VOI was generated using a combination of rigid and affine transformations followed by a high-dimensional deformable registration technique inside this bounding box to efficiently refine the linear mapping accuracy. The propagated labels were merged using a weighted voting-based label fusion technique. A local search algorithm was also used to improve robustness against registration errors. Pulmonary lesions were defined using a global Hounsfield units (HU) threshold≥0. The data are represented as CT score [(pulmonary lesions volume/whole lung volume)×100]. The investigators analyzing the CT were blinded to the group assignments. VivoQuantTM 2020 (Invicro) was used for visualization and quantification. Scatter and attenuation corrections were applied to the PET data and multiple VOIs were manually drawn per animal using the CT as a reference.

Example 6

Experimental Design

Experimental design: Groups of hamsters were vaccinated intravenously with either PBS (non-vaccinated), or $5 \times 10^6$ CFU of BCG-Tice, or $5 \times 10^6$ CFU of BCG-STING-Tice. 30 days later they were challenged with $5 \times 10^5$ $TCID_{50}$ units of SARS-CoV-2 (Wuhan-1/2020) by the intranasal route. At d4 and d7 post-challenge animals were sacrificed for analysis. Group 1 was BCG-WT (vaccinated and no SCV2 exposure), Group 2 was SCV2 only (non-vaccinated and SCV2 exposure, sacrificed D4 and D7), Group 3 was BCG-WT and SCV2 (vaccinated and SCV2 exposure), and Group four was BCG-STING and SCV2 (vaccinated and SCV2 exposure). In certain experiments, unmanipulated, healthy, age-matched hamsters were also studied.

Example 7

Histological Analysis of Lung Pathology

BCG vaccination reduces lung pathology in SCV2-infected hamsters. To determine whether prior BCG vaccination alters the course of SCV2 infection in this non-lethal hamster model, lung histopathologic changes at d4 and d7 were evaluated. As shown in FIG. 4B, bronchopneumonia was present in 100% of unvaccinated hamster lung high power fields (HPF) at both d4 and d7 but was absent in all BCG-vaccinated hamster HPF and d4 and found in only 25% of HPFs on d7. Similarly, 100% of unvaccinated hamster HPFs showed neutrophilic infiltration at d4 while only 50% of BCG-vaccinated hamsters showed this finding (data not shown), and unvaccinated hamster lungs also showed infiltrating lymphocytes (data not shown). In contrast BCG vaccination promoted macrophage infiltration (80% of HPFs at d4) while only 60% of HPFs in unvaccinated animals showed this finding (FIG. 4C). As expected, all BCG vaccinated HPFs showed granuloma formation, a phenomenon that was uniformly absent in unvaccinated animals (FIG. 4D). These results conclusively demonstrate that prior BCG vaccination reduces SCV2-induced bronchopneumonia with its concomitant neutrophilic infiltration while simultaneously enhances macrophage lung recruitment.

BCG-STING vaccination reduces lung pathology in SCV2-infected hamsters and is superior to BCG-WT for certain pathologic markers. To compare BCG-STING vaccination to that of BCG-WT, lung histopathologic changes at d4 and d7 were evaluated. As shown in FIG. 18A, bronchopneumonia was reduced from 100% to 0% at day 4 by both BCG-STING and BCG-WT. However, it remained at 0% at day 7 in BCG-STING-vaccinated animals but was present in 25% of HPFs with BCG-WT vaccinated hamsters on d7. Both BCG strains reduced neutrophilic infiltration at d4 to 50% at day 4 (FIG. 18B). Regarding macrophage infiltration, BCG-STING vaccination promoted more macrophage infiltration (100% of HPFs at d4) while only 80% of HPFs in BCG-vaccinated and 60% of unvaccinated animals showed this finding (FIG. 18C). Next, interstitial inflammation, a potential marker of an effective immune response against SCV2 but also a potential contributor to immunopathology was examined. While both BCG-STING and BCG- WT vaccinated animals had more interstitial inflammation at day 4 than unvaccinated animals, BCG-STING vaccinated hamsters showed a high degree of interstitial inflammation resolution at day 7 (only 40% of HPFs) compared with BCG-WT vaccinated animals (100%) (see FIG. 18D). Regarding lymphocyte recruitment to the lungs in the face of SCV2-associated lymphopenia, 100% BCG-STING vaccinated hamster HPFs showed this attribute at day 4 while it was seen in only 50% of BCG-WT-vaccinated hamster lung HPFs at day 4 (FIG. 18E). Next, perivascular inflammation was examined and found that BCG-STING vaccinated hamsters had 0% perivascular inflammation at day 4 despite the fact that BCG-WT-vaccinated and unvaccinated animals showed this phenomenon in 50% and 20% of HPFs, respectively (FIG. 18F). BCG-STING also showed lower intra-alveolar (FIG. 18F) and peribronchial (FIG. 18G) inflammation than BCG-WT at day 4. These results demonstrate that BCG-STING vaccination confers notable lung histopathologic difference compared with BCG-WT vaccination in experimental SCV2 infection in hamsters.

Example 8

Flow Cytometry

BCG vaccination blunts SCV2-mediated lung T cell lymphopenia, enhances macrophage lung recruitment, and reduces lung infiltration by granulocytes. To assess overall cell population fluxes in hamster lungs multicolor flow cytometry was performed. In the BCG-WT experiment, it was found that lung T cell (CD3+ cells) were dramatically boosted by BCG vaccination in the absence of SCV (45% of live cells) compared to age-matched healthy animals (18%) (data not shown). Similar results were reproduced for BCG-STING animals (FIG. 5A). In unvaccinated animals challenged with SCV2, the total lung CD3+population dropped substantially at d4 and d7 to 4-6%; while BCG vaccinated, SCV2 challenged animals showed nearly twice as many CD3+ cells (10-12%) at these same time points. This same effect of BCG preventing T cell depletion in the lung was present to an even greater among lung CD4+ T cells (data not shown). Similarly, BCG vaccination in the absence of SCV2 infection prompted a pronounced macrophage recruitment to the lung (55% of live cells) compared to healthy animals (5%) (data not shown). And while SCV2 infection led to a modest macrophage lung recruitment by d7 (12% of live cells), animals previously BCG vaccinated showed highly elevated macrophage populations in the lungs (30% of live cells) on both d4 and d7. In contrast, in considering granulocytes, it was found that SCV2-challenged, unvaccinated hamster lungs revealed dramatic infiltration by PMNs on d4 (80% of live cells) and d7 (72%) (data not shown) in keeping with the profound bronchopneumonia observed in FIG. 4A. Pre-vaccination with BCG had the effect of limiting this granulocytic infiltration to levels of 30% on d4 and 32% on d7 which were levels essentially equivalent to those in the lungs of healthy age-matched hamsters.

It was found that BCG-STING vaccinated, SCV2 challenged animals showed nearly twice as many CD3+ cells (-10%) than did unvaccinated, SCV2 challenged hamsters (4-6%) (FIG. 5A-D). This same effect of BCG-STING preventing T cell depletion in the lung was present to an even greater among lung CD4+ T cells; at d4 unvaccinated animals showed an average of 28% CD4+ T cells while BCG-STING vaccinated animals showed an average of 48% (FIG. 5B) and at d7 unvaccinated animals showed 50%

CD4+ T cells while BCG-STING vaccinated had an average of 70%. Similarly, BCG-STING vaccination in the absence of SCV2 infection prompted a pronounced macrophage recruitment to the lung (39% of live cells) compared to healthy animals (5%) (FIG. 5C). And while SCV2 infection led to a modest macrophage lung recruitment by d7 (12% of live cells), animals previously BCG-STING vaccinated showed highly elevated macrophage populations in the lungs at 25% of live cells on d4 and 41% of live cells on d7. In contrast, in considering granulocytes, it was found that SCV2-challenged, unvaccinated hamster lungs revealed dramatic infiltration by PMNs on d4 (80% of live cells) and d7 (72%) (FIG. 5D) in keeping with the profound bronchopneumonia observed in FIG. 4A. Pre-vaccination with BCG had the effect of limiting this granulocytic infiltration to levels of 33% on d4 and 20% on d7 which were levels essentially equivalent to those in the lungs of healthy age-matched hamsters.

Example 9

Droplet-Based Single Cell RNA Sequencing

Single cell transcriptional profiling in lung cells in BCG vaccinated and unvaccinated hamsters: The effects of BCG immunization in SARS-CoV-2 infected hamsters were examined in the hamster lungs using droplet-based single cell RNA sequencing (10X Genomics®) during the peak (day 4) and resolution (day 7) phases of COVID-19. In the BCG-WT experiment, a total of 13 hamsters were evaluated in the following three groups: BCG vaccination only (3 animals), SARS-CoV-2 infection only (2 animals on d4; 2 on d7), and BCG vaccination with SCV2 challenge (3 animals on d4; 3 on d7). Sequencing was performed in a total of 194,536 cells, and after filtering out low-quality cells 150,516 cells were analyzed (Table 2). The mean number of cells analyzed per animal in BCG vaccinated lungs (14,284), SARS-CoV-2 infected lungs (10,524), BCG-vaccinated+ SARS-CoV-2 infected lungs (10,928) and the BCG-STING vaccinated plus SARS-CoV-2 infected lungs (10,642) showed no significant difference. To maximize resolution of the complete tissue response rather than just immune cells, no immune cells enrichment analysis was performed. All high-quality cells were integrated in an unbatched dataset, corrected for read-depth, and then subjected it principal component analysis.

TABLE 2

| CELL COUNTS FOR SCRNASEQ | | | |
|---|---|---|---|
| CELLS SEQUENCED PER ANIMAL (MEAN ± SEM) | | | |
| BCG-ONLY (3 ANIMALS) | SCV2 only (2 animals d4; 2 animals d7) | BCG-SCV2 (3 animals d4; 3 animals d7) | BCG-STING-SCV2 (3 animals d4; 3 animals d7) |
| 17,575 ± 2891 | 12,876 ± 967 | 15,050 ± 1186 | 14,523 |
| CELLS ANALYZED PER ANIMAL* (MEAN ± SEM) | | | |
| 14,284 ± 2644 | 10,524 ± 779 | 10,928 ± 1194 | 10,642 |

*AFTER FILTERING OUT LOW QUALITY CELLS SUCH AS EMPTY DROPLETS, DOUBLETS, STRESSED OR DEAD CELLS

Example 10

Features Of Lymphoid, Myeloid, And Non-Immune Cell Types in BCG-Vaccinated, SCV2-Infected Hamsters BCG reverses lymphopenia, macrophage depletion, and loss of structural cell types due to SCV2 infection: Using graph-based clustering of uniform manifold approximation and projection (UMAP), transcriptomes of 14 major cell types or subtypes comprising 5 lymphoid cell types (T cells, pro T cells, NK cells, B cells and plasma cells), 4 myeloid cell types (granulocytes, macrophages, pro-macrophages, and dendritic cells), and 5 non-immune cell types (erythrocytes, alveolar type 2 [AT2] cells, ciliated cells, endothelial cells, and dying cells), were identified and these constituted more than 98% of total cells across all samples (data not shown). These cell clusters were homogenously distributed across all animal lungs at both timepoints. These distinct 14 cell clusters were represented across all samples and were based on the expression of well-defined canonical genes (data not shown).

Similarly for BCG-STING, by UMAP, transcriptomes of 11 major cell types or subtypes including 4 lymphoid cell types (T cells, NK cells or NKT, B cells, and plasma cells), 3 myeloid cell types (granulocytes, macrophages, and dendritic cells), and 4 non-immune cell types (alveolar type 2 [AT2] cells, ciliated cells, endothelial cells, and fibroblasts), were identified and these constituted more than 98% of total cells across all samples (data not shown). These cell clusters were homogenously distributed across all animal lungs at both timepoints. These distinct 11 cell clusters were represented across all samples and were based on the expression of well-defined canonical genes (data not shown).

At both d4 and d7 following SCV2 infection, significant depletion of T lymphocytes and macrophages was observed as well as loss of key lung structural cells such as AT2 cells and endothelial cells in hamster lungs. In contrast, hamsters vaccinated with BCG or BCG-STING maintained high levels of T lymphocytes, AT2 cells, and endothelial cells, and both increases in macrophage numbers as well as complexity of macrophage subsets.

BCG and BCG-STING expand T helper, T reg, and plasma cell populations during SCV2-infection. Next, subset analyses were performed to evaluate lung immune cells during SCV2 infection in vaccinated and unvaccinated hamsters in both experiments. For BCG-WT, among the CD4+ T cells in hamster lungs, the T memory markers Tcf7 and Lef1 and the Treg markers Foxp3 and Ikzf2 were used to segregate total CD4+ T cells into T memory, Treg, and T helper cells yielding a total of 7 subsets of lymphocytes (T memory, Treg, T helper, pro T cells, NK cells, B cells and plasma cells). The relatively high expression of Tbx21 (Tbet), Infg, and Tnf by this T helper population implied that they are type 1 helper T cells (Th1). No significant populations of RORyt/Stat3 (Th17) or GATA-3/Stat5 (Th2)-expressing CD4+ T cells were found. No CD8+ T cells were present in any of the hamster groups.

It was found that while plasma cells comprised a minor lung population in BCG-only-treated hamsters, they were uniquely expanded in BCG-vaccinated, SCV2-challenged animals (data not shown). Additionally, it was observed that SCV2 infection significantly reduced the populations of T helper and Treg cells in the lung compared with BCG-only-treated hamsters, and that in BCG vaccination promoted the maintenance of high levels of T helper and Treg cells in the lung despite ongoing SCV2 infection. These results indicated that BCG vaccination skew hamster lung CD4+ T cell responses to Th1 and Treg expression (with little to no Th17 or Th2 expression), that SCV2 suppresses Th1 and Treg lung population, and that SCV2-infected animals previously BCG-vaccinated are able to maintain high levels of Th1 and Treg cells.

Figure 6:
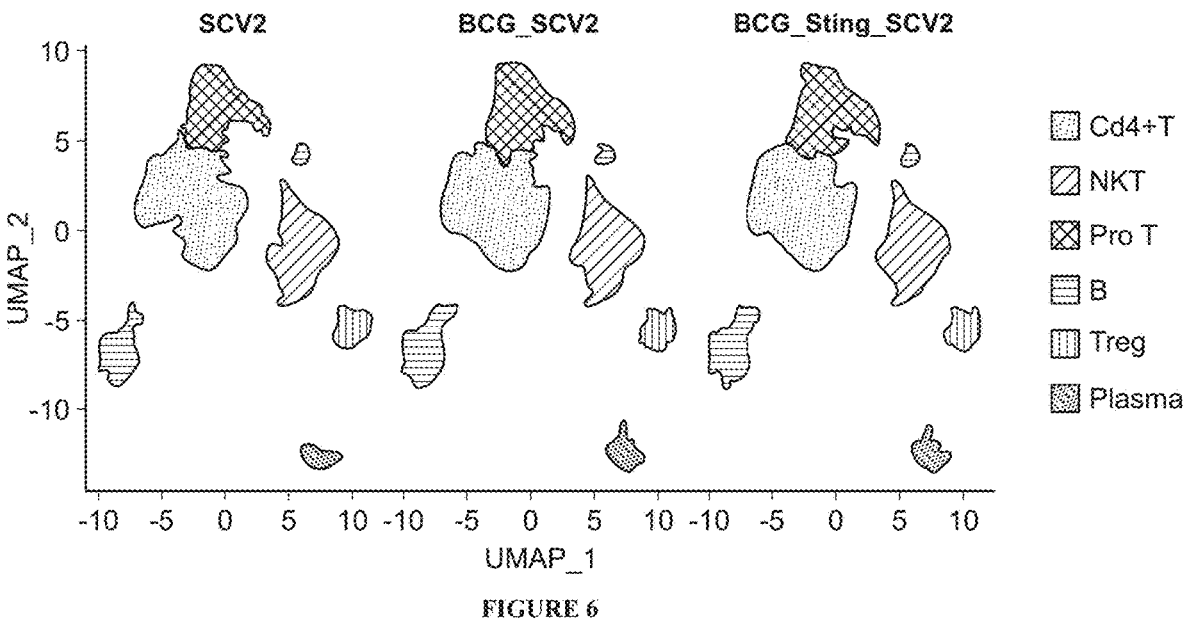
FIG. 6 shows graph-based clustering of uniform manifold approximation and projection (UMAP) plots for 6 lymphoid cell types for each treatment group.

For BCG-STING, 6 subsets of lymphocytes (CD4+ T cells, NKT cells, Pro T cells, B cells, Treg cells, and plasma cells) were analyzed as shown in FIG. 6. The BCG-STING data analysis did not include "BCG-only-noSCV2-challenge" making it a less complex dataset with fewer cell types.

Figure 7A:
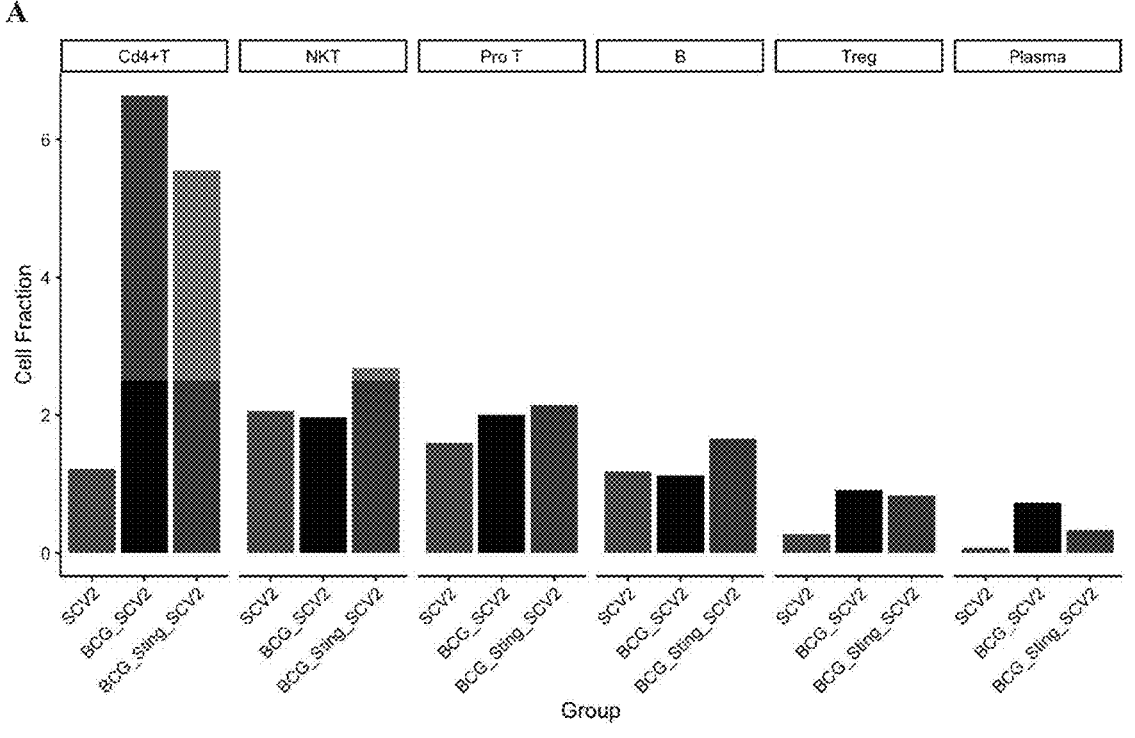

BCG-STING recruited more NTK cells and more B cells to the lung that BCG-WT (FIG. 7A-B). In the BCG-STING analysis, it was also found that both BCG and BCG-STING recruited more CD4+ T cells (FIG. 7A-B).

Figure 7C:
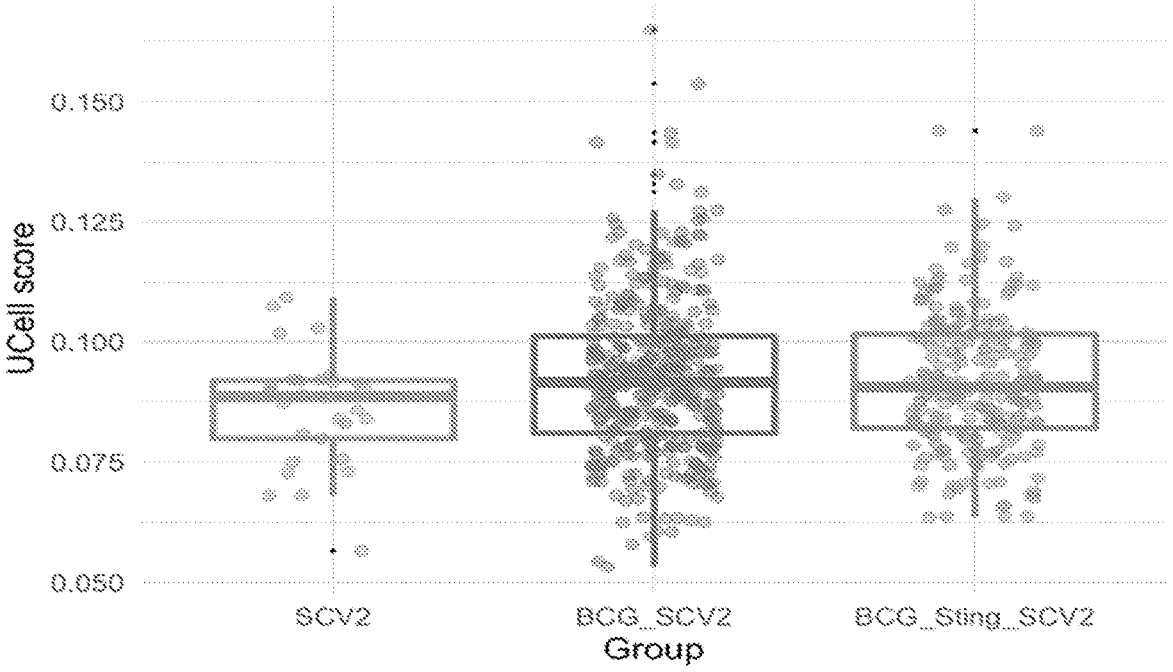

BCG and BCG-STING reduce interferon responses, accentuate MHC II antigen presentation and immunoglobulin production among lymphoid cells during SCV2 infection. To further investigate the transcriptomic changes among lung lymphoid cells differentially regulated genes (DEGs) were identified by comparing BCG-vaccinated, SCV-infected animals with those solely infected with SCV2 within key lymphoid cell types (FIG. 7C). For BCG-WT, it was found that BCG vaccination strongly upregulated antigen presentation genes such as Cd74, H2-Ab1, and H2-Ea in both T helper and Treg cell populations (data not shown). For BCG-STING, analysis was limited to CD4+ T cells (not broken down by T helper, Treg). However, in both cases, the following applies: Cd74 encodes the MHC class II HLA-DR antigen-associated invariant chain and is a known receptor for macrophage migration inhibitory factor (MIF), while prominently expressed by myeloid cells and B cells, CD74 is known to be expressed on CD4 T cells and its expression on T cells is upregulated in certain disease states such as T cell lymphomas and in lymphadenosis.

For BCG-WT, also observed was a strong interferon induced response in lung T helper, Treg and plasma cells in unvaccinated SCV2-infected hamsters including Isg15 (encoding a secreted 17 kDa protein induced by type I IFN) and the IFN-induced GTP-binding protein encoding genes Mx1 and Mx2 (both of which are known to be associated with antiviral immune responses. Gzmb, encoding granzyme B (a serine protease associated with cytolytic activity) was also strongly induced by SCV2-infection alone in lung T helper and Treg cells. Importantly, the strong expression of these IFN-inducible genes (Isg15, Mxl, Mx2) and Gzmb was completely reversed in BCG vaccinated SCV2-infected hamsters suggesting that BCG reduces pro-inflammatory responses which may lead to lung pathology during SCV2 infection (FIG. 11A-B). For BCG-STING, analysis was limited to CD4+T cells but the same analysis is valid (FIG. 10A-B).

For BCG-WT, it was also found that Cd74 (MHC class II HLA-DR antigen-associated invariant chain) was also strongly induced by BCG vaccination in plasma cells. Accordingly, the gene signature scores in lung plasma cells from hamsters were evaluated and found that genes associated with immunoglobulin production were elevated in both the BCG-no SCV2 and the BCG-SCV2 group while this parameter was reduced in plasma cells from unvaccinated hamsters infected with SCV2 (data not shown). For BCG-STING, BCG-STING and BCG-WT showed similar immunoglobulin gene upregulation (FIG. 7C). These findings support the conclusion that BCG or BCG-STING vaccination promotes both antigen presentation and immunoglobulin production, processes that may account for reduced SCV2 immunopathology.

Figure 8A:
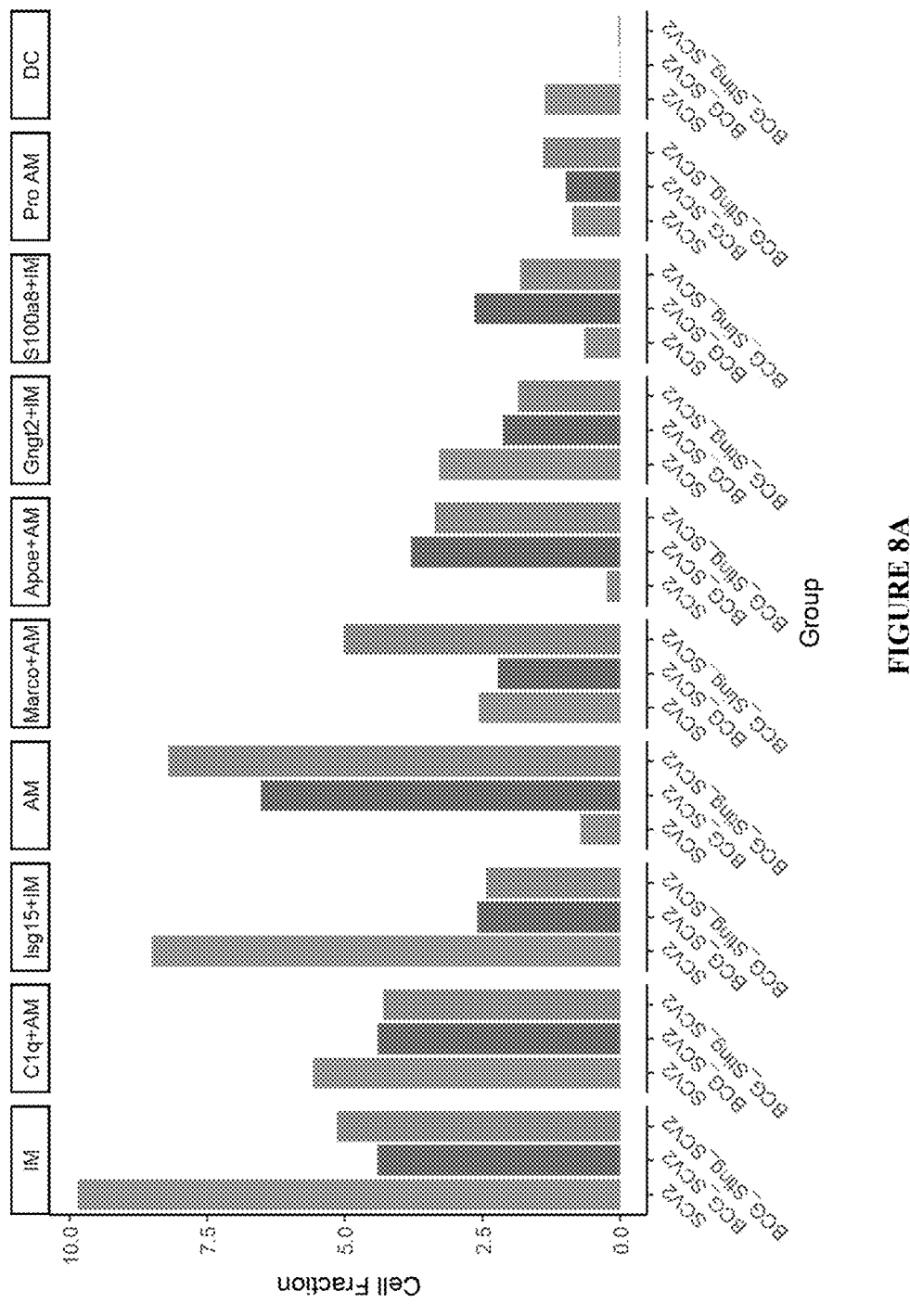
FIGS. 8A-B show cell fraction and differentially regulated genes (DEGs).
Figure 8B:
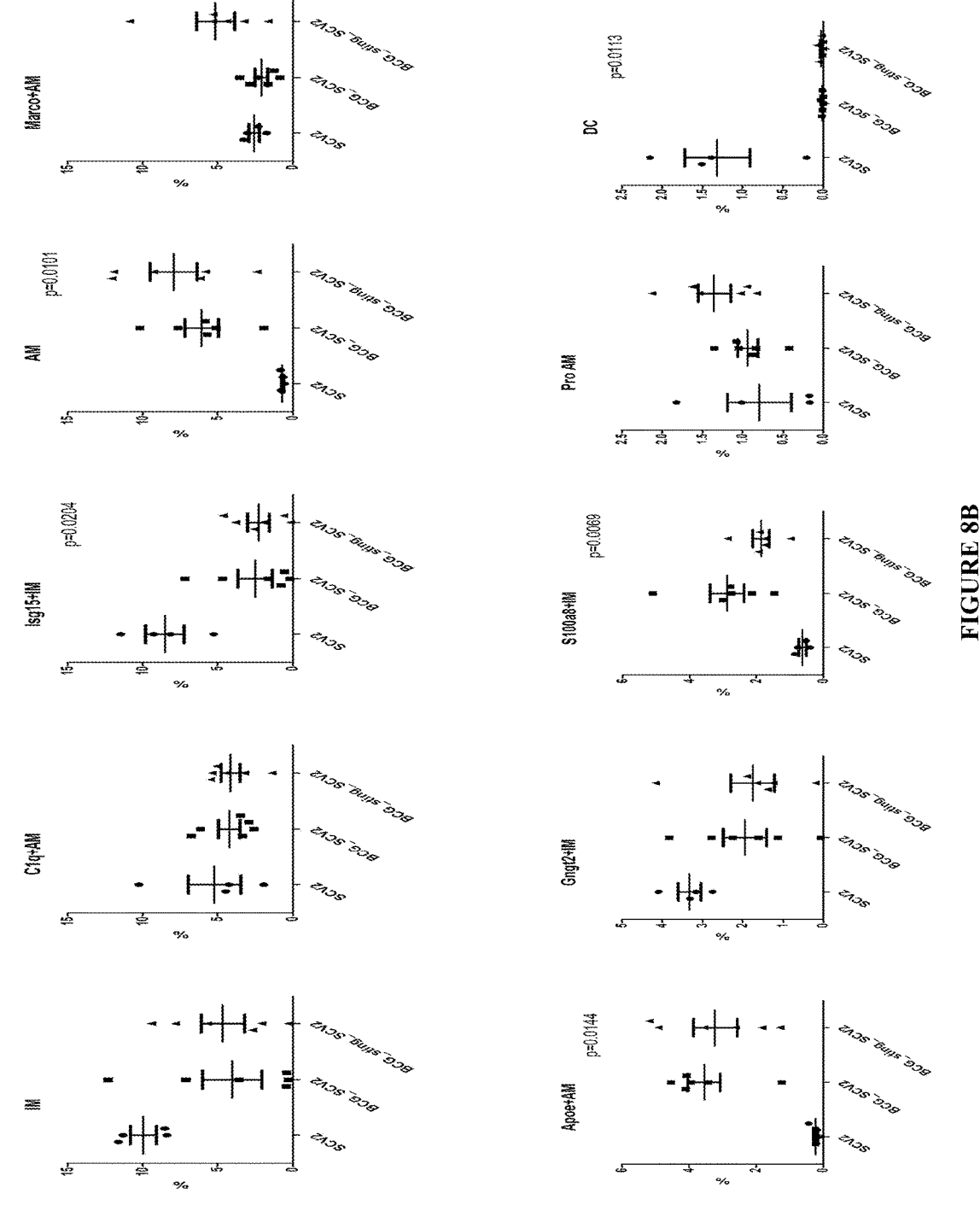

Features of macrophage and dendritic cell populations in BCG-vaccinated, SCV2-infected hamsters and BCG-STING-vaccinated, SCV2-infected hamsters. For BCG-WT, subset analysis of macrophage and dendritic cell populations revealed 9 distinct subsets defined by the canonical markers (data not shown). For BCG-STING, subset analysis of macrophage and dendritic cell populations revealed 10 distinct subsets defined by the canonical markers (instead of C1q+ Apoe+ AM, they were more distinct, so there is C1q+ AM and also Apoe+ AM) (data not shown). Alveolar macrophages are known to be important scavenging cells that phagocytose pathogens and debris but are relatively immunotolerant. For BCG-WT, it was found that mature alveolar macrophages could be separated into two clusters AM and Marco-expressing AM (Marco being scavenger receptor associated with recognition of pathogens and apoptotic cells). Importantly, BCG vaccinated, SCV-challenged animals maintained high levels of AMs, while in the absence of vaccination, SCV-infected hamsters showed a high degree of AM depletion (data not shown). For BCG-STING, it was found that BCG-STING recruited more AM and more Macro+ AM to the lung than BCG-WT (FIG. 8A-B).

Interstitial macrophages (IM) are thought to be recruited from the periphery to the lung and are more inflammatory than AMs. In addition to traditional IMs, also identified were 3 IM subtypes characterized by high-level expression of Isg15, Gngt2 (guanine nucleotide binding protein subunit T2), or S100a8 (calgranulin A). It was noteworthy that three of the interstitial macrophage subsets (IM, Isg+IM, and Gngt+ IM) were strongly induced in the lungs of unvaccinated SCV2-infected hamsters, while BCG-vaccination reduced their abundance significantly. These observations support the notion that BCG vaccination leads to an elevated setpoint of scavenging AM in the lungs, but during SCV2 infection it prevents excess recruitment of pro-inflammatory IM cells and IM subtypes which may be involved in SCV2-mediated lung immunopathology.

For BCG-WT, analysis of DEGs in AM and Isg15+ IM showed that in unvaccinated animals infected with SCV2, there was high transcription of IFN-associated genes (eg Isg15, Irf7, Mxl, see Fig_violin) as was observed in lymphoid cells, and this was accompanied by chemokine-encoding genes (cc12, cc112, cc14) and associated with lymphocyte activation (Slamf9), all consistent with ongoing inflammatory responses. However, in vaccinated animals challenged with SCV2, the predominant DEGs were shifted towards those involved in metabolic and repair processes (eg, ubd encoding ubiquitin, ppal encoding pyrophosphatase 1, cdo encoding cysteine dioxygenase) or complement factor expression (C1qa, C1qc) as might be expected in a less inflammatory, repair-oriented environment (FIG. 12A-B). Focused analysis of IFNy response gene signature scores revealed that for virtually all 9 myeloid cell subsets, BCG-vaccinated animals showed reduced expression, including for Isg15+ IMs which had the highest levels of IFNγ expression (data not shown).

For BCG-STING analysis was limited to AM (not AM and Isg15+IM). However, the conclusions are the same as above, both BCG-WT and BCG-STING shift gene expression away from IFN processes and towards metabolic and repair processes. (FIG. 8A-B).

Features of granulocytes in BCG-vaccinated, SCV2-infected hamsters and in BCG-STING-vaccinated, SCV2-infected hamsters. For BCG-WT, the dataset included large numbers of granulocytes, and 6 well-demarcated clusters were identified based on the canonical genes Il1b, Il1rn, Isg15, Camp, and Fcnb encoding IL-1b, IL-1 receptor antagonist, IFN-stimulated gene 15, cathelicidin (antimicrobial peptide), and ficolin B (lysosomal protein), respectively (data not shown). BCG vaccinated, unchallenged hamsters showed a dominant population of Fcnb+ granulocytes consistent with the phagosomal localization of BCG in late endosomal compartments (data not shown). This same ficolin-expressing population of granulocytes was consistently more abundant in BCG-vaccinated SCV2 challenged hamster lungs than in challenged, unvaccinated animals. For the Camp+, Isg15+, Il1m+ and Il1b+ granulocyte subsets, however, BCG vaccination served to attenuate granulocytic cell recruitment to the lung in the presence of ongoing SCV2 (data not shown). Thus for at least certain granulocyte populations BCG vaccination blunted recruitment to the lung consistent with the reduced degree of bronchopneumonia in BCG vaccinated animals that were observed in FIG. 4A.

Similar to our observations in myeloid cells, DEG analysis in SCV2-challenged, unvaccinated animals showed high level transcription of IFN-associated genes (e.g., Mx2, Ifit2) and chemokine genes (e.g., cc15, ccr12) but in BCG vaccinated hamsters there was a shift towards metabolic genes particularly those involved in the oxidative burst (e.g., CytB, Cox2, Cox3) (data not shown).

For BCG-STING, Il1b-granulocytes were not identified, but Sell+granulocytes (Sell =CD62L or L-selectin a cell adhesion molecule) were identified. Thus, there were 6 clusters in both analyses, but there was a minor difference. Nevertheless, the conclusions drawn above are generally correct for BCG-STING (FIG. 12A-B).

Example 11

Other SCV2 Disease Markers

IN BCG- and BCG-STING-Vaccinated Hamsters

Other markers of SCV2 disease in BCG-vaccinated hamsters. SCV2 viral loads were measured in the lungs and tracheal tissue of all animals at d4 and d7 and found no significant reduction although there was a non-significant trend towards reduced counts in BCG vaccinated animals at d7 (data not shown). SCV2 viral load by RT-qPCR shows no statistically significant differences in viral load. The experiment was run in two groups (group 3 and group 4) staggered in time. In the aggregate, there was no significant difference in SCV2 viral loads at either time point. BCG and BCG-STING do not reduce viral load in this non-lethal animal model at the dose of SCV2 used (which was high), but they do appear to reduce disease severity as measured by (i) scRNAseq, (ii) IHC, and (iii) flow cytometry. In the aggregate, there was no significant difference in SCV2 viral loads at either the d4 or d7 sacrifice time points. Among subgroup 3 animals at d7 BCG-vaccinated animals showed a statistically significant decrease in viral load (p<0.01) (data not shown). Similarly, a PET analysis of lesions positive for $^{18}$F-FDG uptake in which lesions were co-registered with pulmonary infiltrates seen by CT did not show a significant difference in the number of PET-positive lesions across the groups at either d4 or d7 (data not shown). Hamsters were subjected to 18F-FDG PET and CT imaging at day 4 and day 7 post-SCV2 challenge. The volumes of inflammatory lesions (PET) which co-registered with pulmonary infiltrates (CT) were measured as a percent of the total lung volume (data not shown). While the results showed average data for the groups, sample CT and PET images from 3 animals evaluated on day 4 post-SCV2 challenge shows that lung infiltration was reduced in certain animals by prior BCG and BCG-STING vaccination (data not shown).

Example 12

Summary of Results

In this study the impact of intravenous BCG and BCG-STING vaccination on the pathogenesis and immunology of SCV2 lung infection in the golden Syrian hamster model was evaluated using traditional tools of histology and flow cytometry supplemented by scRNAseq analysis. The results show that BCG and BCG-STING vaccination prevented the development of severe bronchopneumonia. Concomitantly, BCG and BCG-STING vaccination blunted the T cell lymphopenia in the lungs and reduced granulocyte lung infiltration. BCG and BCG-STING vaccination was also associated with a significant recruitment of macrophages to the lung.

The single cell transcriptional analysis revealed that BCG and BCG-STING vaccination 4 weeks prior to SCV2 challenge was associated with significant shifts both in the populations of cell types present in the lungs and in the DEGs expressed by these cell types. Among lymphoid cells, it was noted a unique lung recruitment of plasma cells in BCG and BCG-STING vaccinated animals that was absent in SCV2-infected animals and also in BCG vaccinated animals that were not SCV2 infected. Treg cell—a tolerizing, anti-inflammatory CD4 cell subset, were more abundant in the lungs in BCG and BCG-STING vaccinated animals. Several abundant lymphoid cell lineages including T helper and Tregs in the lung expressed high levels of type I IFN-associated genes in SCV2-infected animals as would be expected with viral infection; however, in these same cell types, among BCG-vaccinated, SCV2-infected lungs and BCG-STING-vaccinated, SCV2 infected lungs the predominant DEGs were shifted towards antigen presentation. Indeed, gene signature scoring showed that plasma cells from BCG and BCG-STING vaccinated animals showed significantly higher expression of immunoglobulin gene expression than those in unvaccinated animals. The early recruitment of plasma cells and the shift towards transcription of antigen presentation genes suggest that one mechanism by which BCG and BCG-STING prevented severe bronchopneumonia was by accelerated production of anti-viral antibodies.

Among macrophages scRNAseq revealed that BCG vaccination alone in the absence of viral infection produces high levels alveolar macrophages in the lung tissue, a cell type associated with low inflammatory potential and ingestion of debris. Upon SCV2 infection, BCG-vaccinated and BCG-STING-vaccinated animals retained these high levels of AM. In contrast several populations of interstitial macrophages were identified that were considerably higher in unvaccinated lungs than in those of BCG and BCG-STING vaccinated hamsters. As IM are non-resident macrophages likely recruited from the periphery which are known to have high inflammatory capacity, it is possible that a salutary immunologic effect of BCG is prevention of excess pro-inflammatory IM recruitment. While the DEGs of both the AM and IM populations in unvaccinated animals showed high expression of IFN associated and chemokine genes, BCG-vaccinated and BCG-STING-vaccinated lungs showed AM and IM that heavily expressed metabolic and repair genes.

BCG-STING showed two important advantages over BCG. First, BCG-STING recruited more NKT cells and more B cells to the lung than BCG-WT. Second, BCG-STING recruited more AM and more Marco+ AM to the lung than BCG-WT. This study was performed with a high challenge dose of SCV2 (5×10 TCID50 units) and led to severe bronchopneumonia in hamsters.

In summary, the results indicate that BCG and BCG-STING vaccination prevents severe SCV2 bronchopneumonia in hamsters by mechanisms that involve enhanced numbers of lung alveolar macrophages, prevention of SCV2-mediated T cell lymphopenia, and prevention of granulocyte lung infiltration. BCG and BCG-STING appear to accelerate the appearance of immunoglobulin-producing plasma cells in the lung suggesting accelerated antiviral antibody production. The fact that BCG and BCG-STING elevate the abundance of lung Treg cells while shifting a number of cell types away from expression of IFN-associated genes, suggesting that BCG and BCG-STING have immunotolerizing activity. These observations indicate that BCG and BCG-STING vaccination may play a valuable role in protection against SCV2 and suggest that further studies of combining BCG or and BCG-STING with existing COVID-19 vaccines may offer synergistic protection.

Example 13

Anti-Tumor Efficacy of BCG-WT and BCG-STING IS STING-Dependent

Figure 14:
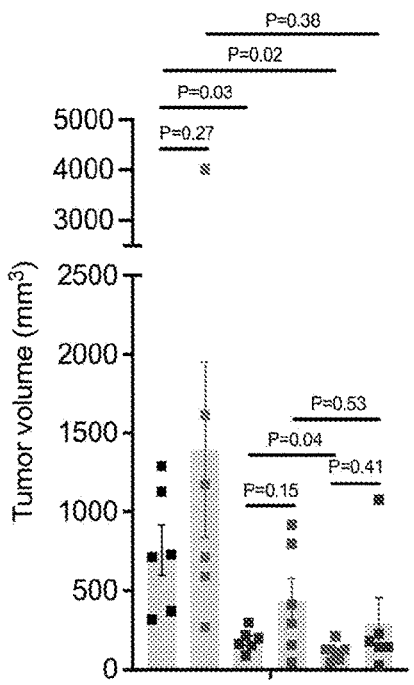
FIG. 14 shows tumor volume at the time of necropsy.

It has been shown that BCG-STING provided superior anti-tumor efficacy than BCG-WT in the heterotopic, syngeneic mouse MB49 bladder cancer model (see WO 2021/163602). To confirm that the mechanism of BCG-STING's superiority is specifically due to its high-level release of a STING agonist (c-di-AMP), MB49 tumor experiments described in the above referenced patent application were performed in STING$^{-/-}$ mice (C57BL/6J-Tmem173gt/J or golden-ticket mice) as well as wild type C57BL/6 mice. Mean tumor weights in MB49-inoculated STING$^{-/-}$ mice were 0.7 g at following BCG-STING (BCG-disA-OE) treatment (not significantly different from untreated WT or untreated STING$^{-/-}$ mice) whereas it was 0.2 g in treated WT mice (p 0.02) (FIG. 13A) and this was associated with an overall reduction of immune (CD45 +) cells infiltrating tumors in STING$^{-/-}$ mice as compared with WT mice (FIG. 13B). Among tumor-infiltrating lymphocytes, there were large reductions in total lymphocytes and activated CD8+ T cells (IFN-g$^+$ CD8 cells, CD25$^+$ CD69$^+$ CD8 cells, and CD69$^+$ CD38$^+$ CD8 cells) in tumors from treated STING$^{-/-}$ mice compared with WT mice, changes that were less pronounced in untreated or BCG-WT treated STING$^{-/-}$ and WT mice (FIG. 13C-F). Likewise, activated tumor-infiltrating macrophages (TNF-a$^+$ F4/80$^+$ CD11b$^+$ cells and TNF-a$^+$ CD206$^+$ CD124$^+$) were notably reduced in BCG-STING (BCG-disA-OE) treated STING$^{-/-}$ mice compared with WT mice (FIG. 13G-H). Tumor volumes also did not decrease with BCG-STING treatment in STING–/– mice (FIG. 14). These findings confirm that the antitumor effects of BCG-disA-OE are largely STING-dependent.

Example 14

Bladder Cancer Anti-Tumor Efficacy of BCG-STING Intravesically is Superior to that of a Small Molecule Sting Agonist Given Intravesically It has been shown that BCG-STING provided superior anti-tumor efficacy than BCG-WT in the rat orthotopic rat MNU model of bladder cancer (see WO 2021/163602). Experiments to determine the anti-tumor efficacy of BCG-STING compared with direct application of a small molecule STING agonist such as ADU-S100 were conducted (structure shown in FIG. 16A). To do this the MNU Fischer rat model was used with 30 rats (Harlan, avg. weight 160 g, age 7 weeks). Briefly, N-methyl-N-nitrosourea (MNU) instillations were given every other week for a total of 4 intravesical bladder instillations using anesthesia with 3% isoflurane. After complete anesthesia, a 20G angiocatheter was placed into the rat's urethra. MNU (1.5mg/kg) (Spectrum) dissolved in 0.9.% sodium chloride was then instilled and the catheter removed, with continued sedation lasting for 60 minutes to prevent spontaneous micturition and allow absorption. MNU was administered every 2 weeks for a total of 4 doses. 2 weeks after the last MNU instillation, intravesical treatment with PBS, 25 micrograms of ADU-S100, 5×10$^6$ CFU of BCG-WT, or 5×10$^6$ CFU of BCG-STING (all given intravesicallyin 0.3m1 via a 20G angiocatheter) was given every week for a total of doses. Rodents were sacrificed 2 d after the last intravesical treatment, and bladders were harvested within 48 hours of the last BCG instillation. At necropsy, rat bladders were removed, and 33% was formalin-fixed, and H&E slides were prepared. A certified genitourinary pathologist reviewed approximately 20 microscopic fields per rat bladder and scored each for tumor stage. The fraction of microscopic fields showing benign, CIS, Ta, or Ti lesions was calculated for each treatment group (FIG. 16B). As shown, without therapy (MNU only), 30% of rat bladder fields showed Ti bladder cancer lesions and 70% showed Ta. In contrast BCG-STING (oeBCG, BCG-disA-OE)-treated rat bladders showed 60% benign bladder tissue and 40% carcinoma in situ (CIS). BCG-WT treated rat bladders showed 100% CIS. ADU-S100-treated rat bladders showed 35% CIS, 25% Ta, and 40% Tl. These results show that intravesical therapy with BCG-STING was superior to BCG-WT in preventing the advancement of bladder cancer pathology to advanced tumors such as Tl and Ta after MNU carcinogenesis. Both were superior to intravesical therapy with ADU-S100.

Example 15

BCG-WT and BCG-STING Promote an Influx of Glucose from the Extracellular Space to the Intracellular Space by Upregulation of Glucose Transporters It was previously shown that human monocyte derived macrophages treated with BCG-STING took up significantly higher levels of glucose into the intracellular space than did the same cells treated with BCG-WT (see WO 2021/163602). In order to determine whether the elevated levels of intracellular glucose were due to increased transport or to increased gluconeogenesis, the expression of the major glucose transporter GLUT1 in macrophages exposed to BCG-WT and BCG-disA-OE was tested. Murine BMDM with BCG or BCG-STING (BCG-disA-OE) were challenged for 4 hours, and after washing and recovery in glucose-free media, macrophages were treated with the fluorescent 2-deoxy-glucose analogue 2-NBDG for 2 hours and subsequently analyzed by flow cytometry for levels of GLUT1 expression or 2-NBDG uptake. As may be seen in FIG. 15A, exposure to BCG-WT and BCG-STING (BCG-disA-OE) led to a 2-fold (p 0.06) and more than a 5-fold (p 0.002) increase, respectively, of GLUT1 expression on BMDM compared to unexposed cells. Similarly, 2-NBDG levels were elevated by 20% (p 0.06) or 40% (p 0.003) following exposure to BCG-WT and BCG-disA-OE, respectively as shown in FIG. 15B. These observations strongly suggest that BCG-disA-OE elicits higher levels of the GLUT1 transporter and glucose uptake than BCG-WT or untreated controls resulting in greater accumulation of intracellular glucose and are consistent with earlier observations linking trained immunity and STING activation with enhanced mTOR-HIF-1a pathway activation and concomitant elevations in glucose transporter levels.

The mechanism of increased glucose accumulation in macrophages by BCG-STING is due to increased transport into cells rather than increased gluconeogenesis (FIG. 15A-B). Intracellular uptake of fluorescent glucose was determined. Briefly, macrophages were infected at a ratio of 1:20 (macrophage vs BCG ratio) in presence of glucose free medium followed by exogenous addition of 2-NBDG. Macrophages were subsequently stained for GLUT1 and were investigated using flow cytometry. Data analyses was carried out using Flowjo® and Graphpad prism® softwares. 2-tailed Student's t-test (n=2 experimental replicates) (FIG. 15).

Example 16

BCG and BCG-STING Vaccination may Prevent the Development of Non-Tuberculous Mycobacterial Infections in Cystic Fibrosis Patients It was evaluated to determine whether country-specific BCG vaccination policies were associated with differing annual (pulmonary nontuberculous mycobacteria) NTM prevalence rates among individuals with CF from 2009 to 2018 using the European Cystic Fibrosis Society Patient Registry (ECFSPR). NTM prevalence in each country was defined as the proportion of individuals with a positive NTM culture amongst all individuals with available NTM data during each year of observation. Beginning in 2011, the ECSFPR began reporting NTM infections separately for pediatric and adult CF patients, allowing for separate calculation of the NTM prevalence in these age groups. Per country NTM data for a given study year and age group (pediatric or adult) was excluded from analysis if the registry reported data represented fewer than 10 individuals or if there was greater than 70% percent missing NTM data in that year.

Study countries were categorized by universal BCG vaccination policy as active or suspended, and for suspended countries by the decade in which universal BCG vaccination was suspended: pre-1990, 1990 to <2000, 2000 to <2010, or after 2010.

Figure 17A:
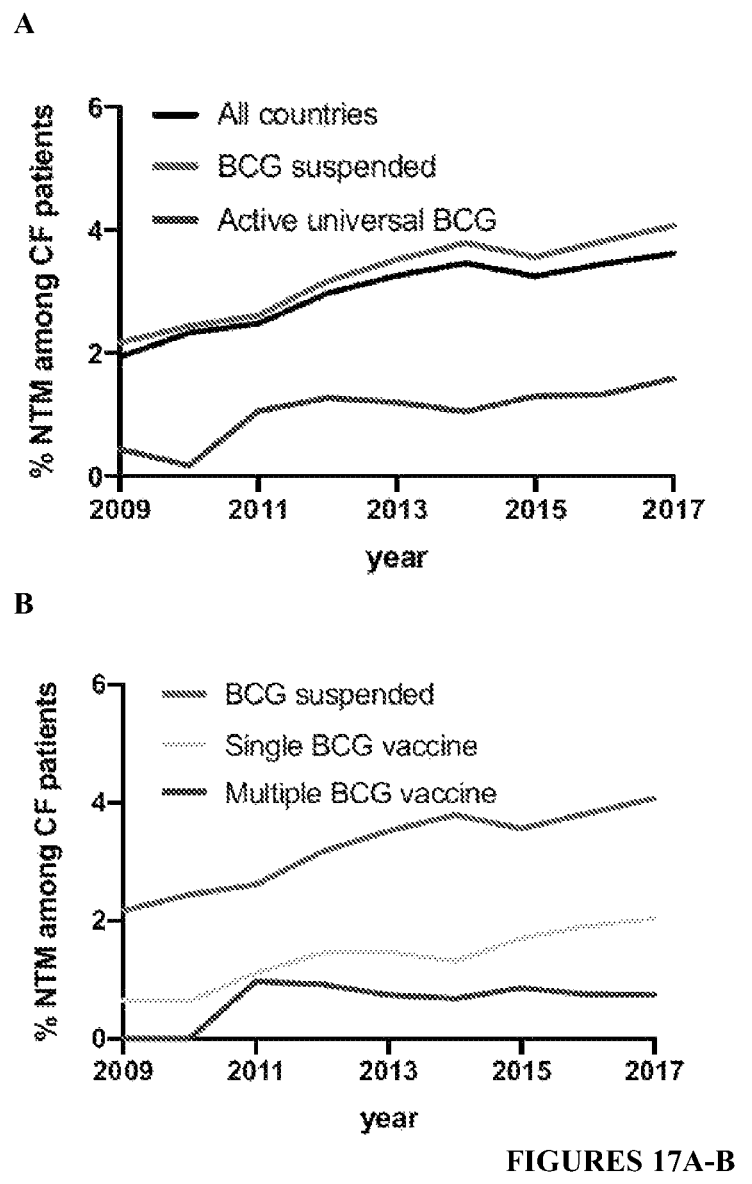

Between 2009 and 2018, a total of 37 European and certain nearby Mediterranean countries (Turkey, Israel) contributed at least one annual summary of NTM infections to the ECFSPR. Country-level data for a given year was excluded if there were fewer than 10 individuals with NTM data reported or if greater than 70% of NTM data was missing. These criteria enabled us to include and analyze the following numbers of countries: 14 for 2019, 14 for 2010, 22 for 2011, 23 for 2012, 23 for 2013, 21 for 2014, 24 for 2015, 26 for 2016, 20 for 2017, and 31 for 2018. Following application of these exclusion criteria, a total of 33 countries were utilized for the primary NTM analysis, with a range of 20 to 27 countries per year included in the adult analysis, and a range of 19 to 28 countries per year included in the pediatric analysis. BCG vaccination practices of included countries were as follows: multiple BCG vaccinations 12 countries (Armenia, Austria, Czech Republic, France, Germany, Greece, Ireland, Russian Federation, Slovak Republic, Slovenia, Sweden, and Ukraine) and single BCG vaccinations 17 countries (Albania, Denmark, Georgia, Hungary, Israel, Latvia, Lithuania, North Macedonia, Norway, Poland, Portugal, Romania, Serbia, Spain, Switzerland, Turkey and the United Kingdom). European countries that contributed data on annual NTM rates in cystic fibrosis (CF) patients to the European Cystic Fibrosis Society Patient Registry (ECFSPR) from 2009 to 2017 were categorized by BCG vaccination policy as active or suspended. Map created with mapchart.net. Among the study countries, universal BCG vaccination was in place in 2011 in 15 countries (Albania, Armenia, Croatia, Georgia, Greece, Hungary, Ireland, Latvia, Lithuania, North Macedonia, Poland, Portugal, Romania, Russian Federation, and Serbia), 11 countries had suspended universal BCG vaccination by 2011 (Austria, Czech Republic, Denmark, France, Germany, Israel, Norway, Slovak Republic, Slovenia, Spain, and Sweden), and four countries never utilized a universal BCG vaccination strategy (Belgium, Cyprus, Italy, and The Netherlands). Of note, three countries suspended BCG vaccination during the study period: Norway (2009), the Czech Republic (2010) and the Slovak Republic (2011). Countries that continue to BCG vaccinate had a statistically significant lower rate of NTM infection compared to countries in which universal BCG vaccinations has been suspended (incidence rate ratio [IRR]: 0.38; 95% CI: 0.26, 0.54) (FIG. 17AB). FIG. 17B shows annual NTM infection rates in CF patients for countries that provided universal BCG vaccination during the study period grouped by BCG vaccination strategy (single vs. multiple dose) in comparison to countries that have suspended BCG vaccination. Among the 16 countries that previously utilized universal BCG vaccination strategy, five suspended before 1990, two suspended between 1990 and 2000, four suspended between 2000 to 2010, and five countries suspended BCG vaccination after 2010.

During the study period, the overall annual prevalence of NTM among European CF patients increased from 1.94% in 2009 to 4.10% in 2018. Higher NTM prevalence was observed among adult patients (3.41% in 2011 to 6.26% in 2018) relative to pediatric CF patients (1.55% in 2011 to 1.83% in 2018).

In all study years, countries with active universal BCG vaccination policies reported lower prevalence of NTM infection compared to countries that no longer BCG vaccinate even when accounting for TB burden (FIG. 17A-B). Among countries with active BCG vaccination, prevalence of NTM infections increased from 0.44% in 2009 to 1.59% in 2017 (PR: 1.14; 95% CI: 1.07, 1.22), whereas in countries that have suspended BCG vaccination, prevalence of NTM infections increased from 2.17% in 2009 to 4.07% in 2017 (PR: 1.06; 95% CI: 1.04, 1.07). Countries that continue to BCG vaccinate had a statistically significant lower annual prevalence of NTM infection compared to countries in which universal BCG vaccinations has been suspended (PR: 0.28; 95% CI: 0.17, 0.45).

Example 17

Cystic Fibrosis Data Summary

Significantly lower annual prevalence of pulmonary NTM infection among CF patients in Europe was observed in countries with universal BCG vaccination policies in comparison to countries where BCG vaccination has been discontinued. NTM was less common among CF patients in countries that utilize a multiple vaccination strategy in comparison to countries that only provide a single BCG vaccination, however, this finding was not statistically significant. BCG vaccination may provide protection against pulmonary NTM infection in CF, and there may be a protective advantage conferred by repeated dosing.

Multiple epidemiologic studies have observed a relationship between discontinuation of BCG vaccination and increased pediatric NTM infections, and there are also human and animal data of protective efficacy of BCG against NTM in vivo. BCG has been shown to confer heterologous protection against multiple infectious organisms, through a mechanism dubbed "trained immunity" involving epigenetic changes that increase the immune setpoint against unrelated antigenic stimuli. While BCG has been associated with protective efficacy against NTM, viral infections, and cancer, these data suggest a potential benefit of BCG for the CF community.

There are several limitations to the present investigation. While the ECFSPR is comprehensive, not all countries contributed annual data throughout the study period and some countries reported missing NTM infection data; therefore, biases in reporting or culturing practices may have influenced observed associations. National NTM species-level data are not included in the ECFSPR annual reports, preventing a species-specific analysis. Similarly, the ECFSPR reports NTM infection, rather than NTM pulmonary disease, thus the relationship between BCG vaccination and NTM disease in CF—a more clinically relevant endpoint—could not be ascertained. Country-specific BCG vaccination policies were derived from the most comprehensive sources we could identify, however, countries that have suspended universal BCG vaccination may continue to provide BCG vaccination to high-risk patients, including CF patients, which may result in within-country heterogeneity of BCG exposure. Both cessation and reduced frequency of BCG vaccination are likely surrogates for waning TB incidence, and TB exposure may in fact confer significant cross-protection against NTM. Lastly, given the nature of the study, we were unable to account for individual level characteristics which may increase risk for NTM infection, such as geography, socioeconomic status, migration patterns, immunizing BCG strain or differences in clinical practice patterns.

Example 18

Effect of BCG-STING in Animal Models of Bladder Cancer and Tuberculosis

The efficacy of BCG-disA-OE and BCG-WT for TB prevention of disease was assessed using the guinea pig model. Guinea pigs vaccinated with PBS, BCG-disA-OE or BCG-WT, were challenged with virulent Mtb, and sacrificed 18 wks later. Compared with BCG-WT, BCG-disA-OE reduced TB disease progression by three parameters: lung weight, lung pathology score, and lung Mtb CFU counts. Using the MB-49 mouse heterotopic flank tumor model, BCG-disA-OE was more effective than BCG-WT in (i) reducing tumor weight, (ii) increasing tumor-associated IFN$\gamma^4$ CD4 cells to the tumor, and (iii) reducing tumor-ssociated CD4 Treg cells. Model: C57BL/6 mice (n=10/group) were injected with $3\times10^5$ MB-49 cells on day 0. Intratumoral administration of PBS (No Tx) or $10^6$ BCG was given on d13, d16, and d19. The mice were sacrificed on d21 for tumor weight and flow cytometry.  p<0.01, * p<0.001, ****p<0.0001. BCG-disA-OE was more effective than BCG-WT in two different animals models of bladder cancer (data not shown).

Immunocompetent BALB/c mice vaccinated with BCG-disA-OE showed significantly reduced Mtb burdens in lungs compared to mice vaccinated with BCG-WT (data not shown). Similarly, time-to-death studies in immunodeficient SCID mice exposed to the two BCG strains by aerosol revealed prolonged survival after BCG-disA-OE strains compared to BCG-WT strains (data not shown). We also found increased levels of pro-inflammatory cytokines in the lungs and spleens of BALB/c mice infected with BCG-disA-OE compared to levels with BCG-WT (data not shown).

Example 19

Trained Immunity Effects of BCG-STING

Pro-inflammatory cytokines. It was found that urinary bladders from rats treated with BCG-disA-OE showed a significant induction of IFN$\alpha\beta$, IFN-$\gamma$, TNF-$\alpha$, TGF-$\beta$, iNOS, IP-10, MCP-1 and MIP-1 $\alpha$ in comparison to untreated or BCG-WT treated rats (data not shown). Evidence for increased infiltration of CCL2$^+$ M$\Phi$1, Nos2$^+$ and IL-1 $\beta^+$ M1 M$\Phi$ (accompanied by increased IL-6, IFN-$\gamma$, and IFN-$\alpha$ expression) in bladders of rats treated with BCG-disA-OE was also found. Interestingly, increased levels of IP-10 was found, that together with increased IFN- y is known to promote a strong T cell recruitment at the site of infection and inflammation (data not shown). Importantly, we have recapitulated these data with human PBMCs from 5 healthy controls and observed a significantly greater increase in TNF $\alpha$ and IL-6 with BCG-disA-OE over BCG-WT (data not shown).

Macrophage reprogramming. Recent research has identified numerous M$\Phi$ subsets including those with proinflammatory functions (referred to as M1 M$\Phi$) and anti-inflammatory tumor-promoting function (M2 M$\Phi$). In addition, myeloid-derived suppressor cells (MDSCs) are known to play important roles in suppressing anti-tumor and anti-infective immune responses. The capability of BCG-disA-OE vs BCG-WT was examined in training Mcp experiments to determine reprogramming to inflammatory subsets occurs. As shown in FIG. 43, exposure of human PBMCs to BCG-disA-OE induces a more potent myeloid cell shift towards an M1 phenotype than occurs with BCG-WT. Specifically, (i) overall numbers of inflammatory M$\Phi$ s, (ii) TNF$\alpha$-expressing M1 M$\Phi$s, and (iii) IL-6-expressing M1 M$\Phi$ s. In contrast, the abundance of immunosuppressive myeloid cell types was decreased including (iv) overall numbers of M2-type Mcps and (v) IL-10-expressing M2 M$\Phi$ s. p<0.01, *p<0.001. (data not shown).

Epigenetic training. Trained immunity-induced in M$\Phi$s is mediated by epigenetic reprogramming at the level of histone methylation and acetylation. To examine the hypothesis that recombinant BCG strains not only induce an innate immune memory response, but also reprogram human monocytes metabolically and epigenetically and prime them to respond better in the face of subsequent challenge, human monocytes were isolated from peripheral blood of healthy donors and challenged them in culture with wild-type and disA-OE strains of BCG (MOI of 5:1) for 3 h. Non-attached cells and non-internalized bacteria were removed by repeated washing and cells were allowed to rest for 6 days in RPMI containing penicillin-streptomycin. Cells were re-stimulated using the TLR agonist Pam3CSK4 (300 ng/µl) overnight and the MΦs were examined for epigenetic changes by chromatin immunoprecipitation sequencing (ChIP-seq) to determine changes in the distribution of histone H3 mono-methylation at lysine 4 (H3K4me1), a marker of active promoters and enhancers. Significantly greater enhancement of H3K4 methylation on IL-6 was found and TNFα promoters was induced by BCG-disA-OE compared with BCG-WT. In addition, a significant decrease in H3K9 methylation and an enhancement of H3K27 acetylation on TNFα and IL-6 promoters was found (data not shown).

Autophagy training. Autophagy is a key host defense mechanism to clear intracellular pathogens. Autophagy has been shown to modulate BCG-induced trained immunity, although the precise pathway linking autophagy to epigenetic changes in trained immunity is unknown. It was recently found that BCG-disA-OE enhances autophagy in bladder tumor cells. This represents yet another marker of trained immunity.

Although the invention has been described with reference to the above example, it will be understood that modifications and variations are encompassed within the spirit and scope of the invention. Accordingly, the invention is limited only by the following claims.

What is claimed is:

1. A method of preventing, ameliorating or treating a viral infection in a subject comprising administering to the subject a recombinant bacille Calmette-Guerin (BCG) bacterial strain of *Mycobacterium bovis* comprising an exogenous nucleic acid construct comprising:

a mycobacterial promoter and a disA gene, wherein the disA gene is a *Mycobacterium* tuberculosis gene, and wherein the viral infection is a primary respiratory infection thereby treating the infection.

2. The method of claim 1, wherein the infection is a SARS-CoV-2 infection.

3. The method of claim 1, wherein the subject has a condition selected from the group consisting of obesity, diabetes, cystic fibrosis (CF), non-cystic-fibrosis bronchiectasis, and HIV/AIDS.

4. The method of claim 1, wherein the bacterial strain over expresses a stimulator of interferon genes (STING) agonist.

5. The method of claim 4, wherein the STING agonist is c-di-AMP.

6. The method of claim 1, wherein the disA gene is fused to the mycobacterial promoter.

7. The method of claim 1, wherein the nucleic acid construct does not have kanamycin resistance markers.

8. The method of claim 1, wherein the bacterial strain is optionally resistant to kanamycin.

9. The method of claim 1, wherein the bacterial strain comprises a selectable marker.

10. The method of claim 1, wherein the mycobacterial promoter is Hsp60 promoter.

11. The method of claim 1, wherein the exogenous nucleic acid construct further comprises a ppiA signal sequence and optionally a spike protein of SARS-COV-2.

12. The method of claim 1, wherein the exogenous nucleic acid construct further comprises a ppiA signal sequence and optionally the receptor binding domain of the spike protein of SARS-COV-2.

13. The method of claim 11, wherein the nucleic acid construct further comprises a signal peptide.

14. The method of claim 13, wherein the signal peptide comprises a ppiA signal sequence.

* * * * *